US009434946B2

(12) United States Patent
Adamsky et al.

(10) Patent No.: US 9,434,946 B2
(45) Date of Patent: Sep. 6, 2016

(54) COMBINATION THERAPY FOR TREATING HEARING AND BALANCE DISORDERS

(71) Applicant: QUARK PHARMACEUTICALS, INC., Fremont, CA (US)

(72) Inventors: Svetlana Adamsky, Gedera (IL); Elena Feinstein, Rehovot (IL)

(73) Assignee: QUARK PHARMACEUTICALS, INC., Fremont, CA (US)

( * ) Notice: Subject to any disclaimer, the term of this patent is extended or adjusted under 35 U.S.C. 154(b) by 0 days.

(21) Appl. No.: 14/588,955

(22) Filed: Jan. 4, 2015

(65) Prior Publication Data

US 2015/0126586 A1 May 7, 2015

Related U.S. Application Data

(63) Continuation of application No. 14/367,939, filed as application No. PCT/US2013/020918 on Jan. 10, 2013, now abandoned.

(60) Provisional application No. 61/585,672, filed on Jan. 12, 2012.

(30) Foreign Application Priority Data

Aug. 3, 2012 (WO) ................ PCT/US2012/049616

(51) Int. Cl.
| | |
|---|---|
| *C12N 15/11* | (2006.01) |
| *A61K 48/00* | (2006.01) |
| *C07H 21/02* | (2006.01) |
| *C07H 21/04* | (2006.01) |
| *C12N 15/113* | (2010.01) |

(52) U.S. Cl.
CPC ......... *C12N 15/113* (2013.01); *C12N 2310/14* (2013.01); *C12N 2320/31* (2013.01)

(58) Field of Classification Search
USPC .......................................... 514/44; 536/24.5
See application file for complete search history.

(56) References Cited

U.S. PATENT DOCUMENTS

| | | | |
|---|---|---|---|
| 7,618,814 | B2 | 11/2009 | Bentwich |
| 2011/0142917 | A1 | 6/2011 | Alpert et al. |
| 2011/0178157 | A1 | 7/2011 | Jin et al. |

FOREIGN PATENT DOCUMENTS

| | | |
|---|---|---|
| WO | 02/04605 A2 | 1/2002 |
| WO | 2009/147684 A2 | 12/2009 |

(Continued)

OTHER PUBLICATIONS

Ambros, V., "The Functions of Animal MicroRNAs," Nature, 431, Sep. 16, 2004; pp. 350-355.

(Continued)

*Primary Examiner* — Terra C Gibbs
(74) *Attorney, Agent, or Firm* — Nutter McClennen & Fish LLP; Konstantin Linnik; Isaac A. Hubner

(57) ABSTRACT

The present application relates to combinations of inhibitors directed at down-regulation of genes associated with hearing loss including HES1, HES5, HEY2, CDKN1B and NOTCH1, exhibiting a beneficial effect and useful in treating or attenuating hearing loss, treating balance impairment, promoting the replacement, regeneration, or protection of otic (sensory) hair cells of the inner ear, and or effecting hearing restoration/regeneration.

17 Claims, 3 Drawing Sheets

(56) References Cited

FOREIGN PATENT DOCUMENTS

| WO | 2011/153348 A2 | 12/2011 |
| WO | 2013/020097 A1 | 2/2013 |

OTHER PUBLICATIONS

Bark, S., "Silence of the Transcripts," J. Mol. Med., (2005) 83: 764-773.
Bellon et al., "Amino-Linked Ribozymes: Post-Synthetic Conjugation of Half-Ribozymes," Nucleosides and Nucleotides, 16:7-9, 951-954.
Bellon et al., "Post-Synthetically Ligated Ribozymes: An Alternative Approach to Iterative Solid-Phase Synthesis," Bioconjugate Chem. 1997, 8, 204-212.
Bernstein et al., "Role for a Bidentate Ribonuclease in the Initiation Step of RNA Interference," Nature, (2001) 409, pp. 363-366.
Bitko et al., "Inhibition of Respiratory Viruses by Nasally Administered siRNA," Nature Med., (2005) 11:1; pp. 50-55.
Braasch et al., "RNA Interference in Mammalian Cells by Chemically-Modified RNA," Biochemistry 2003, 42, 7967-7975.
Breuskin et al., "Strategies to regenerate hair cells: Identification of progenitors and critical genes", Hearing Res., vol. 236, No. 1-2, Jan. 30, 2008, pp. 1-10.
Caruthers, et al., "Chemical Synthesis of Deoxyoligonucleotides by the Phosphoramidite Method," Meth. Enzymol. 154; pp. 287-313.
Chakraborty, C., "Potentiality of Small Interfering RNAs (siRNA) as Recent Therapeutic Targets for Gene-Silencing," Curr. Drug Targets, 2007, 8, pp. 469-482.
Chalk et al., "Improved and Automated Prediction of Effective siRNA," Biochem. Biophys. Res. Comm., 319, (2004), 264-274.
Choi et al., "Effect of Poly(ethylene glycol) Grafting on Polyethylenimine as a Gene Transfer Vector in vitro," Bull. Korean Chem. Soc. 2001, vol. 22, No. 1; pp. 46-52.
Doetzlhofer et al.: "Hey2 Regulation by FGF Provides a Notch-Independent Mechanism for Maintaining Pillar Cell Fate in the Organ of Corti", Devel. Cell, vol. 16, No. 1, Jan. 1, 2009, pp. 58-69.
Eckstein, F., "Nucleoside Phosphorothioates," Ann. Rev. Biochem. (1985), 54:367-402.
Furgeson, et al., "Modified Linear Polyethylenimine-Cholesterol Conjugates for DNA Complexation," Bioconjugate Chem. 2003, 14, 840-847.
Gil et al., Induction of apoptosis by the dsRNA-dependent protein kinase (PKR): Mechanism of action; Apoptosis 2000; 5: 107-114.
Godbey et al., "Poly(ethylenimine) and its role in gene delivery," Journal of Controlled Release 60 (1999) 149-160.
Gonzalez et al., "New Class of Polymers for the Delivery of Macromolecular Therapeutics," Bioconjugate Chem. 1999, 10, 1068-1074.
International Search Report and Written Opinion for Application No. PCT/US2012/049616, mailed Jan. 9, 2013 (11 pages).
International Preliminary Report on Patentability for Application No. PCT/US2012/049616, issued Feb. 4, 2014 (8 pages).
International Search Report and Written Opinion for Application No. PCT/US2013/020918, mailed Apr. 10, 2013 (13 pages).
International Preliminary Report on Patentability for Application No. PCT/US2013/020918, issued Jul. 15, 2014 (8 pages).
Izant et al., "Constitutive and Conditional Suppression of Exogenous and Endogenous Genes by Anti-Sense RNA," Science, (1985) 229, pp. 345-352.
Kashani-Sabet et al., "Reversal of the Malignant Phenotype by an Anti-ras Ribozyme," Antisense Res. and Devel., 2:3-15 (1992).
Kunath et al., "The Structure of PEG-Modified Poly(Ethylene Imines) Influences Biodistribution and Pharmacokinetics of Their Complexes with NF- B Decoy in Mice," Pharmaceutical Research, vol. 19, No. 6, Jun. 2002, pp. 810-817.
Lee et al., "The nuclear RNase III Drosha initiates microRNA Processing," Nature, (2003) 425, pp. 415-419.
Lewis et al., "Efficient Delivery of siRNA for Inhibition of Gene Expression in Postnatal Mice," Nature Genetics, (2002) 32, pp. 107-108.
Lieber et al., "Stable High-Level Gene Expression in Mammalian Cells by T7 Phage RNA Polymerase," Methods in Enzymology, (1993) 217, pp. 47-66.
McManus et al., "Gene Silencing in Mammals by Small Interfering RNAs," Nature Reviews Genetics; (2002) 3, pp. 737-747.
Ono K., et al., "RNA interference for p27kip1 induce supporting cell proliferation in organotypic cultures of postnatal mammalian cochlea," vol. 58, Jan. 1, 2007.
Paddison et al., "siRNAs and shRNAs: Skeleton keys to the human genome," Curr. Opinion Molec. Therapeutics 2003 5(3):217-224.
Paul et al., "Effective expression of small interfering RNA in human cells," Nature Biotech. (2002) 29; pp. 505-508.
Simantov et al., "Dopamine-induced Apoptosis in Human Neuronal Cells: Inhibition by Nucleic Acids Antisense to the Dopamine Transporter," Neuroscience, (1996) vol. 74, No. 1, pp. 39-50.
Sioud et al., "Potential Design Rules and Enzymatic Synthesis of siRNAs," From: Methods in Molec. Biol., (2004), 252: 457-69.
Sorensen et al., "Gene Silencing by Systemic Delivery of Synthetic siRNAs in Adult Mice," J. Mol. Biol. (2003) 327, 761-766.
Soukup et al., "Little but loud: Small RNAs have a resounding affect on ear development", Brain Res, 2009, 1277:104-114.
Tateya et al.: "Cooperative functions of Hes/Hey genes in auditory hair cell and supporting cell development", Devel. Biol., vol. 352, No. 2, Jan. 28, 2011, pp. 329-340.
Tolentino et al., "Intravitreal Injection of Vascular Endothelial Growth Factor Small Interfering RNA Inhibits Growth and Leakage in a Nonhuman Primate, Laser-Induced Model of Choroidal Neovascularization," Retina; (2004) 24:1, pp. 132-138.
Wincott et al., "A Practical Method for the Production of RNA and Ribozymes," Methods in Molec. Biol., (1997) v. 74, pp. 59-68.
Zhang et al., "Pifithrin-alpha suppresses p53 and protects cochlear and vestibular hair cells from cisplatin-induced apoptosis," Neuroscience. 2003;120(1):191-205.
Zine et al.: "Notch signaling regulates the pattern of auditory hair cell differentiation in mammals", Development, vol. 127, No. 15, Aug. 2000, pp. 3373-3383.

1KHz

4 KHz

8 KHz

16 KHz

32 KHz

LEGEND

- CONTRALATERAL
- PBS + VEHICLE
- KM + EA
- KM + EA + VEHICLE
- KM + EA + combination of HES1 dsRNA + HES5 dsRNA+ HEY2 dsRNA
- KM + EA + combination of HES1 dsRNA +HEY2 dsRNA +EGFP dsRNA
- KM + EA + combination of NOTCH1 dsRNA +CDKN1B dsRNA + HEY2 dsRNA
- KM + EA + EGFP dsRNA

COMBINATION THERAPY FOR TREATING HEARING AND BALANCE DISORDERS

RELATED APPLICATIONS

This is a continuation of U.S. patent application Ser. No. 14/367,939, filed Jun. 23, 2014, now abandoned, which is the U.S. National Stage of International Patent Application No. PCT/US2013/020918, filed Jan. 10, 2013, which claimed the benefit of U.S. Provisional Application No. 61/585,672 filed Jan. 12, 2012, and PCT Application No. PCT/US12/49616 filed Aug. 3, 2012, which are incorporated herein by reference in their entirety and for all purposes.

SEQUENCE LISTING

This application incorporates-by-reference nucleotide and/or amino acid sequences which are present in the file named "237-PCT2.5T25.txt", which is 5.044 megabytes in size, and which was created on Jan. 9, 2013 in the IBM-PC machine format, having an operating system compatibility with MS-Windows, and is submitted herewith.

FIELD OF THE INVENTION

The present disclosure relates to combination therapy, including compositions and methods useful for treating hearing loss, treating balance impairment, promoting the replacement, regeneration, or protection of otic hair (sensory) cells of the inner ear, or effecting hearing restoration/regeneration.

BACKGROUND OF THE INVENTION

PCT application No. PCT/US12/49616 to the assignee of the present application relates to double stranded RNA compounds, pharmaceutical compositions comprising same and methods of use thereof for the down-regulation of target genes associated with hearing loss and balance impairment, including HES1, HES5, HEY1, HEY2, ID1, ID2, ID3, CDKN1B, and NOTCH1, the inhibition of which is useful for treating hearing loss, treating balance impairment, promoting the replacement, regeneration, or protection of otic hair (sensory) cells of the inner ear, or effecting hearing restoration/regeneration.

SUMMARY OF THE INVENTION

It has now been found that certain tripartite combinations of inhibitors directed at down-regulation of certain target genes associated with hearing and balance disorders are beneficial in treating or attenuating hearing loss, treating balance impairment, promoting the replacement, regeneration, or protection of otic (sensory) hair cells of the inner ear, and/or effecting hearing restoration/regeneration. In particular, the combination includes a first agent targeting HES1, a second agent targeting HES5 and a third agent targeting HEY2, or includes a first agent targeting CDKN1B, a second agent targeting NOTCH1 and a third agent targeting HEY2.

In one aspect, provided herein is a combination of a HES1 inhibitor, a HES5 inhibitor and a HEY2 inhibitor for use in therapy. In some embodiments the therapy comprises preventing, treating, or delaying of progression of a hearing disorder, a hearing loss, and/or a balance impairment, or for preventing the loss of otic (sensory) hair cells of the inner ear in a subject. In another aspect provided herein is a composition comprising a combination of a HES1 inhibitor, or a pharmaceutically acceptable salt or prodrug thereof, a HES5 inhibitor, or a pharmaceutically acceptable salt or prodrug thereof and a HEY2 inhibitor, or a pharmaceutically acceptable salt or prodrug thereof; and a pharmaceutically acceptable carrier. In yet another aspect provided herein is a method of preventing, treating, or delaying of progression of a hearing disorder, a hearing loss, and/or a balance impairment, or of preventing the loss of otic (sensory) hair cells of the inner ear in a subject, comprising administering to the subject a HES1 inhibitor, a HES5 inhibitor and a HEY2 inhibitor. In another aspect provided herein is a product, a kit or a commercial package comprising a HES1 inhibitor, a HES5 inhibitor and a HEY2 inhibitor or a composition thereof as disclosed hereinabove.

In yet another aspect provided herein is a combination of a CDKN1B inhibitor, a NOTCH1 inhibitor, and a HEY2 inhibitor for use in for use in therapy. In some embodiments the therapy comprises preventing, treating, or delaying of progression of a hearing disorder, a hearing loss, and/or a balance impairment, or for preventing the loss of otic (sensory) hair cells of the inner ear in a subject. In another aspect provided herein is a composition comprising at least one CDKN1B inhibitor, or a pharmaceutically acceptable salt or prodrug thereof, at least one NOTCH1 inhibitor, or a pharmaceutically acceptable salt or prodrug thereof; and at least one HEY2 inhibitor, or a pharmaceutically acceptable salt or prodrug thereof; and a pharmaceutically acceptable carrier. In yet another aspect provided herein is a method of preventing, treating, or delaying of progression of a hearing disorder, a hearing loss, and/or a balance impairment, or of preventing the loss of otic (sensory) hair cells of the inner ear in a subject, comprising administering to the subject a CDKN1B inhibitor, a NOTCH1 inhibitor and a HEY2 inhibitor In another aspect provided herein is a product, a kit or a commercial package comprising a CDKN1B inhibitor, a NOTCH1 inhibitor and a HEY2 inhibitor or a composition thereof as disclosed hereinabove.

In various aspects and embodiments of the combinations and methods provided herein a therapeutically effective amount of each of the inhibitors is administered substantially simultaneously, separately or sequentially and in any order, and the components are administered separately or as a fixed combination (for example in a single dosage form). In some embodiments of the combinations and methods provided herein, each of the inhibitors is administered substantially simultaneously or sequentially and in any order. In other embodiments of the combinations and methods provided herein, a therapeutically effective amount of two of the inhibitors is administered simultaneously or substantially simultaneously and the third inhibitor is administered separately.

In one embodiment, provided herein is a combination of a HES1 inhibitor, a HES5 inhibitor and a HEY2 inhibitor, for substantially simultaneous or sequential use in preventing, treating, or delaying of progression of a hearing disorder, a hearing loss, and/or a balance impairment, or for preventing the loss of otic (sensory) hair cells of the inner ear in a subject.

In another embodiment, provided herein is a combination of a CDKN1B inhibitor, a NOTCH1 inhibitor and a HEY2 inhibitor, for substantially simultaneous or sequential use in preventing, treating, or delaying of progression of a hearing disorder, a hearing loss, and/or a balance impairment, or for preventing the loss of otic (sensory) hair cells of the inner ear in a subject.

In one embodiment provided are methods for treating, including preventing, the incidence or severity of hearing loss in a subject in which expression of HES1, HES5, and HEY2 genes is associated with the etiology or progression of the hearing disorder/hearing loss.

In another embodiment, provided are methods for treating, including preventing, the incidence or severity of balance impairment in a subject in which expression of HES1, HES5, and HEY2 genes is associated with the etiology or progression of the balance impairment.

In yet another embodiment, provided are methods for treating, including preventing, the incidence or severity of loss of otic (sensory) hair cells of the inner ear in a subject, in which expression of HES1, HES5, and HEY2, genes is associated with the etiology or progression of the otic (sensory) hair cell loss.

In one embodiment, provided are methods for treating, including preventing, the incidence or severity of hearing loss in a subject in which expression of CDKN1B, NOTCH1 and HEY2 genes is associated with the etiology or progression of the hearing disorder/hearing loss.

In another embodiment, provided are methods for treating, including preventing, the incidence or severity of balance impairment in a subject in which expression of CDKN1B, NOTCH1 and HEY2 genes is associated with the etiology or progression of the balance impairment.

In yet another embodiment, provided are methods for treating, including preventing, the incidence or severity of loss of otic (sensory) hair cells of the inner ear of a subject, in which expression of CDKN1B, NOTCH1 and HEY2, genes is associated with the etiology or progression of the otic (sensory) hair cell loss.

In one embodiment provided herein is a method of preventing, treating or delaying progression of a hearing disorder, a hearing loss, and/or a balance impairment, or of preventing the loss of otic (sensory) hair cells of the inner ear in a subject, comprising administering to the subject a HES1 inhibitor, a HES5 inhibitor and a HEY2 inhibitor.

In another embodiment provided herein is a method of preventing, treating, or delaying of progression of a hearing disorder, a hearing loss, and/or a balance impairment, or of preventing the loss of otic (sensory) hair cells of the inner ear in a subject, comprising administering to the subject a CDKN1B inhibitor, a NOTCH1 inhibitor and a HEY2 inhibitor.

In some embodiments the subject is a mammal. In a preferred embodiment the subject is a human subject.

Further provided is a method of preventing degeneration of the auditory nerve in a subject comprising administering to the subject a combination disclosed herein.

Such methods involve administering to a mammal in need of such treatment a combination or a composition comprising prophylactically or therapeutically effective amount of a HES1 inhibitor, a HES5 inhibitor and a HEY2 inhibitor. In another embodiment, such methods involve administering to a mammal in need of such treatment a combination or a composition comprising prophylactically or therapeutically effective amount of a CDKN1B inhibitor, a NOTCH1 inhibitor and a HEY2 inhibitor.

In various embodiments, each inhibitor (the HES1 inhibitor, the HES5 inhibitor, the HEY2 inhibitor, the CDKN1B inhibitor, and the NOTCH1 inhibitor) is independently selected from the group consisting of a small organic molecule; a protein, an antibody or a fragment thereof, a peptide, a peptidomimetic and a nucleic acid molecule.

In preferred embodiments, each inhibitor comprises a therapeutic nucleic acid molecule, or a pharmaceutically acceptable salt thereof. In some embodiments, the nucleic acid compound is applied directly to the round window membrane of the cochlea or administered by transtympanic injection or via a transtympanic device including a canula or an implant. Methods include sustained delivery and controlled delivery for local or systemic delivery including delivery of inhibitors using, for example, a pump, a slow or sustained release composition or an implant comprising a drug depot.

In preferred embodiments of the compositions, combinations, methods, commercial packages and kits provided herein, each inhibitor comprises a separate nucleic acid molecule, or a pharmaceutically acceptable salt thereof. In some embodiments of the compositions, combinations, methods, commercial packages and kits provided herein, the nucleic acid molecules are linked one to the other. In some embodiments of the compositions, combinations, methods, commercial packages and kits provided herein, the nucleic acid molecules are annealed and covalently linked in a multi-arm formation (RNAistar).

In preferred embodiments of the compositions, combinations, methods, commercial packages and kits provided herein, each inhibitor comprises a nucleic acid compound. Preferably, the nucleic acid compound is applied directly to the round window membrane of the cochlea or administered by transtympanic injection or via a transtympanic device including a canula.

Thus, the compositions, combinations, methods, commercial packages and kits provided herein preferably involve use of nucleic acid molecules (for example, short interfering nucleic acid (siNA), short interfering RNA (siRNA), double-stranded RNA (dsRNA), micro-RNA (miRNA) or short hairpin RNA (shRNA)) that bind a nucleotide sequence (such as an mRNA sequence) or portion thereof, encoding HES1, HES5, HEY2, CDKN1B, or NOTCH1, for example, the mRNA coding sequence (SEQ ID NOS:1, 2, 10, 7, and 11) for human HES1, HES5, HEY2, CDKN1B, or NOTCH1 mRNA, respectively, encoding one or more proteins or protein subunits exemplified by SEQ ID NOS:12, 13, 21, 18 and 22, respectively. In certain preferred embodiments, the compositions, combinations, methods, commercial packages and kits disclosed herein down-regulate or inhibit expression of HES1, HES5 and HEY2, or CDKN1B, NOTCH1, and HEY2 genes. In various embodiments each nucleic acid molecule is selected from the group consisting of unmodified or chemically modified dsRNA compound such as a chemically modified siRNA or shRNA that down-regulates HES1, HES5, HEY2, CDKN1B or NOTCH1, expression.

In some preferred embodiments the HES1 inhibitor is a synthetic, chemically modified double stranded RNA (dsRNA) compound that down-regulates HES1 expression. In certain preferred embodiments, "HES1" refers to human HES1 gene. In some preferred embodiments the HES5 inhibitor is a synthetic, chemically modified double stranded RNA (dsRNA) compound that down-regulates HES5 expression. In certain preferred embodiments, "HES5" refers to human HES5 gene. In some preferred embodiments the HEY2 inhibitor is a synthetic, chemically modified double stranded RNA (dsRNA) compound that down-regulates HEY2 expression. In certain preferred embodiments, "HEY2" refers to human HEY2 gene. In some preferred embodiments the CDKN1B inhibitor is a synthetic, chemically modified double stranded RNA (dsRNA) compound that down-regulates CDKN1B expression. In certain preferred embodiments, "CDKN1B" refers to human CDKN1B gene. In some preferred embodiments the NOTCH1 inhibitor is a synthetic, chemically modified double stranded RNA (dsRNA) compound that down-regulates NOTCH1 expression. In certain preferred embodiments, "NOTCH1" refers to human NOTCH1 gene.

In some preferred embodiments of the compositions, combinations, methods, commercial packages and kits provided herein, the first nucleic acid molecule is a double-stranded oligonucleotide that binds a nucleotide sequence encoding a HES1 gene, the second nucleic acid molecule is a double-stranded oligonucleotide that binds a nucleotide sequence encoding a HES5 gene, and the third nucleic acid molecule is a double-stranded oligonucleotide that binds a nucleotide sequence encoding a HEY2 gene.

In some preferred embodiments of the compositions, combinations, methods, commercial packages and kits provided herein, the first nucleic acid molecule is a double-stranded oligonucleotide that binds a nucleotide sequence encoding a CDKN1B gene, the second nucleic acid molecule is a double-stranded oligonucleotide that binds a nucleotide sequence encoding a NOTCH1 gene, and the third nucleic acid molecule is a double-stranded oligonucleotide that binds a nucleotide sequence encoding a HEY2 gene.

In various preferred embodiments of the compositions, combinations, methods, commercial packages and kits provided herein, each of the double-stranded oligonucleotides (for example double-stranded RNA (dsRNA)) comprises a sense strand and an antisense strand.

In some preferred embodiments of the compositions, combinations, methods, commercial packages and kits provided herein, each of the double-stranded oligonucleotides comprises a sense strand and an antisense strand, wherein (a) each strand is independently 18 to 49 nucleotides in length; (b) a 18 to 49 nucleotide sequence of the antisense strand is complementary to a sequence of an mRNA encoding a target gene; and (c) a 18 to 49 nucleotide sequence of the sense strand is complementary to the antisense strand. In various embodiment the mRNA encoding a target gene is selected from mammalian HES1 (SEQ ID NO:1), HES5 (SEQ ID NO:2), HEY2 (SEQ ID NO:10), CDKN1B (SEQ ID NO:7), or NOTCH1 (e.g., SEQ ID NO:11 or portion thereof; and the sense strand and the antisense strand comprise sequence pairs set forth in any of SEQ ID NOS:23-1495 or 26667-26706 (HES1), SEQ ID NOS:1496-2703 or 26707-26732 (HES5), SEQ ID NOS:13004-16621 or 26779-26788 (HEY2), SEQ ID NOS:7444-10533 or 26867-26900 (CDKN1B) or SEQ ID NOS:16622-26666 or 26901-26912 (NOTCH1).

In some preferred embodiments of the compositions, combinations, methods, commercial packages and kits provided herein, a first double-stranded oligonucleotide comprises a sense strand and an antisense strand, wherein;
(a) each strand is independently 18 to 49 nucleotides in length;
(b) a 18 to 49 nucleotide sequence of the antisense strand is complementary to a sequence of an mRNA encoding HES1; and
(c) a 18 to 49 nucleotide sequence of the sense strand is complementary to the antisense strand;
a second double-stranded oligonucleotide comprises a sense strand and an antisense strand, wherein;
(a) each strand is independently 18 to 49 nucleotides in length;
(b) a 18 to 49 nucleotide sequence of the antisense strand is complementary to a sequence of an mRNA encoding HES5; and
(c) a 18 to 49 nucleotide sequence of the sense strand is complementary to the antisense strand; and
a third double-stranded oligonucleotide comprises a sense strand and an antisense strand, wherein;
(a) each strand is independently 18 to 49 nucleotides in length;
(b) a 18 to 49 nucleotide sequence of the antisense strand is complementary to a sequence of an mRNA encoding HEY2; and
(c) a 18 to 49 nucleotide sequence of the sense strand is complementary to the antisense strand.

In other preferred embodiments of the compositions, combinations, methods, commercial packages and kits provided herein, a first double-stranded oligonucleotide is a dsRNA molecule comprising a sense strand and an antisense strand, wherein;
(a) each strand is independently 18 to 49 nucleotides in length;
(b) a 18 to 49 nucleotide sequence of the antisense strand is complementary to a sequence of an mRNA encoding CDKN1B; and
(c) a 18 to 49 nucleotide sequence of the sense strand is complementary to the antisense strand; a second double-stranded oligonucleotide comprises a sense strand and an antisense strand, wherein;
(a) each strand is independently 18 to 49 nucleotides in length;
(b) a 18 to 49 nucleotide sequence of the antisense strand is complementary to a sequence of an mRNA encoding NOTCH1; and
(c) a 18 to 49 nucleotide sequence of the sense strand is complementary to the antisense strand; and
a third double-stranded oligonucleotide comprises a sense strand and an antisense strand, wherein;
(a) each strand is independently 18 to 49 nucleotides in length;
(b) a 18 to 49 nucleotide sequence of the antisense strand is complementary to a sequence of an mRNA encoding HEY2; and
(c) a 18 to 49 nucleotide sequence of the sense strand is complementary to the antisense strand.

In some embodiments the dsRNA molecule has a structure set forth as Structure (A1) or Structure (A2), disclosed herein.

In particular embodiments, compositions, combinations, methods, commercial packages and kits provided herein are useful in the treatment of an ear (otic, aural) condition or pathology, particularly pathologies involving death of otic (sensory) hair cells if the inner ear, are provided herein.

In another aspect provided is use of a combination of a HES1 inhibitor, a HES5 inhibitor and a HEY2 inhibitor, for the preparation of a medicament for the treatment of a disease or disorder of the inner ear or of the middle ear. In another aspect provided is use of a combination of a CDKN1B inhibitor, a NOTCH1 inhibitor and a HEY2 inhibitor, for the preparation of a medicament for the treatment of a disease or disorder of the inner ear or of the middle ear.

In particular embodiments, provided herein are combinations, compositions and methods of use thereof in the treatment of auditory and vestibular diseases, disorders, injuries and conditions including, without being limited to ototoxin induced hearing loss, age-related hearing loss, a hearing impairment due to end-organ lesions involving inner ear hair cells, e.g., acoustic trauma, viral endolymphatic labyrinthitis, Meniere's disease; tinnitus which may be intermittent or continuous, wherein there is diagnosed a sensorineural loss; hearing loss due to bacterial or viral infection, such as in herpes zoster oticus; purulent labyrinthitis arising from acute otitis media, purulent meningitis, chronic otitis media, sudden deafness including that of viral origin, e.g., viral endolymphatic labyrinthitis caused by viruses including mumps, measles, influenza, chicken pox, mononucleosis and adenoviruses; congenital hearing loss such as that caused by rubella, anoxia during birth, bleeding into the inner ear due to trauma during delivery, ototoxic drugs administered to the mother, erythroblastosis fetalis, and hereditary conditions including Waardenburg's syndrome and Hurler's syndrome.

In another aspect provided herein is a commercial package or a kit comprising any of the composition or the combination disclosed herein. In some embodiments, the commercial package or kit, includes a label or package insert that provides certain information about how the composition or combination disclosed herein may be used. In some embodiments of the commercial package or kit, the label or package insert includes dosing information. In some embodiments of the commercial package or kit, the label or package insert includes indications for use. In some embodiments of the commercial package or kit, the label or package insert indicates that the composition or the combination is suitable for use in therapy. In some embodiments of the commercial package or kit, wherein the label or package insert indicates that the composition or the combination is suitable for use in preventing, treating, or delaying of progression of a hearing disorder, a hearing loss, and/or a balance impairment, or for preventing the loss of otic (sensory) hair cells of the inner ear in a subject.

The preferred methods, materials, and examples that will now be described are illustrative only and are not intended to be limiting; materials and methods similar or equivalent to those described herein can be used in practice or testing of the invention. Other features and advantages of the invention will be apparent from the following figures, detailed description, and from the claims.

BRIEF DESCRIPTION OF THE FIGURES

FIG. 1A shows the ABR response obtained in this study at Day 0, after 3 weeks, after 5 weeks, after 7 weeks and after 9 weeks for 1 KHz stimulus.

FIG. 1B shows the ABR response obtained in this study at Day 0, after 3 weeks, after 5 weeks, after 7 weeks and after 9 weeks for 4 KHz stimulus.

FIG. 1C shows the ABR response obtained in this study at Day 0, after 3 weeks, after 5 weeks, after 7 weeks and after 9 weeks for 8 KHz stimulus.

FIG. 1D shows the ABR response obtained in this study at Day 0, after 3 weeks, after 5 weeks, after 7 weeks and after 9 weeks for 16 KHz stimulus.

FIG. 1E shows the ABR response obtained in this study at Day 0, after 3 weeks, after 5 weeks, after 7 weeks and after 9 weeks for 32 KHz stimulus.

DETAILED DESCRIPTION OF THE INVENTION

Figure 1A:
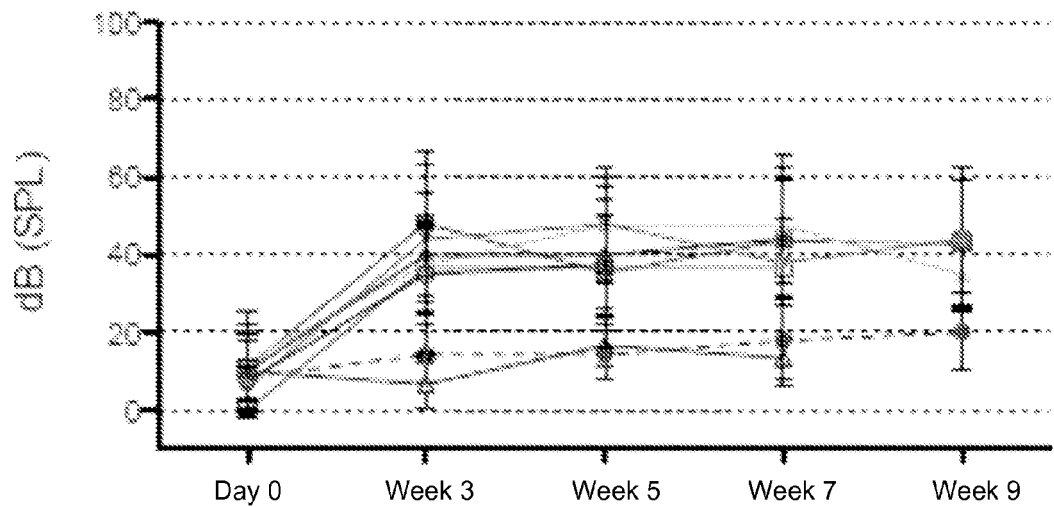
FIGS. 1A-1E show the ABR response obtained in this study at Day 0, after 3 weeks, after 5 weeks, after 7 weeks and after 9 weeks.

Provided herein are compositions and combinations which down-regulate expression of certain genes associated with hearing loss and their use in treating a subject suffering from hearing loss and/or balance impairment, for promoting the replacement, regeneration, or protection of otic (sensory) hair cells of the inner ear, and or effecting hearing restoration/regeneration. In preferred embodiments the methods comprise partial or full hearing regeneration. Inhibition of expression of a combination of the HES1, HES5 and HEY2 genes, or of a combination of the CDKN1B, NOTCH1 and HEY2 genes was shown to be beneficial in regeneration of hearing. The present application relates in particular to use of therapeutic agents, for example double-stranded oligonucleotide molecules, including dsRNA/small interfering RNA (siRNA) compounds which inhibit expression of HES1, HES5, CDKN1B, HEY2 and NOTCH1 and to the use of these dsRNA molecules in the treatment of hearing loss. Sense strands and complementary antisense strands useful in generating the compositions and the combinations of dsRNA molecules as provided herein are set forth in SEQ ID NOS:23-1495 or 26667-26706 (HES1), SEQ ID NOS: 1496-2703 or 26707-26732 (HES5), SEQ ID NOS:13004-16621 or 26779-26788 (HEY2), SEQ ID NOS:7444-10533 or 26867-26900 (CDKN1B) or SEQ ID NOS:16622-26666 or 26901-26912 (NOTCH1). Certain currently preferred sense strand and antisense strand pairs are set forth in tables I-V infra.

Provided herein are methods, combinations and compositions for inhibiting expression of HES1, HES5 and HEY2 genes, or for inhibiting expression of CDKN1B, NOTCH1 and HEY2 genes in vivo. In general, the method includes administering oligoribonucleotide combination/composition, such as combination/composition of dsRNA molecules, including small interfering RNAs (i.e., dsRNAs), that are targeted to the target mRNAs, and hybridize to, or interact with, the mRNAs under biological conditions (within the cell), or a nucleic acid material that can produce siRNAs in a cell, in an amount sufficient to down-regulate expression of a target gene by an RNA interference mechanism. Details of target genes are presented in Table A, hereinbelow.

TABLE A

Target genes

| No. | Gene abbrev | Full name and gi and accession numbers |
|---|---|---|
| 1 | HES1 | hairy and enhancer of split 1, (*Drosophila*) Alternative Names: bHLHb39; FLJ20408; HES-1; HHL; HRY gi|8400709|ref|NM_005524.2|(SEQ ID NO: 1) |
| 2 | HES5 | hairy and enhancer of split 5 (*Drosophila*) Alternative Names: bHLHb 38gi|145301612|ref|NM_001010926.2|(SEQ ID NO: 2) |
| 3 | ID1 | inhibitor of DNA binding 1, dominant negative HLH protein. Alternative Names: bHLHb24; ID gi|31317298|ref|NM_002165.2|transcript v.1 (SEQ ID NO: 3) gi|31317296|ref|NM_181353.1|transcript v.2 (SEQ ID NO: 4) |

TABLE A-continued

Target genes

| No. | Gene abbrev | Full name and gi and accession numbers |
|---|---|---|
| 4 | ID2 | inhibitor of DNA binding 2, dominant negative HLH protein Alternative Names: bHLHb26; GIG8; ID2A; ID2H; MGC26389 gi|33946335|ref|NM_002166.4|(SEQ ID NO: 5) |
| 5 | ID3 | inhibitor of DNA binding 3, dominant negative HLH protein. Alternative Names: bHLHb25; HEIR-1 gi|156119620|ref|NM_002167.3|(SEQ ID NO: 6) |
| 6 | CDKN1B | cyclin-dependent kinase inhibitor 1B (p27, Kip1) Alternative Names: CDKN4; KIP1; MEN1B; MEN4; P27KIP1 gi|17978497|ref|NM_004064.2|(SEQ ID NO: 7) |
| 7 | HEY1 | HEY1—hairy/enhancer-of-split related with YRPW motif 1 gi|105990527|ref|NM_012258.3|transcript v.1 (SEQ ID NO: 8) gi|105990525|ref|NM_001040708.1|transcript v.2 (SEQ IDNO: 9) |
| 8 | HEY2 | HEY2—hairy/enhancer-of-split related with YRPW motif 2 gi|105990529|ref|NM_012259.2|(SEQ ID NO: 10) |
| 9 | NOTCH1 | NOTCH1 Notch homolog 1, translocation-associated (*Drosophila*) gi|148833507|ref|NM_017617.3|*Homo sapiens* mRNA (SEQ ID NO: 11) |

Preferred targets are HES1 (mRNA SEQ ID NO:1; polypeptide SEQ ID NO:12), HES5 (mRNA SEQ ID NO:2; polypeptide SEQ ID NO:13), HEY2 (mRNA SEQ ID NO:10; polypeptide SEQ ID NO:21); CDKN1B (mRNA SEQ ID NO:7; polypeptide SEQ ID NO:18) and NOTCH1 (mRNA SEQ ID NO:11; polypeptide SEQ ID NO:22).

In various embodiments, provided is the use of compositions/combinations of double stranded RNAs, (dsRNAs) including chemically modified small interfering RNAs (siRNAs), in the treatment of various diseases and medical conditions. Particular diseases and conditions to be treated are related to hearing loss and/or balance loss.

Preferred sense and antisense nucleic acid sequences useful in generating dsRNA for use in the combinations, compositions and methods as provided herein were prioritized based on their score according to a proprietary algorithm as the best sequences for targeting the human gene expression. SEQ ID NOS:23-693 and 26691-26706 (HES1); SEQ ID NOS:1496-2029 and 26725-26732 (HES5); SEQ ID NOS:7444-9007 and 26887-26900 (CDKN1B); SEQ ID NOS:13004-14801 and 26785-26788 (HEY2); SEQ ID NOS:16622-18643 and 26922-26912 (NOTCH1) set forth 19-mer oligomers. SEQ ID NOS:694-1495 (HES1); SEQ ID NOS:2030-2703 (HES5); SEQ ID NOS:9008-10533 (CDKN1B); SEQ ID NOS:14802-16389 (HEY2); SEQ ID NOS:18644-26666 (NOTCH1) set forth 18-mer oligomers useful in generating dsRNA molecules according to Structure A2, as described hereinbelow.

DEFINITIONS

For convenience certain terms employed in the specification, examples and claims are described herein.

It is to be noted that, as used herein, the singular forms "a", "an" and "the" include plural forms unless the content clearly dictates otherwise.

Where aspects or embodiments of the invention are described in terms of Markush groups or other grouping of alternatives, those skilled in the art will recognize that the invention is also thereby described in terms of any individual member or subgroup of members of the group.

An "inhibitor" is a compound, which is capable of reducing (partially or fully) the expression of a gene or the activity of the product of such gene to an extent sufficient to achieve a desired biological or physiological effect. The term "inhibitor" as used herein refers to one or more of a small organic molecule, a protein, an antibody or fragments thereof, a peptide, a peptidomimetic and a nucleic acid molecule, including siRNA, shRNA, synthetic shRNA; miRNA, antisense RNA and DNA and ribozymes.

A "dsRNA molecule" or "dsRNA inhibitor" is a compound which is capable of down-regulating or reducing the expression of a gene or the activity of the product of such gene to an extent sufficient to achieve a desired biological or physiological effect and includes one or more of a siRNA, shRNA, synthetic shRNA; miRNA. Inhibition may also be referred to as down-regulation or, for RNAi, silencing.

The term "inhibit" as used herein refers to reducing the expression of a gene or the activity of the product of such gene to an extent sufficient to achieve a desired biological or physiological effect. Inhibition is either complete or partial.

As used herein, the term "inhibition" of a target gene means attenuation, reduction or down regulation of gene expression (transcription or translation) or polypeptide activity of a target gene wherein the target gene is selected from a gene transcribed into an mRNA set forth in any one of SEQ ID NOS:1, 2, 10, 7, or 11 or an SNP (single nucleotide polymorphism) or other variants thereof. The gi number for the mRNA of each target gene is set forth in Table A ("v" refers to transcript variant). The polynucleotide sequence of the target mRNA sequence, or the target gene having a mRNA sequence refer to the mRNA sequences set forth in SEQ ID NO:1, 2, 10, 7 or 11, or any homologous sequences thereof preferably having at least 70% identity, more preferably 80% identity, even more preferably 90% or 95% identity to any one of mRNA set forth in SEQ ID NO:1, 2, 10, 7 or 11. Therefore, polynucleotide sequences derived from any one of SEQ ID NO:1, 2, 10, 7 or 11 which have undergone mutations, alterations or modifications as described herein are encompassed in the present invention. The terms "mRNA polynucleotide sequence", "mRNA sequence" and "mRNA" are used interchangeably.

As used herein, the terms "polynucleotide" and "nucleic acid" may be used interchangeably and refer to nucleotide sequences comprising deoxyribonucleic acid (DNA), and ribonucleic acid (RNA). The terms are to be understood to include, as equivalents, analogs of either RNA or DNA made from nucleotide analogs. Throughout this application, mRNA sequences are set forth as representing the corresponding genes.

"Oligonucleotide" or "oligomer" refers to a deoxyribonucleotide or ribonucleotide sequence from about 2 to about 50 nucleotides. Each DNA or RNA nucleotide may be independently natural or synthetic, and or modified or unmodified. Modifications include changes to the sugar moiety, the base moiety and or the linkages between nucleotides in the oligonucleotide. The compounds according to various aspect and embodiments of the present disclosure encompass molecules comprising deoxyribonucleotides, ribonucleotides, modified deoxyribonucleotides, modified ribonucleotides, unconventional moieties and combinations thereof.

"Substantially complementary" refers to complementarity of greater than about 84%, to another sequence. For example in a duplex region consisting of 19 base pairs one mismatch results in 94.7% complementarity, two mismatches results in about 89.5% complementarity and 3 mismatches results in about 84.2% complementarity, rendering the duplex region substantially complementary. Accordingly substantially identical refers to identity of greater than about 84%, to another sequence.

"Nucleotide" is meant to encompass deoxyribonucleotides and ribonucleotides, which may be natural or synthetic, and or modified or unmodified. Modifications include changes to the sugar moiety, the base moiety and or the linkages between ribonucleotides in the oligoribonucleotide. As used herein, the term "ribonucleotide" encompasses natural and synthetic, unmodified and modified ribonucleotides. Modifications include changes to the sugar moiety, to the base moiety and/or to the linkages between ribonucleotides in the oligonucleotide.

The nucleotides can be selected from naturally occurring or synthetic modified bases. Naturally occurring bases include adenine, guanine, cytosine, thymine and uracil. Modified bases of nucleotides include inosine, xanthine, hypoxanthine, 2-aminoadenine, 6-methyl, 2-propyl and other alkyl adenines, 5-halo uracil, 5-halo cytosine, 6-aza cytosine and 6-aza thymine, pseudo uracil, 4-thiouracil, 8-halo adenine, 8-aminoadenine, 8-thiol adenine, 8-thiolkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine. In some embodiments one or more nucleotides in an oligomer is substituted with inosine.

According to some embodiments the present disclosure provides use of inhibitory oligonucleotide compounds comprising unmodified and modified nucleotides and or unconventional moieties. The compounds comprise at least one modified nucleotide selected from the group consisting of a sugar modification, a base modification and an internucleotide linkage modification and may contain DNA, and modified nucleotides such as LNA (locked nucleic acid), ENA (ethylene-bridged nucleic acid), PNA (peptide nucleic acid), arabinoside, phosphonocarboxylate or phosphinocarboxylate nucleotide (PACE nucleotide), mirror nucleotide, or nucleotides with a 6 carbon sugar.

All analogs of, or modifications to, a nucleotide/oligonucleotide are employed with the present embodiments, provided that said analog or modification does not substantially adversely affect the function of the nucleotide/oligonucleotide. Acceptable modifications include modifications of the sugar moiety, modifications of the base moiety, modifications in the internucleotide linkages and combinations thereof.

A sugar modification includes a modification on the 2' moiety of the sugar residue and encompasses amino, fluoro, alkoxy e.g. methoxy, alkyl, amino, fluoro, chloro, bromo, CN, CF, imidazole, carboxylate, thioate, $C_1$ to $C_{10}$ lower alkyl, substituted lower alkyl, alkaryl or aralkyl, $OCF_3$, OCN, O—, S—, or N— alkyl; O-, S, or N-alkenyl; $SOCH_3$; $SO_2CH_3$; $ONO_2$; $NO_2$, $N_3$; heterozycloalkyl; heterozycloalkaryl; aminoalkylamino; polyalkylamino or substituted silyl, as, among others, described in European patents EP 0 586 520 B1 or EP 0 618 925 B1.

In one embodiment a dsRNA molecule useful in methods, compositions, combinations, commercial packages and kits provided herein, comprises at least one ribonucleotide comprising a 2' modification on the sugar moiety ("2' sugar modification"). In certain embodiments the compound comprises 2'O-alkyl or 2'-fluoro or 2'O-allyl or any other 2' modification, optionally on alternate positions. Other stabilizing modifications are also possible (e.g. terminal modifications). In some embodiments a preferred 2'O-alkyl is 2'O-methyl (methoxy) sugar modification.

In some embodiments the backbone of the oligonucleotides is modified and comprises phosphate-D-ribose entities but may also contain thiophosphate-D-ribose entities, triester, thioate, 2'-5' bridged backbone (also may be referred to as 5'-2'), PACE and the like.

As used herein, the terms "non-pairing nucleotide analog" means a nucleotide analog which comprises a non-base pairing moiety including but not limited to: 6 des amino adenosine (Nebularine), 4-Me-indole, 3-nitropyrrole, 5-nitroindole, Ds, Pa, N3-Me ribo U, N3-Me riboT, N3-Me dC, N3-Me-dT, N1-Me-dG, N1-Me-dA, N3-ethyl-dC, N3-Me dC. In some embodiments the non-base pairing nucleotide analog is a ribonucleotide. In other embodiments it is a deoxyribonucleotide. In addition, analogues of polynucleotides may be prepared wherein the structure of one or more nucleotide is fundamentally altered and better suited as therapeutic or experimental reagents. An example of a nucleotide analogue is a peptide nucleic acid (PNA) wherein the deoxyribose (or ribose) phosphate backbone in DNA (or RNA) is replaced with a polyamide backbone which is similar to that found in peptides. PNA analogues have been shown to be resistant to enzymatic degradation and to have extended stability in vivo and in vitro. Other modifications that can be made to oligonucleotides include polymer backbones, cyclic backbones, acyclic backbones, thiophosphate-D-ribose backbones, triester backbones, thioate backbones, 2'-5' bridged backbone, artificial nucleic acids, morpholino nucleic acids, glycol nucleic acid (GNA), threose nucleic acid (TNA), arabinoside, and mirror nucleoside (for example, beta-L-deoxyribonucleoside instead of beta-D-deoxyribonucleoside). Examples of dsRNA molecules comprising LNA nucleotides are disclosed in Elmen et al., (NAR 2005, 33(1):439-447). The compounds useful in accordance with the present disclosure can be synthesized using one or more inverted nucleotides, for example inverted thymidine or inverted adenine (see, for example, Takei, et al., 2002, JBC 277(26):23800-06).

Other modifications include terminal modifications on the 5' and/or 3' part of the oligonucleotides and are also known as capping moieties. Such terminal modifications are selected from a nucleotide, a modified nucleotide, a lipid, a peptide, a sugar and inverted abasic moiety.

An "alkyl moiety or derivative thereof" refers to straight chain or branched carbon moieties and moieties per se or further comprising a functional group including alcohols, phosphodiester, phosphorothioate, phosphonoacetate and also includes amines, carboxylic acids, esters, amides aldehydes. "Hydrocarbon moiety" and "alkyl moiety" are used interchangeably.

"Terminal functional group" includes halogen, alcohol, amine, carboxylic, ester, amide, aldehyde, ketone, ether groups.

Provided are methods, compositions and combinations for inhibiting expression of target genes in vivo. In certain embodiments, the methods include administering a composition or a combination of oligoribonucleotides, in particular small interfering RNAs (i.e. siRNAs) that target mRNAs transcribed from target genes in an amount sufficient to down-regulate expression of target genes by, e.g. an RNA interference mechanism. In particular, the subject methods can be used to inhibit expression of target genes for treatment of a disease. Provided herein are compositions and combinations of dsRNA molecules directed to target genes disclosed herein and useful as therapeutic agents to treat various otic and vestibular system pathologies.

Provided are methods, combinations and compositions for inhibiting expression of a hearing loss-associated gene in vivo. In general, the methods includes administering combinations of oligoribonucleotides, in particular double-stranded RNAs (such as, for example, siRNAs), that target mRNAs, or pharmaceutical compositions comprising them, in an amount sufficient to down-regulate expression of target genes by, e.g. an RNA interference mechanism. In particular, the subject methods can be used to inhibit expression of a hearing loss-associated genes for treatment of a disease or a disorder or a condition disclosed herein.

Provided herein are methods, combinations and compositions for inhibiting expression of HES1, HES5 and HEY2, in vivo. Provided herein are methods and compositions for inhibiting expression of HEY2, CDKN1B and NOTCH1, in vivo. In general, the methods includes administering oligoribonucleotides, in particular double stranded RNAs (i.e. dsRNAs) or a nucleic acid material that can produce dsRNA in a cell, that target mRNAs transcribed from HES1, HES5 and HEY2 genes or HEY2, CDKN1B and NOTCH1 genes in an amount sufficient to down-regulate expression of the target genes e.g., by an RNA interference mechanism.

dsRNA and RNA Interference

RNA interference (RNAi) is a phenomenon involving double-stranded (ds) RNA-dependent gene-specific post-transcriptional silencing. Initial attempts to study this phenomenon and to manipulate mammalian cells experimentally were frustrated by an active, non-specific antiviral defense mechanism which was activated in response to long dsRNA molecules (Gil et al., Apoptosis, 2000. 5:107-114). Later, it was discovered that synthetic duplexes of 21 nucleotide RNAs could mediate gene specific RNAi in mammalian cells, without stimulating the generic antiviral defense mechanisms Elbashir et al. Nature 2001, 411:494-498 and Caplen et al. PNAS 2001, 98:9742-9747). As a result, small interfering RNAs (siRNAs), which are short double-stranded RNAs, have been widely used to inhibit gene expression and understand gene function.

RNA interference (RNAi) is mediated by small interfering RNAs (siRNAs) (Fire et al, Nature 1998, 391:806) or microRNAs (miRNAs) (Ambros V. Nature 2004, 431:350-355); and Bartel D P. Cell. 2004 116(2):281-97). The corresponding process is commonly referred to as specific post-transcriptional gene silencing when observed in plants and as quelling when observed in fungi.

A siRNA compound is a double-stranded RNA which down-regulates or silences (i.e. fully or partially inhibits) the expression of an endogenous or exogenous gene/mRNA.

RNA interference is based on the ability of certain dsRNA species to enter a specific protein complex, where they are then targeted to complementary cellular RNAs and specifically degrades them. Thus, the RNA interference response features an endonuclease complex containing a siRNA, commonly referred to as an RNA-induced silencing complex (RISC), which mediates cleavage of single-stranded RNA having a sequence complementary to the antisense strand of the siRNA duplex. Cleavage of the target RNA may take place in the middle of the region complementary to the antisense strand of the siRNA duplex (Elbashir, et al., Genes Dev., 2001, 15:188). In more detail, longer dsRNAs are digested into short (17-29 bp) dsRNA fragments (also referred to as short inhibitory RNAs or "siRNAs") by type III RNAses (DICER, DROSHA, etc., (see Bernstein et al., Nature, 2001, 409:363-6 and Lee et al., Nature, 2003, 425:415-9). The RISC protein complex recognizes these fragments and complementary mRNA. The whole process is culminated by endonuclease cleavage of target mRNA (McManus and Sharp, Nature Rev Genet, 2002, 3:737-47; Paddison and Hannon, Curr Opin Mol Ther. 2003, 5(3): 217-24). (For additional information on these terms and proposed mechanisms, see for example, Bernstein, et al., RNA. 2001, 7(11):1509-21; Nishikura, Cell. 2001, 107(4): 415-8 and PCT Publication No. WO 01/36646).

The selection and synthesis of dsRNA compounds corresponding to known genes has been widely reported; see for example Ui-Tei et al., J Biomed Biotechnol. 2006; 65052; Chalk et al., BBRC. 2004, 319(1):264-74; Sioud and Leirdal, Met. Mol. Biol.; 2004, 252:457-69; Levenkova et al., Bioinform. 2004, 20(3):430-2; Ui-Tei et al., NAR 2004, 32(3):936-48. For examples of the use of, and production of, modified siRNA see Braasch et al., Biochem., 2003, 42(26): 7967-75; Chiu et al., RNA, 2003, 9(9):1034-48; PCT publications WO 2004/015107 (atugen); WO 02/44321 (Tuschl et al), and U.S. Pat. Nos. 5,898,031 and 6,107,094.

Several groups have described the development of DNA-based vectors capable of generating siRNA within cells. The method generally involves transcription of short hairpin RNAs that are efficiently processed to form siRNAs within cells (Paddison et al. PNAS USA 2002, 99:1443-1448; Paddison et al. Genes & Dev 2002, 16:948-958; Sui et al. PNAS USA 2002, 8:5515-5520; and Brummelkamp et al. Science 2002, 296:550-553). These reports describe methods of generating siRNAs capable of specifically targeting numerous endogenously and exogenously expressed genes.

Studies have revealed that siRNA can be effective in vivo in mammals, including humans. Specifically, Bitko et al., showed that specific siRNAs directed against the respiratory syncytial virus (RSV) nucleocapsid N gene are effective in treating mice when administered intranasally (Nat. Med. 2005, 11(1):50-55). For reviews of therapeutic applications of siRNAs see for example Barik (Mol. Med. 2005, 83: 764-773) and Chakraborty (Current Drug Targets 2007 8(3):469-82). In addition, clinical studies with short siRNAs that target the VEGFR1 receptor in order to treat age-related macular degeneration (AMD) have been conducted in human patients (Kaiser, Am J Ophthalmol. 2006 142(4): 660-8). Further information on the use of siRNA as therapeutic agents may be found in Durcan, 2008. Mol. Pharma. 5(4):559-566; Kim and Rossi, 2008. BioTechniques 44:613-616; Grimm and Kay, 2007, JCI, 117(12):3633-41.

A dsRNA useful with the combination therapy or compositions is a duplex oligoribonucleotide in which the sense strand is substantially complementary to an 18-40 consecutive nucleotide segment of the mRNA polynucleotide sequence of a target gene, and the antisense strand is substantially complementary to the sense strand. In general, some deviation from the target mRNA sequence is tolerated without compromising the siRNA activity (see e.g. Czauderna et al., Nuc. Acids Res. 2003, 31(11):2705-2716). A siRNA of the invention inhibits gene expression on a post-transcriptional level with or without destroying the mRNA. Without being bound by theory, siRNA may target the mRNA for specific cleavage and degradation and/or may inhibit translation from the targeted message.

In some embodiments the dsRNA is blunt ended, on one or both ends. More specifically, the dsRNA may be blunt ended on the end defined by the 5'-terminus of the first strand and the 3'-terminus of the second strand, or the end defined by the 3'-terminus of the first strand and the 5'-terminus of the second strand.

In other embodiments at least one of the two strands may have an overhang of at least one nucleotide at the 5'-terminus; the overhang may consist of at least one deoxyribonucleotide. At least one of the strands may also optionally have an overhang of at least one nucleotide at the 3'-terminus. The overhang may consist of from about 1 to about 5 nucleotides.

The length of RNA duplex is from about 18 to about 49 ribonucleotides, preferably 19 to 23 ribonucleotides. Further, the length of each strand (oligomer) may independently have a length selected from the group consisting of about 18 to about 49 bases, preferably 18 to 23 bases and more preferably 19, 20 or 21 ribonucleotides.

Additionally, in certain preferred embodiments the complementarity between said first strand and the target nucleic acid is perfect. In some embodiments, the strands are substantially complementary, i.e. having one, two or up to three mismatches between said first strand and the target nucleic acid.

Further, the 5'-terminus of the first strand of the siRNA may be linked to the 3'-terminus of the second strand, or the 3'-terminus of the first strand may be linked to the 5'-terminus of the second strand, said linkage being via a nucleic acid linker typically having a length between 3-100 nucleotides, preferably about 3 to about 10 nucleotides.

The dsRNAs compounds useful in methods, combinations and compositions disclosed herein, possess structures and modifications which impart one or more of increased activity, increased stability, reduced toxicity, reduced off target effect, and/or reduced immune response. The siRNA structures as disclosed herein, are beneficially applied to double-stranded RNA useful in methods, combinations and compositions disclosed herein for use in preventing or attenuation target gene expression, in particular the target genes discussed herein.

According to one aspect, the present disclosure provides use of combinations or compositions of chemically modified double-stranded oligonucleotides comprising at least one modified nucleotide selected from the group consisting of a sugar modification, a base modification and an internucleotide linkage modification. Accordingly, the chemically modified double stranded oligonucleotide compounds useful in the methods, compositions and combinations provided herein, may contain modified nucleotides such as DNA, LNA (locked nucleic acid), ENA (ethylene-bridged nucleic acid), PNA (peptide nucleic acid), arabinoside, PACE, mirror nucleoside, or nucleotides with a 6 carbon sugar. Examples of PACE nucleotides and analogs are disclosed in U.S. Pat. Nos. 6,693,187 and 7,067,641 both incorporated herein by reference. The oligonucleotide may further comprise 2'O-methyl or 2'-fluoro or 2'O-allyl or any other 2' modification, optionally on alternate positions. Other stabilizing modifications, which do not significantly reduce the activity are also possible (e.g. terminal modifications). The backbone of the active part of the oligonucleotides may comprise phosphate-D-ribose entities but may also contain thiophosphate-D-ribose entities, triester, thioate, 2'-5' bridged backbone (also may be referred to as 5'-2'), PACE or any other type of modification. Terminal modifications on the 5' and/or 3' part of the oligonucleotides are also possible. Such terminal modifications may be lipids, peptides, sugars, inverted abasic moieties or other molecules.

Chemical Synthesis of Oligonucleotide Compounds

The oligonucleotide compounds for use in the methods, compositions, combinations, commercial packages and kits disclosed herein can be synthesized by any of the methods that are well-known in the art for synthesis of ribonucleic (or deoxyribonucleic) oligonucleotides. Such synthesis is, among others, described in Beaucage and Iyer, Tetrahedron 1992; 48:2223-2311; Beaucage and Iyer, Tetrahedron 1993; 49: 6123-6194 and Caruthers, et. al., Methods Enzymol. 1987; 154: 287-313; the synthesis of thioates is, among others, described in Eckstein, Annu. Rev. Biochem. 1985; 54: 367-402, the synthesis of RNA molecules is described in Sproat, in Humana Press 2005 edited by Herdewijn P.; Kap. 2: 17-31 and respective downstream processes are, among others, described in Pingoud et. al., in IRL Press 1989 edited by Oliver R. W. A.; Kap. 7: 183-208.

Other synthetic procedures are known in the art e.g. the procedures as described in Usman et al., 1987, J. Am. Chem. Soc., 109, 7845; Scaringe et al., 1990, NAR., 18, 5433; Wincott et al., 1995, NAR. 23, 2677-2684; and Wincott et al., 1997, Methods Mol. Bio., 74, 59, and these procedures may make use of common nucleic acid protecting and coupling groups, such as dimethoxytrityl at the 5'-end, and phosphoramidites at the 3'-end. The modified (e.g. 2'-β-methylated) nucleotides and unmodified nucleotides are incorporated as desired.

The oligonucleotides useful in accordance with embodiments provided herein can be synthesized separately and joined together post-synthetically, for example, by ligation (Moore et al., 1992, Science 256, 9923; Draper et al., International Patent Publication No. WO 93/23569; Shabarova et al., 1991, NAR 19, 4247; Bellon et al., 1997, Nucleosides & Nucleotides, 16, 951; Bellon et al., 1997, Bioconjugate Chem. 8, 204), or by hybridization following synthesis and/or deprotection.

It is noted that a commercially available machine (available, inter alia, from Applied Biosystems) can be used; the oligonucleotides are prepared according to the sequences disclosed herein. Overlapping pairs of chemically synthesized fragments can be ligated using methods well known in the art (e.g., see U.S. Pat. No. 6,121,426). The strands are synthesized separately and then are annealed to each other in the tube. Then, the double-stranded siRNAs are separated from the single-stranded oligonucleotides that were not annealed (e.g. because of the excess of one of them) by HPLC. In relation to the dsRNAs or dsRNA fragments useful in accordance with embodiments of present disclosure, two or more such sequences can be synthesized and linked together for use in the methods, compositions and combinations disclosed herein.

The compounds for use in accordance with can also be synthesized via tandem synthesis methodology, as described for example in US Patent Publication No. US 2004/0019001 (McSwiggen), wherein both siRNA strands are synthesized as a single contiguous oligonucleotide fragment or strand separated by a cleavable linker which is subsequently cleaved to provide separate siRNA fragments or strands that hybridize and permit purification of the siRNA duplex. The linker can be a polynucleotide linker or a non-nucleotide linker.

The present disclosure provides for a pharmaceutical composition comprising three dsRNA molecules for the treatment of any of the diseases and conditions mentioned herein, whereby at least two of the molecules may be physically mixed together in the pharmaceutical composition in amounts which generate equal or otherwise beneficial activity, or may be covalently or non-covalently bound, or joined together by a nucleic acid linker of a length ranging from 2-100, preferably 2-50 or 2-30 nucleotides. In one embodiment, the dsRNA molecules are comprised of a double-stranded nucleic acid structure as described herein, wherein the dsRNA molecules are selected from the oligonucleotides described herein. Thus, the dsRNA molecules may be covalently or non-covalently bound or joined by a linker to form a tandem or a triplet dsRNA compound. Such tandem dsRNA molecules comprising two siRNA sequences are typically of 38-150 nucleotides in length, more preferably 38 or 40-60 nucleotides in length, and longer accordingly if more than two siRNA sequences are included in the tandem molecule. A longer tandem compound comprised of two or more longer sequences which encode siRNA produced via internal cellular processing, e.g., long dsRNAs, is also envisaged, as is a tandem molecule encoding two or more shRNAs. Such tandem molecules are also considered to be a part of the disclosure. A compound comprising two (tandem) or more (RNAistar) dsRNA sequences disclosed herein is envisaged. Examples of such "tandem" or "star" molecules are provided in PCT patent publication no. WO 2007/091269, assigned to the assignee of the present application and incorporated herein by reference in its entirety.

The dsRNA molecules that target HES1, HES5, and HEY2, or HEY2, CDKN1B and NOTCH1 may be the main active components in a pharmaceutical composition, Simultaneous inhibition of said additional gene(s) will likely have an additive or synergistic effect for treatment of the diseases disclosed herein.

Additionally, the dsRNA disclosed herein or any nucleic acid molecule comprising or encoding such dsRNA can be linked or bound (covalently or non-covalently) to antibodies (including aptamer molecules) against cell surface internalizable molecules expressed on the target cells, in order to achieve enhanced targeting for treatment of the diseases disclosed herein. For example, anti-Fas antibody (preferably a neutralizing antibody) may be combined (covalently or non-covalently) with any dsRNA. In another example, an aptamer which can act like a ligand/antibody may be combined (covalently or non-covalently) with any dsRNA.

The nucleic acid molecules disclosed herein can be delivered either directly or with viral or non-viral vectors. When delivered directly, the sequences are generally rendered nuclease resistant. Alternatively the sequences can be incorporated into expression cassettes or constructs such that the sequence is expressed in the cell as discussed herein below. Generally the construct contains the proper regulatory sequence or promoter to allow the sequence to be expressed in the targeted cell. Vectors optionally used for delivery of the compounds of the present invention are commercially available, and may be modified for the purpose of delivery of the compounds of the present invention by methods known to one of skill in the art.

dsRNA Useful for Combination Therapy

In particular embodiments of compositions, combinations, methods, commercial packages and kits provided herein, the double-stranded oligonucleotide (for example dsRNA) possess modifications which may increase activity, increase stability, minimize toxicity and/or affect delivery of the double-stranded oligonucleotide to the middle and inner ear when compared to the corresponding unmodified double-stranded oligonucleotide compound. The double-stranded oligonucleotide molecules are designed to down-regulate target gene expression and attenuate target gene function. In certain embodiments the target gene is transcribed into any one of the mRNA polynucleotides set forth in SEQ ID NOS:1, 2, 7, 10 and 11. In particular embodiments of compositions, combinations, methods, commercial packages and kits provided herein, the double-stranded oligonucleotide (for example dsRNA) possess a sense strand sequence and an antisense strand sequence selected from sense strand oligonucleotide and corresponding antisense strand oligonucleotide set forth in SEQ ID NOS:23-1495 or 26667-26706 (HES1), SEQ ID NOS:1496-2703 or 26707-26732 (HES5), SEQ ID NOS:13004-16621 or 26779-26788 (HEY2), SEQ ID NOS:7444-10533 or 26867-26900 (CDKN1B) or SEQ ID NOS:16622-26666 or 26901-26912 (NOTCH1) useful in generating the chemically modified double-stranded oligonucleotide molecules.

In various embodiments of compositions, combinations, methods, commercial packages and kits, as disclosed herein, in each of a double-stranded oligonucleotide molecule (e.g., dsRNA molecule) the antisense strand may be 18 to 49 nucleotides in length (e.g., 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 nucleotides in length); or 18-35 nucleotides in length; or 18-30 nucleotides in length; or 18-25 nucleotides in length; or 18-23 nucleotides in length; or 19-21 nucleotides in length; or 25-30 nucleotides in length; or 26-28 nucleotides in length. compositions, combinations, methods, commercial packages and kits, as disclosed herein, in each of a double-stranded oligonucleotide molecule (e.g., dsRNA molecule), the antisense strand is 19 nucleotides in length. Similarly the sense strand of a double-stranded oligonucleotide molecule (e.g., dsRNA molecule) may be 18 to 49 nucleotides in length (e.g., 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 nucleotides in length); or 18-35 nucleotides in length; or 18-30 nucleotides in length; or 18-25 nucleotides in length; or 18-23 nucleotides in length; or 19-21 nucleotides in length; or 25-30 nucleotides in length; or 26-28 nucleotides in length. In various preferred embodiments of compositions, combinations, methods, commercial packages and kits, as disclosed herein, in each double-stranded oligonucleotide (e.g., dsRNA molecule), the sense strand is 19 nucleotides in length and the antisense strand is 19 nucleotides in length. In various preferred embodiments of compositions, combinations, methods, commercial packages and kits, as disclosed herein, the duplex region of the double-stranded oligonucleotide molecule (e.g., dsRNA molecule) may be 18-49 nucleotides in length (e.g., about 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 nucleotides in length), 18-35 nucleotides in length; or 18-30 nucleotides in length; or 18-25 nucleotides in length; or 18-23 nucleotides in length; or 18-21 nucleotides in length; or 25-30 nucleotides in length; or 25-28 nucleotides in length. In various preferred embodiments of compositions, combinations, methods, commercial packages and kits, as disclosed herein, the duplex region of the double-stranded oligonucleotide molecule is 19 nucleotides in length.

In various embodiments of compositions, combinations, methods, commercial packages and kits, as disclosed herein, the sense strand and the antisense strand of the double-stranded oligonucleotide (e.g., an dsRNA molecule) are separate oligonucleotide strands. In some embodiments, the separate sense strand and antisense strand form a double stranded structure, also known as a duplex, via hydrogen bonding, for example, Watson-Crick base pairing. In some embodiments one or more nucleotide pairs form non-Watson-Crick base pairing. In some embodiments the sense strand and the antisense strand are two separate strands that are covalently linked to each other. In other embodiments, the sense strand and the antisense strands are part of a single oligonucleotide having both a sense and antisense region; in some preferred embodiments the oligonucleotide has a hairpin structure.

In certain embodiments of compositions, combinations, methods, commercial packages and kits, as disclosed herein, the double-stranded oligonucleotide is symmetrical with regard to overhangs, and has a blunt end on both ends. In other embodiments the double-stranded oligonucleotide is a dsRNA molecule that is symmetrical with regard to overhangs, and has a nucleotide or a non-nucleotide or a combination of a nucleotide and non-nucleotide overhang on both ends of the dsRNA molecule. In certain preferred embodiments, the nucleic acid molecule is a dsRNA molecule that is asymmetrical with regard to overhangs, and has a blunt end on one end of the molecule and an overhang on the other end of the molecule. In some embodiments an asymmetrical dsRNA molecule has a 3'-overhang on one side of a duplex occurring on the sense strand; and a blunt end on the other side of the molecule occurring on both the 5'-end of the sense strand and the 5'-end of the antisense strand. In some embodiments an asymmetrical dsRNA molecule has a 5'-overhang on one side of a duplex occurring on the sense strand; and a blunt end on the other side of the molecule occurring on both the 3'-end of the sense strand and the 3'-end of the antisense strand. In other embodiments an asymmetrical dsRNA molecule has a 3'-overhang on one side of a duplex occurring on the antisense strand; and a blunt end on the other side of the molecule occurring on both the 5'-end of the sense strand and the 5'-end of the antisense strand. In some embodiments an asymmetrical dsRNA molecule has a 5'-overhang on one side of a duplex occurring on the antisense strand; and a blunt end on the other side of the molecule occurring on both the 3'-end of the sense strand and the 3'-end of the antisense strand. In some embodiments the overhangs are nucleotide overhangs, in other embodiments the overhangs are non-nucleotide overhangs. In some embodiments the overhangs are 5' overhangs; in alternative embodiments the overhangs are 3' overhangs.

In certain embodiments of compositions, combinations, methods, commercial packages and kits, as disclosed herein, the double-stranded oligonucleotide has a hairpin structure (having the sense strand and antisense strand on one oligonucleotide), with a loop structure on one end and a blunt end on the other end. In some embodiments, the double-stranded oligonucleotide has a hairpin structure, with a loop structure on one end and an overhang end on the other end; in certain embodiments, the overhang is a 3'-overhang; in certain embodiments the overhang is a 5'-overhang; in certain embodiments the overhang is on the sense strand; in certain embodiments the overhang is on the antisense strand.

In certain embodiments of compositions, combinations, methods, commercial packages and kits, as disclosed herein, the double-stranded oligonucleotide (e.g., dsRNA molecule) may include one or more modifications or modified nucleotides such as described herein. For example, the double-stranded oligonucleotide (e.g., dsRNA molecule) may include a modified nucleotide having a modified sugar; a modified nucleotide having a modified nucleobase; or a modified nucleotide having a modified phosphate group, a modified phosphodiester backbone and/or a modified terminal phosphate group.

In certain embodiments of compositions, combinations, methods, commercial packages and kits, as disclosed herein, the double-stranded oligonucleotide (e.g., dsRNA molecules) may have one or more ribonucleotides that include a modified sugar moiety, for example as described herein. A non-limiting example of a modified sugar moiety is a 2' alkoxy modified sugar moiety. In some preferred embodiments the nucleic acid comprises at least one 2'-O-methyl sugar modified ribonucleotide.

In certain embodiments of compositions, combinations, methods, commercial packages and kits, as disclosed herein, the double-stranded oligonucleotide (e.g., dsRNA molecule) may have one or more modified nucleobase(s), for example as described herein.

In certain embodiments of compositions, combinations, methods, commercial packages and kits, as disclosed herein, the double-stranded oligonucleotide (e.g., dsRNA molecule) may have one or more modifications to the phosphodiester backbone, for example as described herein.

In certain embodiments of compositions, combinations, methods, commercial packages and kits, as disclosed herein, the double-stranded oligonucleotide (e.g., dsRNA molecule) may have one or more modified phosphate group(s), for example as described herein.

In various embodiments of compositions, combinations, methods, commercial packages and kits, as disclosed herein, the double-stranded oligonucleotide (e.g., dsRNA molecule) may include an unmodified antisense strand and a sense strand having one or more modifications. In some embodiments the double-stranded oligonucleotide (e.g., dsRNA molecule) may include an unmodified sense strand and an antisense strand having one or more modifications. In preferred embodiments, the double-stranded oligonucleotide (e.g., dsRNA molecule) may include one or more modified nucleotides in the both the sense strand and the antisense strand.

In various embodiments of compositions, combinations, methods, commercial packages and kits, as disclosed herein, the double-stranded oligonucleotide (e.g., dsRNA molecules) may include a phosphate group at the 5' end of the sense and/or the antisense strand (i.e. a 5'-terminal phosphate group). In some embodiments the double-stranded oligonucleotide may include a phosphate group at the 5' terminus of the antisense strand.

In various embodiments of compositions, combinations, methods, commercial packages and kits, as disclosed herein, the double-stranded oligonucleotide (e.g., dsRNA molecules) may include a phosphate group at the 3' end of the sense and/or the antisense strand (i.e. a 3'-terminal phosphate group). In some embodiments the double-stranded oligonucleotide may include a phosphate group at the 3' terminus of the antisense strand.

In some embodiments of compositions, combinations, methods, commercial packages and kits, as disclosed herein, the double-stranded oligonucleotide (e.g., dsRNA molecules) may include a phosphate group at the 3' terminus of the antisense strand and the sense strand.

In some embodiments of compositions, combinations, methods, commercial packages and kits, as disclosed herein, the double-stranded oligonucleotide (e.g., dsRNA molecules) the antisense strand and the sense strand of the nucleic acid molecule are non-phosphorylated at both the 3' terminus and at the 5' terminus.

In various embodiments of compositions, combinations, methods, commercial packages and kits, as disclosed herein, at least one double-stranded oligonucleotide is independently having the structure (A1):

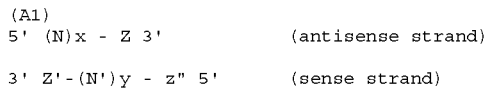

wherein each N and N' is a ribonucleotide which may be unmodified or modified, or an unconventional moiety;
wherein each of (N)x and (N')y is an oligonucleotide in which each consecutive N or N' is joined to the next N or N' by a covalent bond;
wherein each of Z and Z' is independently present or absent, but if present independently comprises 1-5 consecutive nucleotides, 1-5 consecutive non-nucleotide moieties or a combination thereof covalently attached at the 3' terminus of the strand in which it is present;
wherein z" may be present or absent, but if present is a capping moiety covalently attached at the 5' terminus of (N')y;
each of x and y is independently an integer from 18 to 40;
wherein the sequence of (N')y is complementary to the sequence of (N)x; and wherein (N)x comprises an antisense sequence to a consecutive sequence in an mRNA selected from an mRNA encoding HES1, an mRNA encoding HES5, an mRNA encoding HEY2, an mRNA encoding CDKN1B and an mRNA encoding NOTCH1.

In various embodiments of compositions, combinations, methods, commercial packages and kits, as disclosed herein, at least one double-stranded oligonucleotide is independently having the structure (A1), (N)x comprises an antisense sequence and (N')y comprises a sense sequence set forth in any one of SEQ ID NOS:23-693 and 26691-26706 (HES1); SEQ ID NOS:1496-2029 and 26725-26732 (HES5); SEQ ID NOS:7444-9007 and 26887-26900 (CDKN1B); SEQ ID NOS:13004-14801 and 26785-26788 (HEY2); SEQ ID NOS:16622-18643 and 26922-26912 (NOTCH1). In some embodiments preferred (N)x and (N')y are set forth in any one of SEQ ID NOS:26691-26706 (HES1); SEQ ID NOS:26725-26732 (HES5); SEQ ID NOS: 26887-26900 (CDKN1B); SEQ ID NOS:26785-26788 (HEY2); SEQ ID NOS:26922-26912 (NOTCH1).

In various embodiments of compositions, combinations, methods, commercial packages and kits, as disclosed herein, at least one double-stranded oligonucleotide is independently having the structure (A1) and the covalent bond joining each consecutive N and/or N' is a phosphodiester bond.

In various embodiments of compositions, combinations, methods, commercial packages and kits, as disclosed herein, at least one double-stranded oligonucleotide is independently having the structure (A1) x=y and each of x and y is 19, 20, 21, 22 or 23. In preferred embodiments x=y=19.

In some embodiments of compositions, combinations, methods, commercial packages and kits, as disclosed herein, at least one double-stranded oligonucleotide comprise a DNA moiety or a mismatch to the target at position 1 of the antisense strand (5' terminus). In some embodiments of compositions, combinations, methods, commercial packages and kits, as disclosed herein, at least one double-stranded oligonucleotide has a structure (A2) set forth below:

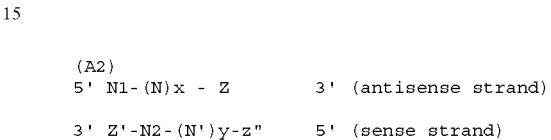

wherein each N1, N2, N and N' is independently an unmodified or modified nucleotide, or an unconventional moiety;
wherein each of (N)x and (N')y is an oligonucleotide in which each consecutive N or N' is joined to the adjacent N or N' by a covalent bond;
wherein each of x and y is independently an integer between 17 and 39;
wherein N2 is covalently bound to (N')y;
wherein N1 is covalently bound to (N)x and is mismatched to the target mRNA or is a complementary DNA moiety to the target mRNA;
wherein N1 is a moiety selected from the group consisting of natural or modified: uridine, deoxyribouridine, ribothymidine, deoxyribothymidine, adenosine or deoxyadenosine, an abasic ribose moiety and an abasic deoxyribose moiety;
wherein z" may be present or absent, but if present is a capping moiety covalently attached at the 5' terminus of N2-(N')y;
wherein each of Z and Z' is independently present or absent, but if present is independently 1-5 consecutive nucleotides, 1-5 consecutive non-nucleotide moieties or a combination thereof covalently attached at the 3' terminus of the strand in which it is present; and
wherein the sequence of (N')y has complementarity to the sequence of (N)x; and wherein the sequence of (N)x is an antisense sequence to a consecutive sequence in HES1 mRNA (SEQ ID NO:1); HES5 mRNA (SEQ ID NO:2), HEY2 mRNA (SEQ ID NO:10), CDKN1B mRNA (SEQ ID NO:7) or NOTCH1 mRNA (SEQ ID NO:11).

In some embodiments of compositions, combinations, methods, commercial packages and kits, as disclosed herein, at least one double-stranded oligonucleotide has a structure (A2) wherein the sequence of (N')y is complementary to the sequence of (N)x; and wherein the sequence of (N)x comprises an antisense sequence and (N')y comprises a sense sequence set forth in any one of SEQ ID NOS:694-1495 and 26667-26690 (HES1); SEQ ID NOS:2030-2703 and 26707-26724 (HES5); SEQ ID NOS:9008-10533 and 26867-26886 (CDKN1B); SEQ ID NOS:14802-16389 and 26779-26784 (HEY2); SEQ ID NOS:18644-26666 and 26901-26910 (NOTCH1). Preferred (N)x and (N')y are set forth in any one of SEQ ID NOS:26667-26690 (HES1); SEQ ID NOS: 26707-26724 (HES5); SEQ ID NOS:26867-26886 (CDKN1B); SEQ ID NOS:26779-26784 (HEY2); SEQ ID NOS:26901-26910 (NOTCH1). Molecules covered by the description of Structure (A2) are also referred to herein as "18+1" or "18+1 mer". In some embodiments, the N2-(N')y and N1-(N)x useful in generating double-stranded oligonucleotides having Structure (A2) are presented in Tables I-V, particularly the sequences designated as "18+1" type. In certain preferred embodiments (N)x and (N')y are selected from the sequence pairs shown in Tables I-V.

In preferred In some embodiments of compositions, combinations, methods, commercial packages and kits, as disclosed herein, at least one double-stranded oligonucleotide has a structure (A2), the sequence of (N')y is fully complementary to the sequence of (N)x. In various embodiments sequence of N2-(N')y is complementary to the sequence of N1-(N)x. In some embodiments (N)x comprises an antisense that is fully complementary to about 17 to about 39 consecutive nucleotides in a target mRNA set forth in any one of SEQ ID NOS:1, 2, 10, 7 or 11. In other embodiments (N)x comprises an antisense that is substantially complementary to about 17 to about 39 consecutive nucleotides in a target mRNA set forth in SEQ ID NOS:1, 2, 10, 7 or 11. In some embodiments, at least one double-stranded oligonucleotide has a structure (A2) and N1 and N2 form a Watson-Crick base pair. In other embodiments, at least one double-stranded oligonucleotide has a structure (A2) and N1 and N2 form a non-Watson-Crick base pair. In some embodiments a base pair is formed between a ribonucleotide and a deoxyribonucleotide.

In some embodiments of compositions, combinations, methods, commercial packages and kits, as disclosed herein, at least one double-stranded oligonucleotide has a structure (A2), x=y=18, x=y=19 or x=y=20. In preferred embodiments x=y=18. When x=18 in N1-(N)x, N1 refers to position 1 and positions 2-19 are included in (N)$_{18}$. When y=18 in N2-(N')y, N2 refers to position 19 and positions 1-18 are included in (N')$_{18}$. In some embodiments at least one double-stranded oligonucleotide has a structure (A2), N1 is covalently bound to (N)x and is mismatched to the target mRNA set forth in SEQ ID NO:1, 2, 10, 7 or 11. In various embodiments at least one double-stranded oligonucleotide has a structure (A2), N1 is covalently bound to (N)x and is a DNA moiety complementary to the target mRNA set forth in SEQ ID NO:1, 2, 10, 7 or 11.

In some embodiments of compositions, combinations, methods, commercial packages and kits, as disclosed herein, at least one double-stranded oligonucleotide has a structure (A2), a uridine in position 1 of the antisense strand is substituted with an N1 selected from natural or modified: adenosine, deoxyadenosine, uridine, deoxyuridine (dU), ribothymidine or deoxythymidine. In various embodiments, at least one double-stranded oligonucleotide has a structure (A2), N1 is selected from natural or modified: adenosine, deoxyadenosine or deoxyuridine. For example, in some embodiments a cytidine in position 1 is replaced with an adenine or a uridine; a guanosine in position 1 is replaced with an adenine or a uridine; or an adenine is replaced with a uridine.

In some embodiments of compositions, combinations, methods, commercial packages and kits, as disclosed herein, at least one double-stranded oligonucleotide has a structure (A2), guanosine in position 1 (N1) of the antisense strand is substituted with a natural or modified: adenosine, deoxyadenosine, uridine, deoxyuridine, ribothymidine or deoxythymidine. In various embodiments N1 is selected from a natural or modified: adenosine, deoxyadenosine, uridine or deoxyuridine.

In some embodiments of compositions, combinations, methods, commercial packages and kits, as disclosed herein, at least one double-stranded oligonucleotide has a structure (A2), cytidine in position 1 (N1) of the antisense strand is substituted with a natural or modified: adenosine, deoxyadenosine, uridine, deoxyuridine, ribothymidine or deoxythymidine. In various embodiments N1 is selected from a natural or modified: adenosine, deoxyadenosine, uridine or deoxyuridine.

In some embodiments of compositions, combinations, methods, commercial packages and kits, as disclosed herein, at least one double-stranded oligonucleotide has a structure (A2), adenosine in position 1 (N1) of the antisense strand is substituted with a natural or modified: deoxyadenosine, deoxyuridine, ribothymidine or deoxythymidine.

In some embodiments of compositions, combinations, methods, commercial packages and kits, as disclosed herein, at least one double-stranded oligonucleotide has a structure (A2), N1 and N2 form a base pair between natural or modified: uridine or deoxyuridine, and adenosine or deoxyadenosine. In other embodiments N1 and N2 form a base pair between natural or modified: deoxyuridine and adenosine.

In some embodiments of compositions, combinations, methods, commercial packages and kits, as disclosed herein, the double-stranded oligonucleotide molecules are also referred to as "duplexes". In some embodiments at least one double-stranded oligonucleotide has a structure (A2), and the double stranded oligonucleotide is a chemically modified dsRNA.

In certain preferred embodiments of compositions, combinations, methods, commercial packages and kits, as disclosed herein, the double-stranded oligonucleotide molecules has Structure (A2), and x=y=18. In some embodiments x=y=18 and (N)x consists of an antisense oligonucleotide present in SEQ ID NOS:694-1495 and 26667-26690 (HES1); SEQ ID NOS:2030-2703 and 26707-26724 (HES5); SEQ ID NOS:9008-10533 and 26867-26886 (CDKN1B); SEQ ID NOS:14802-16389 and 26779-26784 (HEY2); SEQ ID NOS:18644-26666 and 26901-26910 (NOTCH1).

In some embodiments of compositions, combinations, methods, commercial packages and kits, as disclosed herein, at least one double-stranded oligonucleotide has Structure (A2) and N1 is selected from a natural uridine and a modified uridine. In some embodiments, N1 is a natural uridine. In some embodiments, (N)x comprises an antisense oligonucleotide and (N')y comprises a sense oligonucleotide present in sequence pairs set forth in SEQ ID NOS:694-1495 (HES1); SEQ ID NOS:2030-2703 (HES5); SEQ ID NOS: 9008-10533 (CDKN1B); SEQ ID NOS:14802-16389 (HEY2); SEQ ID NOS:18644-26666 (NOTCH1).

In some embodiments of compositions, combinations, methods, commercial packages and kits, as disclosed herein, at least one double-stranded oligonucleotide has Structure (A2), x=y=18 and N1-(N)x comprises an antisense oligonucleotide and N2-(N')y comprises a sense oligonucleotide present in sequence pairs set forth in SEQ ID 26667-26690 (HES1); SEQ ID NOS: 26707-26724 (HES5); SEQ ID NOS: 26867-26886 (CDKN1B); SEQ ID NOS: 26779-26784 (HEY2); SEQ ID NOS: 26901-26910 (NOTCH1).

In some embodiments, at least one double-stranded oligonucleotide has Structure (A2), x=y=18 and N1 is selected from a natural or modified uridine, a natural or modified adenine, and a natural or modified thymidine.

In some embodiments at least one double-stranded oligonucleotide has Structure (A2), wherein N1 is a 2'OMe sugar-modified uridine or a 2'OMe sugar-modified adenosine. In certain embodiments at least one double-stranded oligonucleotide has Structure (A2), N2 is a 2'OMe sugar modified ribonucleotide or deoxyribonucleotide.

In some embodiments of Structure (A1) and/or Structure (A2), each N consists of an unmodified ribonucleotide. In some embodiments of Structure (A1) and/or Structure (A2) each N' consists of an unmodified ribonucleotide. In preferred embodiments at least one of N and/or N' comprises a chemically modified ribonucleotide, an unmodified deoxyribonucleotide, a chemically modified deoxyribonucleotide or an unconventional moiety. In some embodiments the unconventional moiety is selected from a mirror nucleotide, an abasic ribose moiety and an abasic deoxyribose moiety. In some embodiments the unconventional moiety is a mirror nucleotide, preferably an L-DNA moiety. In some embodiments at least one of N or N' comprises a 2'OMe sugar-modified ribonucleotide.

In some embodiments of Structure (A1) and/or Structure (A2) the sequence of (N')y is fully complementary to the sequence of (N)x. In other embodiments of Structure (A1) and/or Structure (A2) the sequence of (N')y is substantially complementary to the sequence of (N)x.

In some embodiments of Structure (A1) and/or Structure (A2) (N)x includes an antisense sequence that is fully complementary to about 17 to about 39 consecutive nucleotides in a target mRNA set forth in any one of SEQ ID NO:1, 2, 10, 7 OR 11. In other embodiments of Structure A1 and/or Structure A2 (N)x includes an antisense that is substantially complementary to about 17 to about 39 consecutive nucleotides in a target mRNA set forth in any one of SEQ ID NO:1, 2, 10, 7 OR 11. In some embodiments of Structure (A1) and/or Structure (A2), the dsRNA compound is blunt ended, for example, wherein each of z", Z and Z' is absent. In an alternative embodiment, at least one of z", Z or Z' is present.

In various embodiments Z and Z' independently include one or more covalently linked modified and or unmodified nucleotides, including deoxyribonucleotides and ribonucleotides, or one or more unconventional moieties for example inverted abasic deoxyribose moiety or abasic ribose moiety or a mirror nucleotide; one or more non-nucleotide C3 moiety or a derivative thereof, non-nucleotide C4 moiety or a derivative thereof or non-nucleotide C5 moiety or a derivative thereof, an non-nucleotide amino-C6 moiety or a derivative thereof, as defined herein, and the like. In some embodiments Z' is absent and Z is present and includes one or more non-nucleotide C3 moieties. In some embodiments Z is absent and Z' is present and includes one or more non-nucleotide C3 moieties. In some embodiments each of Z and Z' independently comprises one or more non-nucleotide C3 moieties or one or more non-nucleotide amino-C6 moieties. In some embodiments z" is present and is selected from a mirror nucleotide, an abasic moiety and an inverted abasic moiety. In some embodiments of Structures (A1) and/or (A2) each of Z and Z' includes an abasic moiety, for example a deoxyriboabasic moiety (referred to herein as "dAb") or riboabasic moiety (referred to herein as "rAb"). In some embodiments each of Z and/or Z' comprises two covalently linked abasic moieties and is for example dAb-dAb or rAb-rAb or dAb-rAb or rAb-dAb, wherein each moiety is covalently attached to an adjacent moiety, preferably via a phospho-based bond. In some embodiments the phospho-based bond includes a phosphorothioate, a phosphonoacetate or a phosphodiester bond. In preferred embodiments the phospho-based bond is a phosphodiester bond.

In some embodiments each of Z and/or Z' independently includes an alkyl moiety, optionally propane [(CH2)3] moiety (C3) or a derivative thereof including propanol (C3OH) and phospho derivative of propanediol ("C3Pi"). In some embodiments each of Z and/or Z' includes two alkyl moieties and in some examples is C3Pi-C3OH. In the example of C3Pi-C3OH, the 3' terminus of the antisense strand and/or the 3' terminus of the sense strand is covalently attached to a C3 moiety via a phospho-based bond and the C3 moiety is covalently bound to a C3OH moiety via a phospho-based bond. In some embodiments the phospho-based bonds include a phosphorothioate, a phosphonoacetate or a phosphodiester bond. In preferred embodiments the phospho-based bond is a phosphodiester bond.

In specific embodiments of Structures (A1) and (A2), Z comprises C3Pi-C3OH. In specific embodiments of Structures (A1) and (A2), Z' comprises C3Pi or C3OH. In some embodiments of Structures (A1) and (A2), a double stranded nucleic acid molecule includes a C3Pi-C3OH moiety covalently attached to the 3' terminus of the antisense strand and a C3Pi or C3OH moiety covalently attached to the 3' terminus of the sense strand.

In some embodiments of Structure (A1) and/or Structure (A2) each N consists of an unmodified ribonucleotide. In some embodiments of Structure (A1) and/or Structure (A2) each N' consists of an unmodified ribonucleotide. In preferred embodiments, at least one of N and/or N' is a chemically modified ribonucleotide, an unmodified deoxyribonucleotide, a chemically modified deoxyribonucleotide or an unconventional moiety.

In other embodiments a compound of Structure (A1) and/or (A2) includes at least one ribonucleotide modified in its sugar residue. In some embodiments the compound comprises a modification at the 2' position of the sugar residue. In some embodiments the modification in the 2' position comprises the presence of an amino, a fluoro, an alkoxy or an alkyl moiety. In certain embodiments the 2' modification includes an alkoxy moiety. In preferred embodiments the alkoxy moiety is a methoxy moiety (also referred to as 2'-O-methyl; 2'OMe; 2'OMe; 2'-OCH3). In some embodiments a nucleic acid compound includes 2'OMe sugar modified alternating ribonucleotides in one or both of the antisense strand and the sense strand. In other embodiments a compound includes 2'OMe sugar modified ribonucleotides in the antisense strand, (N)x or N1-(N)x, only. In some embodiments, the 2'OMe sugar modified ribonucleotides alternate with unmodified nucleotides. In certain embodiments the middle ribonucleotide of the antisense strand; e.g. ribonucleotide in position 10 in a 19-mer strand, is unmodified. In various embodiments the nucleic acid compound includes at least 5 alternating 2'OMe sugar modified ribonucleotides and unmodified ribonucleotides. In additional embodiments a compound of Structure (A1) and/or (A2) includes modified ribonucleotides in alternating positions wherein each ribonucleotide at the 5' terminus and at the 3' terminus of (N)x or N1-(N)x is modified in its sugar residue, and each ribonucleotide at the 5' terminus and at the 3' terminus of (N')y or N2-(N)y is unmodified in its sugar residue. In various embodiments the ribonucleotides in alternating positions are modified at the 2' position of the sugar residue.

In some embodiments the nucleic acid compound includes at least 5 alternating 2'OMe sugar modified ribonucleotides and unmodified ribonucleotides, for example at positions 1, 3, 5, 7 and 9 or at positions 11, 13, 15, 17, 19 (5'>3'). In some embodiments, (N)x of Structure (A1) or N1-(N)x of Structure (A2) includes 2'OMe sugar modified ribonucleotides in positions 2, 4, 6, 8, 11, 13, 15, 17 and 19. In some embodiments, (N)x of Structure (A1) or N1-(N)x of Structure (A2) includes 2'OMe sugar modified ribonucleotides in positions 1, 3, 5, 7, 9, 11, 13, 15, 17 and 19. In some embodiments, (N)x of Structure (A1) or N1-(N)x of Structure (A2) includes 2'OMe sugar modified ribonucleotides in one or more pyrimidines.

In some embodiments of Structure (A1) and/or (A2), neither of the sense strand nor the antisense strand is phosphorylated at the 3' terminus and at the 5' terminus. In other embodiments one or both of the sense strand and/or the antisense strand are phosphorylated at the 3' termini. In other embodiments one or both of the sense strand and/or the antisense strand are phosphorylated at the 5' terminus.

In some embodiments the double stranded molecule disclosed herein includes one or more of the following modifications:
N in at least one of positions 5, 6, 7, 8, or 9 from the 5' terminus of the antisense strand is selected from a DNA, TNA, a 2'5' nucleotide or a mirror nucleotide;
N' in at least one of positions 9 or 10 from the 5' terminus of the sense strand is selected from a TNA, 2'5' nucleotide and a pseudoUridine;
N' in 4, 5, or 6 consecutive positions at the 3' terminus of (N')y comprises a 2'5' ribonucleotide;
one or more pyrimidine ribonucleotides are 2' sugar modified in the sense strand, the antisense strand or both the sense strand and the antisense strand.

In some embodiments the double stranded molecule disclosed herein includes a combination of the following modifications:
the antisense strand includes a DNA, TNA, a 2'5' nucleotide or a mirror nucleotide in at least one of positions 5, 6, 7, 8, or 9 from the 5' terminus;
the sense strand includes at least one of a TNA, a 2'5' nucleotide and a pseudoUridine in positions 9 or 10 from the 5' terminus; and
one or more pyrimidine ribonucleotides are 2' modified in the sense strand, the antisense strand or both the sense strand and the antisense strand.

In some embodiments the double stranded molecule disclosed herein includes a combination of the following modifications:
the antisense strand includes a DNA, 2'5' nucleotide or a mirror nucleotide in at least one of positions 5, 6, 7, 8, or 9 from the 5' terminus;
the sense strand includes 4, 5, or 6 consecutive 2'5' nucleotides at the 3' penultimate or 3' terminal positions; and
one or more pyrimidine ribonucleotides are 2' sugar modified in the sense strand, the antisense strand or both the sense strand and the antisense strand.

In some embodiments of Structure (A1) and/or (A2) (N)y includes at least one unconventional moiety selected from a mirror nucleotide, a 2'5' ribonucleotide and a TNA. In some embodiments the unconventional moiety is a mirror nucleotide. In various embodiments the mirror nucleotide is selected from an L-ribonucleotide (L-RNA) and an L-deoxyribonucleotide (L-DNA). In preferred embodiments the mirror nucleotide is L-DNA. In certain embodiments the sense strand comprises an unconventional moiety in position 9 or 10 (from the 5' terminus). In preferred embodiments the sense strand includes an unconventional moiety in position 9 (from the 5' terminus). In some embodiments the sense strand is 19 nucleotides in length and comprises 4, 5, or 6 consecutive unconventional moieties in positions 15 (from the 5' terminus). In some embodiments the sense strand includes 4 consecutive 2'5' ribonucleotides in positions 15, 16, 17, and 18. In some embodiments the sense strand includes 5 consecutive 2'5' ribonucleotides in positions 15, 16, 17, 18 and 19. In various embodiments the sense strand further comprises Z'. In some embodiments Z' includes a C3OH moiety or a C3Pi moiety.

In some embodiments of Structure (A1) and/or (A2) (N)y comprises at least one unconventional moiety selected from a mirror nucleotide and a nucleotide joined to an adjacent nucleotide by a 2'-5' internucleotide phosphate bond. In some embodiments the unconventional moiety is a mirror nucleotide. In various embodiments the mirror nucleotide is selected from an L-ribonucleotide (L-RNA) and an L-deoxyribonucleotide (L-DNA). In preferred embodiments the mirror nucleotide is L-DNA.

In some embodiments of Structure A1 (N')y comprises at least one L-DNA moiety. In some embodiments x=y=19 and (N')y consists of unmodified ribonucleotides at positions 1-17 and 19 and one L-DNA at the 3' penultimate position (position 18). In other embodiments x=y=19 and (N')y consists of unmodified ribonucleotides at position 1-16 and 19 and two consecutive L-DNA nucleotides at the 3' penultimate position (positions 17 and 18). In various embodiments the unconventional moiety is a nucleotide joined to an adjacent nucleotide by a 2'-5' internucleotide phosphate linkage. According to various embodiments (N')y comprises 2, 3, 4, 5, or 6 consecutive ribonucleotides at the 3' terminus linked by 2'-5' internucleotide linkages. In one embodiment, four consecutive ribonucleotides at the 3' terminus of (N')y are joined by three 2'-5' phosphodiester bonds. In one embodiment, five consecutive ribonucleotides at the 3' terminus of (N')y are joined by four 2'-5' phosphodiester bonds. In some embodiments, wherein one or more of the 2'-5' ribonucleotides form a 2'-5' phosphodiester bonds the nucleotide further comprises a 3'-O-methyl (3'OMe) sugar modification. In some embodiments the 3' terminal nucleotide of (N')y comprises a 3'OMe sugar modification. In certain embodiments x=y=19 and (N')y comprises two or more consecutive nucleotides at positions 15, 16, 17, 18 and 19 which are joined to an adjacent nucleotide by a 2'-5' internucleotide bond. In various embodiments, the nucleotide forming the 2'-5' internucleotide bond comprises a ribonucleotide. In preferred embodiments the 2'-5' internucleotide bond is a phosphosdiester internucleotide bond. In various embodiments the nucleotide forming the 2'-5' internucleotide bond comprises a 3' deoxyribose nucleotide or a 3' methoxy nucleotide. In various embodiments, the ribonucleotide forming the 2'-5' internucleotide bond comprises a 3' deoxyribose ribonucleotide or a 3' methoxy ribonucleotide. In some embodiments x=y=19 and (N')y comprises nucleotides joined to the adjacent nucleotide by a 2'-5' internucleotide bond between positions 15-16, 16-17 and 17-18 or between positions 16-17, 17-18 and 18-19. In some embodiments x=y=19 and (N')y comprises nucleotides joined to the adjacent nucleotide by a 2'-5' internucleotide bond between positions 16-17 and 17-18 or between positions 17-18 and 18-19 or between positions 15-16 and 17-18. In various embodiments, the nucleotides forming the 2'-5' internucleotide bond comprise ribonucleotides. In various embodiments, the nucleotides forming the 2'-5' internucleotide bond are ribonucleotides. In other embodiments the pyrimidine ribonucleotides (rU, rC) in (N')y are substituted with a ribonucleotide joined to the adjacent ribonucleotide by a 2'-5' internucleotide bond.

In some embodiments of Structure (A2), (N)y comprises at least one L-DNA moiety. In some embodiments x=y=18 and N2-(N')y, consists of unmodified ribonucleotides at positions 1-17 and 19 and one L-DNA at the 3' penultimate position (position 18). In other embodiments x=y=18 and N2-(N')y consists of unmodified ribonucleotides at position 1-16 and 19 and two consecutive L-DNA at the 3' penultimate position (positions 17 and 18). In various embodiments the unconventional moiety is a nucleotide joined to an adjacent nucleotide by a 2'-5' internucleotide phosphate linkage. According to various embodiments N2-(N')y comprises 2, 3, 4, 5, or 6 consecutive ribonucleotides at the 3' terminus linked by 2'-5' internucleotide linkages. In one embodiment, four consecutive ribonucleotides at the 3' terminus of N2-(N')y are joined by three 2'-5' phosphodiester bonds, wherein one or more of the 2'-5' ribonucleotides which form the 2'-5' phosphodiester bonds further comprises a 3'-O-methyl (3'OMe) sugar modification. In some embodiments the 3' terminal ribonucleotide of N2-(N')y comprises a 2'OMe sugar modification. In certain embodiments x=y=18 and N2-(N')y comprises two or more consecutive nucleotides at positions 15, 16, 17, 18 and 19 joined to an adjacent nucleotide by a 2'-5' internucleotide bond. In various embodiments the nucleotide forming the 2'-5' internucleotide bond comprises a 3' deoxyribose nucleotide or a 3' methoxy nucleotide. In various embodiments, the ribonucleotide forming the 2'-5' internucleotide bond comprises a 3' deoxyribose ribonucleotide or a 3' methoxy ribonucleotide. In some embodiments x=y=18 and N2-(N')y comprises nucleotides joined to the adjacent nucleotide by a 2'-5' internucleotide bond between positions 16-17 and 17-18 or between positions 17-18 and 18-19 or between positions 15-16 and 17-18. In various embodiments, the nucleotides forming the 2'-5' internucleotide bond comprise ribonucleotides. In various embodiments, the nucleotides forming the 2'-5' internucleotide bond are ribonucleotides. In other embodiments a pyrimidine ribonucleotide (rU, rC) in (N')y comprises a ribonucleotide joined to the adjacent ribonucleotide by a 2'-5' internucleotide bond.

In further embodiments of Structures (A1) and/or (A2) (N')y comprises 1-8 modified ribonucleotides wherein the modified ribonucleotide is a deoxyribose (DNA) nucleotide. In certain embodiments (N')y comprises 1, 2, 3, 4, 5, 6, 7, or up to 8 DNA moieties.

In presently preferred embodiments the inhibitor provided herein is a synthetic, chemically modified double-stranded oligonucleotide (e.g. dsRNA) compound, selected form: a double-stranded oligonucleotide that down-regulates HES1 expression and includes an oligonucleotide pair selected from Table I; a double-stranded oligonucleotide that down-regulates HES5 expression and includes an oligonucleotide pair selected from Table II; a double-stranded oligonucleotide that down-regulates HEY2 expression and includes an oligonucleotide pair selected from Table III; a double-stranded oligonucleotide that down-regulates CDKN1B expression and includes an oligonucleotide pair selected from Table IV; a double-stranded oligonucleotide that down-regulates NOTCH1 expression and includes an oligonucleotide pair selected from Table V. Tables I-V are provided herein below.

TABLE I

Selected HES1_dsRNA

| dsRNA Name | SEQ ID NO: | Sense strand (5' > 3') | SEQ ID NO: | Antisense strand (5' > 3') | Type |
| --- | --- | --- | --- | --- | --- |
| HES1_12 | 26667 | GCCAGCUGAUAUAAUGGAA | 26679 | UUCCAUUAUAUCAGCUGGC | 18 + 1 |
| HES1_13 | 26668 | GCCAGUGUCAACACGACAA | 26680 | UUGUCGUGUUGACACUGGC | 18 + 1 |
| HES1_14 | 26669 | CAGCGAGUGCAUGAACGAA | 26681 | UUCGUUCAUGCACUCGCUG | 18 + 1 |
| HES1_16 | 26670 | GAACGAGGUGACCCGCUUA | 26682 | UAAGCGGGUCACCUCGUUC | 18 + 1 |
| HES1_19 | 26671 | CCAGUGUCAACACGACACA | 26683 | UGUGUCGUGUUGACACUGG | 18 + 1 |
| HES1_20 | 26672 | CGAGUGCAUGAACGAGGUA | 26684 | UACCUCGUUCAUGCACUCG | 18 + 1 |
| HES1_21 | 26673 | UGUCAACACGACACCGGAA | 26685 | UUCCGGUGUCGUGUUGACA | 18 + 1 |
| HES1_22 | 26674 | CAGUGUCAACACGACACCA | 26686 | UGGUGUCGUGUUGACACUG | 18 + 1 |
| HES1_24 | 26675 | GGCGGACUCCAUGUGGAGA | 26687 | UCUCCACAUGGAGUCCGCC | 18 + 1 |
| HES1_28 | 26676 | CGGAUAAACCAAAGACAGA | 26688 | UCUGUCUUUGGUUUAUCCG | 18 + 1 |
| HES1_33 | 26677 | AGUGCAUGAACGAGGUGAA | 26689 | UUCACCUCGUUCAUGCACU | 18 + 1 |
| HES1_36 | 26678 | CAGCGAGUGCAUGAACGAU | 26690 | AUCGUUCAUGCACUCGCUG | 18 + 1 |
| HES1_10 | 26691 | GUAUUAAGUGACUGACCAU | 26699 | AUGGUCAGUCACUUAAUAC | 19 |
| HES1_11 | 26692 | GAAAACACUGAUUUUGGAU | 26700 | AUCCAAAAUCAGUGUUUUC | 19 |
| HES1_15 | 26693 | ACUGCAUGACCCAGAUCAA | 26701 | UUGAUCUGGGUCAUGCAGU | 19 |
| HES1_17 | 26694 | AGCCAGUGUCAACACGACA | 26702 | UGUCGUGUUGACACUGGCU | 19 |
| HES1_18 | 26695 | GUGUCAACACGACACCGGA | 26703 | UCCGGUGUCGUGUUGACAC | 19 |
| HES1_26 | 26696 | CAGUGAAGCACCUCCGGAA | 26704 | UUCCGGAGGUGCUUCACUG | 19 |
| HES1_27 | 26697 | CAUGGAGAAAAGACGAAGA | 26705 | UCUUCGUCUUUUCUCCAUG | 19 |
| HES1_35 | 26698 | CAGCUGAUAUAAUGGAGAA | 26706 | UUCUCCAUUAUAUCAGCUG | 19 |

TABLE II

Selected HES5 dsRNA

| dsRNA Name | SEQ ID NO: | Sense strand (5' > 3') | SEQ ID NO: | Antisense strand (5' > 3') | Type |
|---|---|---|---|---|---|
| HES5_19 | 26707 | GGAGUUCGCGCGGCACCAA | 26716 | UUGGUGCCGCGCGAACUCC | 18 + 1 |
| HES5_20 | 26708 | GCGACACGCAGAUGAAGCA | 26717 | UGCUUCAUCUGCGUGUCGC | 18 + 1 |
| HES5_22 | 26709 | CGGGCACAUUUGCCUUUUA | 26718 | UAAAAGGCAAAUGUGCCCG | 18 + 1 |
| HES5_23 | 26710 | CGCCAGCGACACGCAGAUA | 26719 | UAUCUGCGUGUCGCUGGCG | 18 + 1 |
| HES5_24 | 26711 | CCGACUGCGGAAGCCGGUA | 26720 | UACCGGCUUCCGCAGUCGG | 18 + 1 |
| HES5_26 | 26712 | GCGCGGCACCAGCCCAACA | 26721 | UGUUGGGCUGGUGCCGCGC | 18 + 1 |
| HES5_27 | 26713 | AACCGACUGCGGAAGCCGA | 26722 | UCGGCUUCCGCAGUCGGUU | 18 + 1 |
| HES5_28 | 26714 | CGACUGCGGAAGCCGGUGA | 26723 | UCACCGGCUUCCGCAGUCG | 18 + 1 |
| HES5_29 | 26715 | CGACACGCAGAUGAAGCUA | 26724 | UAGCUUCAUCUGCGUGUCG | 18 + 1 |
| HES5_10 | 26725 | CUGUAGAGGACUUUCUUCA | 26729 | UGAAGAAAGUCCUCUACAG | 19 |
| HES5_21 | 26726 | GCCAGCGACACGCAGAUGA | 26730 | UCAUCUGCGUGUCGCUGGC | 19 |
| HES5_25 | 26727 | GCGACACGCAGAUGAAGCU | 26731 | AGCUUCAUCUGCGUGUCGC | 19 |
| HES5_8 | 26728 | GGGUUCUAUGAUAUUUGUA | 26732 | UACAAAUAUCAUAGAACCC | 19 |

TABLE III

Selected HEY2 dsRNA

| dsRNA Name | SEQ ID NO: | Sense strand (5' > 3') | SEQ ID NO: | AntiSense strand (5' > 3') | Type |
|---|---|---|---|---|---|
| HEY2_1 | 26779 | GGGAGCGAGAACAAUUACA | 26782 | UGUAAUUGUUCUCGCUCCC | 18 + 1 |
| HEY2_2 | 26780 | GGGUAAAGGCUACUUUGAA | 26783 | UUCAAAGUAGCCUUUACCC | 18 + 1 |
| HEY2_5 | 26781 | GAAAAGGCGUCGGGAUCGA | 26784 | UCGAUCCCGACGCCUUUUC | 18 + 1 |
| HEY2_3 | 26785 | GGGUAAAGGCUACUUUGAC | 26787 | GUCAAAGUAGCCUUUACCC | 19 |
| HEY2_4 | 26786 | CCAUGGCCCACCACCAUCA | 26788 | UGAUGGUGGUGGGCCAUGG | 19 |

TABLE IV

Selected CDKN1B (p27) duplexes

| DsRNA Name | SEQ ID NO: | Sense strand (5' > 3') | SEQ ID NO: | Antisense strand (5' > 3') | Type |
|---|---|---|---|---|---|
| CDKN1B_29 | 26867 | AGCCAAAGUGGCAUGUUUA | 26877 | UAAACAUGCCACUUUGGCU | 18 + 1 |
| CDKN1B_30 | 26868 | GCAUACUGAGCCAAGUAUA | 26878 | UACAUCCUGGCUCUCCUGC | 18 + 1 |
| CDKN1B_31 | 26869 | CAGCGCAAGUGGAAUUUCA | 26879 | UGAAAUUCCACUUGCGCUG | 18 + 1 |
| CDKN1B_33 | 26870 | UGCAUACUGAGCCAAGUAA | 26880 | UAUGCCACUUUGGCUUGUA | 18 + 1 |
| CDKN1B_34 | 26871 | GGAGCGGAUGGACGCCAGA | 26881 | UCUGACAUCCUGGCUCUCC | 18 + 1 |
| CDKN1B_35 | 26872 | AGGGCAGCUUGCCCGAGUA | 26882 | UACUCGGGCAAGCUGCCCU | 18 + 1 |
| CDKN1B_36 | 26873 | GUACUACCUGUGUAUAUAG | 26883 | UUUGGCUCAGUAUGCAACC | 18 + 1 |
| CDKN1B_37 | 26874 | UGCAUACUGAGCCAAGUAU | 26884 | UUACUUGGCUCAGUAUGCA | 18 + 1 |
| CDKN1B_38 | 26875 | GAGUGUCUAACGGGAGCCA | 26885 | UCCGCUGACAUCCUGGCUC | 18 + 1 |

TABLE IV-continued

Selected CDKN1B (p27) duplexes

| DsRNA Name | SEQ ID NO: | Sense strand (5' > 3') | SEQ ID NO: | Antisense strand (5' > 3') | Type |
|---|---|---|---|---|---|
| CDKN1B_40 | 26876 | GCGCAAGUGGAAUUUCGAA | 26886 | UUCGAAAUUCCACUUGCGC | 18 + 1 |
| CDKN1B_3 | 26887 | CGCAUUUGGUGGACCCAAA | 26894 | UUUGGGUCCACCAAAUGCG | 19 |
| CDKN1B_4 | 26888 | GCAAUUAGGUUUUUCCUUA | 26895 | UAAGGAAAAACCUAAUUGC | 19 |
| CDKN1B_10 | 26889 | CAUUGUACUACCUGUGUAU | 26896 | AUACACAGGUAGUACAAUG | 19 |
| CDKN1B_11 | 26890 | GGUUUUUCCUUAUUUGCUU | 26897 | AAGCAAAUAAGGAAAAACC | 19 |
| CDKN1B_18 | 26891 | AGCGCAAGUGGAAUUUCGA | 26898 | UCGAAAUUCCACUUGCGCU | 19 |
| CDKN1B_28 | 26892 | GGUUGCAUACUGAGCCAAA | 26899 | AUCCUGGCUCUCCUGCGCC | 19 |
| CDKN1B_32 | 26893 | AGCCAAAGUGGCAUGUUUU | 26900 | AAAACAUGCCACUUUGGCU | 19 |

TABLE V

Selected NOTCH1 dsRNA

| Name | SEQ ID NO: | Sense strand 5' > 3' | SEQ ID NO: | Antisense strand 5' > 3' | |
|---|---|---|---|---|---|
| NOTCH1_1 | 26901 | CCUUCUACUGCGAGUGUCA | 26906 | UGACACUCGCAGUAGAAGG | 18 + 1 |
| NOTCH1_2 | 26902 | GCUACAACUGCGUGUGUGA | 26907 | UCACACACGCAGUUGUAGC | 18 + 1 |
| NOTCH1_3 | 26903 | UCCUUCUACUGCGAGUGUA | 26908 | UACACUCGCAGUAGAAGGA | 18 + 1 |
| NOTCH1_4 | 26904 | CUCCUUCUACUGCGAGUGA | 26909 | UCACUCGCAGUAGAAGGAG | 18 + 1 |
| NOTCH1_5 | 26905 | CAGCGCAGAUGCCAACAUA | 26910 | UAUGUUGGCAUCUGCGCUG | 18 + 1 |
| NOTCH1_6 | 26911 | ACAACUGCGUGUGUGUCAA | 26912 | UUGACACACGCAGUUGU | 19 |

In some embodiments of the combinations, compositions and methods, the double-stranded oligonucleotide molecule includes a sense strand and an antisense strand selected from the oligonucleotide pairs set forth in Tables I-V. Unless otherwise stated all positions along a sense strand or antisense strand are counted from the 5' to the 3' (5'-3').

In some embodiments the double stranded oligonucleotide includes a particular sense strand and a particular antisense strand set forth in SEQ ID NOS:23-1495 or 26667-26706 (HES1), SEQ ID NOS:1496-2703 or 26707-26732 (HES5), SEQ ID NOS:13004-16621 or 26779-26788 (HEY2), SEQ ID NOS:7444-10533 or 26867-26900 (CDKN1B) or SEQ ID NOS:16622-26666 or 26901-26912 (NOTCH1).

In some embodiments the double stranded nucleic acid molecule has the structure:

wherein each "|" represents base pairing between the ribonucleotides;
wherein each X is any one of A, C, G, U and is independently an unmodified or modified ribonucleotide, an unmodified or modified deoxyribonucleotide or an unconventional moiety;
wherein each of Z and Z' is independently present or absent, but if present is independently 1-5 consecutive nucleotides or non-nucleotide moieties or a combination thereof covalently attached at the 3' terminus of the strand in which it is present; and
wherein z" may be present or absent, but if present is a capping moiety covalently attached at the 5' terminus of the sense strand.

In preferred embodiments the double-stranded oligonucleotide molecule comprises modified ribonucleotides and unconventional moieties.

Chemical Modifications

All analogs of, or modifications to, a nucleotide/oligonucleotide may be employed with the present embodiments, provided that said analogue or modification does not substantially affect the function of the nucleotide/oligonucleotide. The nucleotides can be selected from naturally occurring or synthetic modified bases. Naturally occurring bases include adenine, guanine, cytosine, thymine and uracil. Modified bases of nucleotides are described herein.

In addition, analogues of polynucleotides can be prepared wherein the structure of one or more nucleotide is fundamentally altered and better suited as therapeutic or experimental reagents. An example of a nucleotide analogue is a peptide nucleic acid (PNA) wherein the deoxyribose (or ribose) phosphate backbone in DNA (or RNA is replaced with a polyamide backbone which is similar to that found in peptides. PNA analogues have been shown to be resistant to enzymatic degradation and to have extended stability in vivo and in vitro. Other modifications that can be made to oligonucleotides include polymer backbones, cyclic backbones, acyclic backbones, thiophosphate-D-ribose backbones, triester backbones, thioate backbones, 2'-5' bridged backbone, artificial nucleic acids, morpholino nucleic acids, locked nucleic acid (LNA), glycol nucleic acid (GNA), threose nucleic acid (TNA), arabinoside, and mirror nucleoside (for example, beta-L-deoxynucleoside instead of beta-D-deoxynucleoside). Examples of dsRNA molecules comprising LNA nucleotides are disclosed in Elmen et al., (NAR 2005, 33(1):439-447).

The nucleic acid compounds useful in methods, compositions and combinations disclosed herein can be synthesized using one or more inverted nucleotides, for example inverted thymidine or inverted adenine (see, for example, Takei, et al., 2002, JBC 277(26):23800-06).

The term "unconventional moiety" as used herein refers to abasic ribose moiety, an abasic deoxyribose moiety, a deoxyribonucleotide, a modified deoxyribonucleotide, a mirror nucleotide, a non-base pairing nucleotide analog and a nucleotide joined to an adjacent nucleotide by a 2'-5' internucleotide phosphate bond; C3, C4, C5 and C6 moieties; bridged nucleic acids including LNA and ethylene bridged nucleic acids.

The term "capping moiety" as used herein includes abasic ribose moiety, abasic deoxyribose moiety, modifications of abasic ribose and abasic deoxyribose moieties including 2' O alkyl modifications; inverted abasic ribose and abasic deoxyribose moieties and modifications thereof; C6-imino-Pi; a mirror nucleotide including L-DNA and L-RNA; 5'OMe nucleotide; and nucleotide analogs including 4',5'-methylene nucleotide; 1-(β-D-erythrofuranosyl)nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non bridging methylphosphonate and 5'-mercapto moieties.

Abasic deoxyribose moiety includes for example abasic deoxyribose-3'-phosphate; 1,2-dideoxy-D-ribofuranose-3-phosphate; 1,4-anhydro-2-deoxy-D-ribitol-3-phosphate. Inverted abasic deoxyribose moiety includes inverted deoxyriboabasic; 3',5' inverted deoxyriboabasic 5'-phosphate.

A "mirror" nucleotide is a nucleotide with reversed chirality to the naturally occurring or commonly employed nucleotide, i.e., a mirror image (L-nucleotide) of the naturally occurring (D-nucleotide). The nucleotide can be a ribonucleotide or a deoxyribonucleotide and may further comprise at least one sugar, base and/or backbone modification. U.S. Pat. No. 6,602,858 discloses nucleic acid catalysts comprising at least one L-nucleotide substitution. Mirror nucleotide includes for example L-DNA (L-deoxyriboadenosine-3'-phosphate (mirror dA); L-deoxyribocytidine-3'-phosphate (mirror dC); L-deoxyriboguanosine-3'-phosphate (mirror dG); L-deoxyribothymidine-3'-phosphate (mirror image dT)) and L-RNA (L-riboadenosine-3'-phosphate (mirror rA); L-ribocytidine-3'-phosphate (mirror rC); L-riboguanosine-3'-phosphate (mirror rG); L-ribouracil-3'-phosphate (mirror dU).

In various embodiments of Structure A1 or Structure A2, Z and Z' are absent. In other embodiments Z or Z' is present.

In some embodiments each of Z and/or Z' independently includes a C2, C3, C4, C5 or C6 alkyl moiety, optionally a C3 [propane, —(CH2)3-] moiety or a derivative thereof including propanol (C3-OH/C3OH), propanediol, and phosphodiester derivative of propanediol ("C3Pi"). In preferred embodiments each of Z and/or Z' includes two hydrocarbon moieties and in some examples is C3Pi-C3OH or C3Pi-C3Pi. Each C3 is covalently conjugated to an adjacent C3 via a covalent bond, preferably a phospho-based bond. In some embodiments the phospho-based bond is a phosphorothioate, a phosphonoacetate or a phosphodiester bond.

In specific embodiments, at least one double-stranded oligonucleotide has Structure A1 x=y=19 and Z comprises at least one C3 alkyl overhang. In specific embodiments, at least one double-stranded oligonucleotide has Structure A2 x=y=18 and Z comprises at least one C3 alkyl overhang. In some embodiments the C3-C3 overhang is covalently attached to the 3' terminus of (N)x or (N')y via a covalent linkage, preferably a phosphodiester linkage. In some embodiments the linkage between a first C3 and a second C3 is a phosphodiester linkage. In some embodiments the 3' non-nucleotide overhang is C3Pi-C3Pi. In some embodiments the 3' non-nucleotide overhang is C3Pi-C3Ps. In some embodiments the 3' non-nucleotide overhang is C3Pi-C3OH (OH is hydroxy). In some embodiments the 3' non-nucleotide overhang is C3Pi-C3OH.

In various embodiments the alkyl moiety comprises an alkyl derivative including a C3 alkyl, C4 alkyl, C5 alky or C6 alkyl moiety comprising a terminal hydroxyl, a terminal amino, or terminal phosphate group. In some embodiments the alkyl moiety is a C3 alkyl or C3 alkyl derivative moiety. In some embodiments the C3 alkyl moiety comprises propanol, propylphosphate, propylphosphorothioate or a combination thereof. The C3 alkyl moiety is covalently linked to the 3' terminus of (N')y and/or the 3' terminus of (N)x via a phosphodiester bond. In some embodiments the alkyl moiety comprises propanol, propyl phosphate or propyl phosphorothioate. In some embodiments each of Z and Z' is independently selected from propanol, propyl phosphate propyl phosphorothioate, combinations thereof or multiples thereof in particular 2 or 3 covalently linked propanol, propyl phosphate, propyl phosphorothioate or combinations thereof. In some embodiments each of Z and Z' is independently selected from propyl phosphate, propyl phosphorothioate, propyl phospho-propanol; propyl phospho-propyl phosphorothioate; propylphospho-propyl phosphate; (propyl phosphate)3, (propyl phosphate)2-propanol, (propyl phosphate)2-propyl phosphorothioate. Any propane or propanol conjugated moiety can be included in Z or Z'.

Exemplary 3' terminal non-nucleotide moieties are as follows:

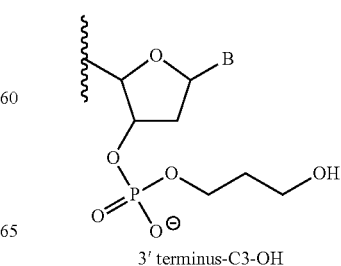

3' terminus-C3-OH

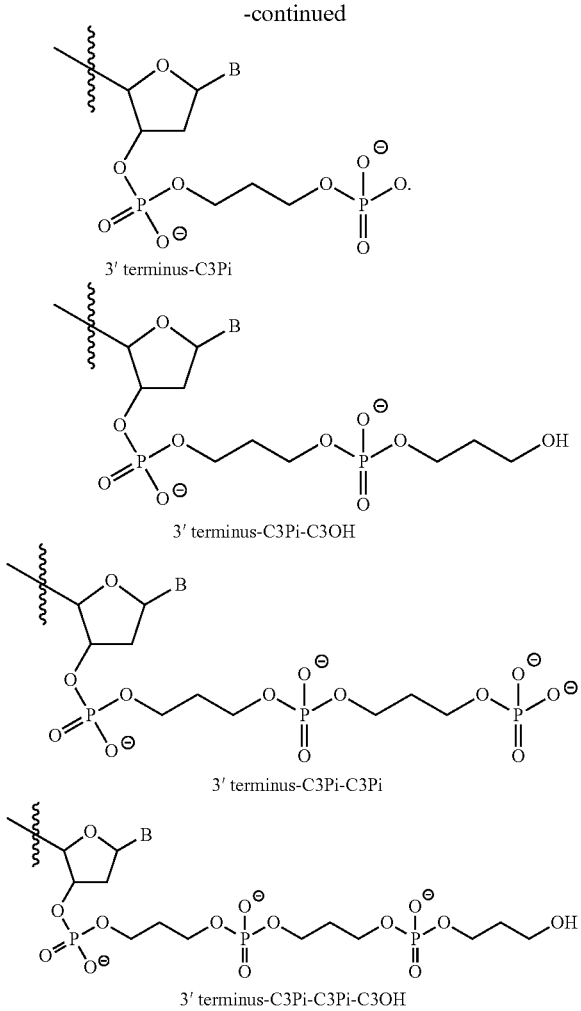

3' terminus-C3Pi

3' terminus-C3Pi-C3OH

3' terminus-C3Pi-C3Pi

3' terminus-C3Pi-C3Pi-C3OH

Indications

The molecules and compositions disclosed herein are useful in the treatment of diseases and disorders of the ear, as well as other diseases and conditions herein described.

The Human Ear

The human ear is comprised of three major structural components: the outer, middle, and inner ears, which function together to convert sound waves into nerve impulses that travel to the brain, where they are perceived as sound. The inner ear also helps to maintain balance.

The anatomy of the middle and the inner ear is well known to those of ordinary skill in the art (see, e.g., *Atlas of Sensory Organs: Functional and Clinical Analysis*, Andrs Csillag, Humana Press (2005), pages 1-82, incorporated herein by reference). In brief, the middle ear consists of the eardrum and a small air-filled chamber containing a sequence of three tiny bones known as the ossicles, which link the eardrum to the inner ear.

The inner ear (labyrinth) is a complex structure consisting of the cochlea, which is the organ of hearing and the vestibular system, the organ of balance. The vestibular system consists of the saccule and the utricle, which determine position sense, and the semicircular canals, which help maintain balance.

The cochlea houses the organ of Corti, which consists, in part, of about 20,000 specialized sensory cells, called "inner ear hair cells" or "hair cells". These cells have small hairline projections (cilia) that extend into the cochlear fluid. Sound vibrations transmitted from the ossicles in the middle ear to the oval window in the inner ear cause the fluid and cilia to vibrate. Hair cells in different parts of the cochlea vibrate in response to different sound frequencies and convert the vibrations into nerve impulses which are sent to the brain for processing and interpretation. The inner ear hair cells (IHC) are surrounded by inner ear support cells. Supporting cells underlie, at least partially surround, and physically support sensory hair cells within the inner ear. Representative examples of support cells include inner rod (pillar cells), outer rod (pillar cells), inner phalangeal cells, outer phalangeal cells (of Deiters), cells of Held, cells of Hensen, cells of Claudius, cells of Boettcher, interdental cells and auditory teeth (of Huschke).

The spiral ganglion is the group of nerve cells that send a representation of sound from the cochlea to the brain. The cell bodies of the spiral ganglion neurons are found in the spiral structure of the cochlea and are part of the central nervous system. Their dendrites make synaptic contact with the base of hair cells, and their axons are bundled together to form the auditory portion of the eighth cranial nerve (vestibulocochlear nerve).

Hearing Loss

Auditory hair cells are sensory receptors located in the organ of Corti of the cochlea involved in detecting sound. The cochlear hair cells come in two anatomically and functionally distinct types: the outer and inner hair cells. Auditory hair cells convert sound information into electrical signals that are sent via nerve fibers to the brain and processed.

Vestibular hair cells, located in the vestibular organs of the inner ear (utricle, saccule, ampullae), detect changes in head position and convey this information to the brain to help maintain balance posture and eye position.

In the absence of auditory hair cells, sound waves are not converted into neural signals and hearing deficits ensue, for example, decreased hearing sensitivity, i.e. sensorineural hearing loss. In the absence of vestibular hair cells, balance deficits ensue.

Despite the protective effect of the acoustic reflex, loud noise can damage and destroy hair cells. Irreversible hair cell death is elicited by metabolic or biochemical changes in the hair cells that involve reactive oxygen species (ROS). Exposure to certain drugs and continued exposure to loud noise, inter alia, cause progressive damage, eventually resulting in ringing in the ears (tinnitus) and or hearing loss.

Acquired hearing loss can be caused by several factors including exposure to harmful noise levels, exposure to ototoxic drugs such as cisplatin and aminoglycoside antibiotics and aging.

U.S. Ser. No. 11/655,610 to the assignee of the present invention relates to methods of treating hearing impairment by inhibiting a pro-apoptotic gene in general and p53 in particular. International Patent Publication No. WO 2005/119251 relates to methods of treating deafness. International Patent Publication No. WO/2005/055921 relates to foam compositions for treatment of ear disorders. U.S. Pat. No. 7,087,581 relates to methods of treating diseases and disorders of the inner ear. PCT Publication No. WO 2009/147684, assigned to the assignee of the present application, and incorporated herein by reference in its entirety discloses certain compounds and compositions for treating otic disorders and diseases.

Ear Disorders

The present disclosure is directed, inter alia, to compositions, combinations and methods useful in treating a patient suffering from or at risk of various ear disorders. Ear disorders include hearing loss induced for example by ototoxins, excessive noise or ageing. Middle and inner ear disorders produce many of the same symptoms, and a disorder of the middle ear may affect the inner ear and vice versa.

In addition to hearing loss, ear disorders include myringitis, an eardrum infection caused by a variety of viruses and bacteria; temporal bone fracture for example due to a blow to the head; auditory nerve tumors (acoustic neuroma, acoustic neurinoma, vestibular schwannoma, eighth nerve tumor).

In various embodiments, the methods, combinations and compositions disclosed herein are useful in treating various conditions of hearing loss. Without being bound by theory, the hearing loss may be due to apoptotic inner ear hair cell damage or loss (Zhang et al., Neuroscience 2003. 120:191-205; Wang et al., J. Neuroscience 23((24):8596-8607), wherein the damage or loss is caused by infection, mechanical injury, loud sound (noise), aging (presbycusis), or chemical-induced ototoxicity.

By "ototoxin" in the context disclosed herein is meant a substance that through its chemical action injures, impairs or inhibits the activity of the sound receptors component of the nervous system related to hearing, which in turn impairs hearing (and/or balance). In the context of the present invention, ototoxicity includes a deleterious effect on the inner ear hair cells. Ototoxic agents that cause hearing impairments include, but are not limited to, neoplastic agents such as vincristine, vinblastine, cisplatin and cisplatin-like compounds, taxol and taxol-like compounds, dideoxy-compounds, e.g., dideoxyinosine; alcohol; metals; industrial pollutants involved in occupational or environmental exposure; contaminants of food or medicinals; and over-doses of vitamins or therapeutic drugs, e.g., antibiotics such as penicillin or chloramphenicol, and megadoses of vitamins A, D, or B6, salicylates, quinines and loop diuretics. By "exposure to an ototoxic agent" is meant that the ototoxic agent is made available to, or comes into contact with, a mammal. Exposure to an ototoxic agent can occur by direct administration, e.g., by ingestion or administration of a food, medicinal, or therapeutic agent, e.g., a chemotherapeutic agent, by accidental contamination, or by environmental exposure, e.g., aerial or aqueous exposure. Typically, treatment is performed to prevent or reduce ototoxicity, especially resulting from or expected to result from administration of therapeutic drugs. Preferably a composition comprising a therapeutically effective amount of a chemically modified siRNA compound of the invention is given immediately after the exposure to prevent or reduce the ototoxic effect. More preferably, treatment is provided prophylactically, either by administration of the pharmaceutical composition of the invention prior to or concomitantly with the ototoxic pharmaceutical or the exposure to the ototoxin. Incorporated herein by reference are chapters 196, 197, 198 and 199 of The Merck Manual of Diagnosis and Therapy, 14th Edition, (1982), Merck Sharp & Dome Research Laboratories, N.J. and corresponding chapters in the most recent 16th edition, including Chapters 207 and 210) relating to description and diagnosis of hearing and balance impairments.

Accordingly, in one aspect provided are methods, combinations and pharmaceutical compositions for treating a mammal, preferably human, to prevent, reduce, or treat a hearing impairment, disorder or imbalance, preferably an ototoxin-induced hearing condition, by administering to a mammal in need of such treatment a combination or composition comprising inhibitors of target genes as disclosed herein. Some embodiments are directed to methods for treating a hearing disorder or impairment wherein the ototoxicity results from administration of a therapeutically effective amount of an ototoxic pharmaceutical drug. Typical ototoxic drugs are chemotherapeutic agents, e.g. antineoplastic agents, and antibiotics. Other possible candidates include loop-diuretics, quinines or a quinine-like compound, PDE-5 inhibitors and salicylate or salicylate-like compounds.

Ototoxicity is a dose-limiting side effect of antibiotic administration. From 4 to 15% of patients receiving 1 gram per day for greater than 1 week develop measurable hearing loss, which slowly becomes worse and can lead to complete permanent deafness if treatment continues. Ototoxic aminoglycoside antibiotics include but are not limited to neomycin, paromomycin, ribostamycin, lividomycin, kanamycin, amikacin, tobramycin, viomycin, gentamicin, sisomicin, netilmicin, streptomycin, dibekacin, fortimicin, and dihydrostreptomycin, or combinations thereof. Particular antibiotics include neomycin B, kanamycin A, kanamycin B, gentamicin C1, gentamicin C1a, and gentamicin C2, and the like that are known to have serious toxicity, particularly ototoxicity and nephrotoxicity, which reduce the usefulness of such antimicrobial agents (see Goodman and Gilman's The Pharmacological Basis of Therapeutics, 6th ed., A. Goodman Gilman et al., eds; Macmillan Publishing Co., Inc., New York, pp. 1169-71 (1980)).

Ototoxicity is also a serious dose-limiting side-effect for anti-cancer agents. Ototoxic neoplastic agents include but are not limited to vincristine, vinblastine, cisplatin and cisplatin-like compounds and taxol and taxol-like compounds. Cisplatin-like compounds include carboplatin (Paraplatin®), tetraplatin, oxaliplatin, aroplatin and transplatin inter alia and are platinum based chemotherapeutics.

Diuretics with known ototoxic side-effect, particularly "loop" diuretics include, without being limited to, furosemide, ethacrylic acid, and mercurials.

Ototoxic quinines include but are not limited to synthetic substitutes of quinine that are typically used in the treatment of malaria. In some embodiments the hearing disorder is side-effect of inhibitors of type 5 phosphodiesterase (PDE-5), including sildenafil (Viagra®), vardenafil (Levitra®) and tadalafil (Clalis).

Salicylates, such as aspirin, are the most commonly used therapeutic drugs for their anti-inflammatory, analgesic, anti-pyretic and anti-thrombotic effects. Unfortunately, they too have ototoxic side effects. They often lead to tinnitus ("ringing in the ears") and temporary hearing loss. Moreover, if the drug is used at high doses for a prolonged time, the hearing impairment can become persistent and irreversible.

In some embodiments of the methods provided herein, the subject is a mammal suffering of infection and treated by administration of an aminoglycoside antibiotic. The methods disclosed herein improve the outcome of such treatment by reducing or preventing ototoxin-induced hearing impairment associated with the antibiotic.

The methods, combinations and pharmaceutical compositions described herein are also effective in the treatment of acoustic trauma or mechanical trauma, preferably acoustic or mechanical trauma that leads to inner ear hair cell loss. With more severe exposure, injury can proceed from a loss of adjacent supporting cells to complete disruption of the organ of Corti. Death of the sensory cell can lead to progressive Wallerian degeneration and loss of primary auditory nerve fibers. The methods, combinations and compositions provided herein are useful in treating acoustic trauma caused by a single exposure to an extremely loud sound, or following long-term exposure to everyday loud sounds above 85 decibels, for treating mechanical inner ear trauma, for example, resulting from the insertion of an electronic device into the inner ear or for preventing or minimizing the damage to inner ear hair cells associated with the operation.

Another type of hearing loss is presbycusis, which is hearing loss that gradually occurs in most individuals as they age. About 30-35 percent of adults between the ages of 65 and 75 years and 40-50 percent of people 75 and older experience hearing loss. The methods, combinations and compositions disclosed herein are useful in preventing, reducing or treating the incidence and/or severity of inner ear disorders and hearing impairments associated with presbycusis.

Acoustic Trauma

Acoustic trauma is a type of hearing loss that is caused by prolonged exposure to loud noises. Without wishing to be bound to theory, exposure to loud noise causes the hair cells on the cochlea to become less sensitive. With more severe exposure, injury can proceed from a loss of adjacent supporting cells to complete disruption of the organ of Corti. Death of the sensory cell can lead to progressive Wallerian degeneration and loss of primary auditory nerve fibers. Disclosed herein are, inter alia, combinations, pharmaceutical compositions and methods useful in attenuating hearing loss due to acoustic trauma. In certain embodiments of the methods, combinations and compositions, dsRNA molecules that target HES1, HES5, and HEY2 are used for treating or preventing acoustic trauma in a subject exposed to acoustic trauma., In certain embodiments of the methods, combinations and compositions, dsRNA molecules that target CDKN1B, NOTCH1 and HEY2 are used for treating or preventing acoustic trauma in a subject exposed to acoustic trauma.

In certain embodiments, provided herein are methods of treating a subject suffering from or at risk of an ear disorder which comprises topically administering to the canal of the subject's ear a pharmaceutical composition comprising inhibitors to target genes associated with the disorder, such as dsRNA inhibitors, in an amount effective to treat the subject, and a pharmaceutically acceptable excipient or mixtures thereof, thereby treating the subject. In certain embodiments, provided herein are methods of treating a subject suffering from or at risk of an ear disorder which comprises transtympanically administering to the canal of the subject's ear a pharmaceutical composition comprising inhibitors to target genes associated with the disorder, such as oligonucleotide inhibitors, in an amount effective to treat the subject, and a pharmaceutically acceptable excipient or mixtures thereof, thereby treating the subject. In one embodiment, the pharmaceutical composition is delivered via a posterior semicircular canalostomy. In one embodiment, the pharmaceutical composition is delivered as ear drops. In another embodiment the pharmaceutical composition is delivered by a pump.

In some embodiments, the pharmaceutical composition is applied to the ear canal when the subject's head is tilted to one side and the treated ear is facing upward. In some embodiments, the pharmaceutical composition is applied to the ear using a receptacle for eardrops, for example using a dropper of for example, 10-100 microliter per drop, or a wick.

In some embodiments an ear disorder relates to chemical-induced hearing loss; for example hearing loss induced by inter alia cisplatin and its analogs; aminoglycoside antibiotics, quinine and its analogs; salicylate and its analogs; phosphodiesterase type 5 (PDE5) inhibitors or loop-diuretics. In some embodiments the ear disorder refers to noise-induced hearing loss. In other embodiments the ear disorder is age related hearing loss.

Without being bound by theory, inhibition of HES1, HES5, HEY2, CDKN1B or NOTCH1 results in regeneration of or protection of otic hair (sensory) cells of the inner ear, optionally via an increase in Atoh1 expression. The methods, compositions and combinations as disclosed herein, are useful in treating, ameliorating or preventing any disease, disorder or injury in which promoting proliferation of supporting cells of the inner ear or of outer hair cells or of inner hair cells in the cochlea is required. In various embodiments the methods, compositions and combinations provided herein are useful in treating hearing and balance disorders, such as, without being limited to, ototoxin-induced hearing loss, hearing loss associated with Meniere's disease, and trauma-induced hearing loss, such as acoustic trauma and pressure trauma, including blasts and surgical procedures in the inner and/or middle ear.

Diseases and Disorders of the Vestibular System

In various embodiments the nucleic acid compounds and pharmaceutical compositions disclosed herein are useful for treating disorders and diseases affecting the vestibular system in which expression of HES1, HES5, and HEY2, or CDKN1B, NOTCH1 and HEY2 is detrimental, for example Meniere's Disease. The vestibular sensory system in most mammals, including humans, contributes to balance, and to a sense of spatial orientation and stability. Together with the cochlea it constitutes the labyrinth of the inner ear. The vestibular system comprises two components: the semicircular canal system, which indicate rotational movements; and the otoliths, which indicate linear accelerations.

The primary morbidity associated with Meniere's disease is the debilitating nature of vertigo and the progressive hearing loss. Current therapies have not been successful at preventing progression of neuronal degeneration and associated hearing loss. A therapeutic treatment, which would protect the neurons of the inner ear including the vestibulocochlear nerve from damage and/or induce regeneration of the vestibulocochlear nerve and thereby attenuate or prevent hearing loss in Meniere's patients would be highly desirable.

In certain aspects and embodiments, the combinations, compositions, methods, commercial packages and kits provided herein are useful in treating subjects at risk of or suffering from Meniere's disease.

In conclusion, there are no effective modes of therapy for the prevention and/or treatment of the conditions disclosed herein. Treatments that are available suffer from, inter alia, the drawbacks of severe side effects due to the lack of selective targeting and there remains a need therefore to develop novel compositions and methods of treatment for these purposes.

In various embodiments the combinations and pharmaceutical compositions provided herein are useful in treating or preventing various diseases, disorders and injury that affect the ear, such as, without being limited to, the diseases, disorders and injury that are disclosed herein below. Without being bound by theory, it is believed that the combinations/compositions disclose herein prevent death or various types of cells within the ear and/or promote differentiation of supporting cells within the inner ear into otic sensory cells.

Pharmaceutical Compositions

Provided are compositions, combinations and methods for down-regulation of expression of HES1, HES5 and HEY2, or for down-regulation of expression of CDKN1B, HEY2 and NOTCH1. In certain embodiments, the compositions, combinations and methods use small nucleic acid molecules, such as short interfering nucleic acid (siNA), interfering RNA (RNAi), short interfering RNA (siRNA), double-stranded RNA (dsRNA), micro-RNA (miRNA), and short hairpin RNA (shRNA) molecules capable of mediating down-regulation of HES1, HES5, HEY2, CDKN1B, or NOTCH1 gene expression or that mediate RNA interference against HES1, HES5, HEY2, CDKN1B, or NOTCH1 gene expression.

While it may be possible for the molecules disclosed herein to be administered as the raw chemical, it is preferable to present them as a pharmaceutical composition. Accordingly provided is a pharmaceutical composition comprising one or more of the dsRNA molecules disclosed herein or pharmacological salts thereof; and a pharmaceutically acceptable carrier. The composition may comprise a mixture of two or three different nucleic acid compounds.

Compositions, methods and kits provided herein may include one or more nucleic acid molecules (e.g., dsRNA) and methods that independently or in combination modulate (e.g., down-regulate) the expression of HES1, HES5, HEY2, CDKN1B or NOTCH1 protein and/or genes encoding HES1, HES5, HEY2, CDKN1B or NOTCH1 protein, proteins and/or genes associated with the maintenance and/or development of diseases, conditions or disorders associated with HES1, HES5, HEY2, CDKN1B or NOTCH1, particularly disorders associated with the ear. The description of the various aspects and embodiments is provided with reference to exemplary genes HES1, HES5, HEY2, CDKN1B or NOTCH1. However, the various aspects and embodiments are also directed to other related genes, such as homolog genes and transcript variants, and polymorphisms (e.g., single nucleotide polymorphism, (SNPs)) associated with certain HES1, HES5, HEY2, CDKN1B or NOTCH1 genes. As such, the various aspects and embodiments are also directed to other genes that are involved in HES1, HES5, HEY2, CDKN1B or NOTCH1 mediated pathways of signal transduction or gene expression that are involved, for example, in the maintenance or development of diseases, traits, or conditions described herein. These additional genes can be analyzed for target sites using the methods described for the HES1, HES5, HEY2, CDKN1B or NOTCH1 gene herein. Thus, the down-regulation of other genes and the effects of such modulation of the other genes can be performed, determined, and measured as described herein.

Further provided is a pharmaceutical composition comprising at least one compound of the invention covalently or non-covalently bound to one or more compounds of the invention in an amount effective to down regulate HES1, HES5, HEY2, CDKN1B, or NOTCH1 expression; and a pharmaceutically acceptable carrier. Further provided are nucleic acid compounds which are processed intracellularly by endogenous cellular complexes to produce one or more oligoribonucleotides useful in accordance with the aspects and embodiments described herein.

Further provided is a pharmaceutical composition comprising a pharmaceutically acceptable carrier and one or more of the compounds useful in methods disclosed herein in an amount effective to inhibit expression in a cell of human HES1, HES5, HEY2, CDKN1B or NOTCH1, the compound comprising a sequence which is substantially complementary to a consecutive sequence selected from a sequence in HES1 mRNA, HES5 mRNA, HEY2 mRNA, CDKN1B mRNA or NOTCH1 mRNA.

Substantially complementary refers to complementarity of greater than about 84%, to another sequence. For example in a duplex region consisting of 19 base pairs one mismatch results in 94.7% complementarity, two mismatches results in about 89.5% complementarity and 3 mismatches results in about 84.2% complementarity, rendering the duplex region substantially complementary. Accordingly substantially identical refers to identity of greater than about 84%, to another sequence.

Additionally, provided herein are methods of preventing, treating, or delaying of progression of a hearing disorder, a hearing loss, and/or a balance impairment, or of preventing the loss of otic (sensory) hair cells of the inner ear in a subject, comprising inhibiting the expression of HES1, HES5, HEY2, CDKN1B or NOTCH1 gene by at least 20%, by at least 30% by at least 40%, preferably by 50%, 60% or 70%, more preferably by 75%, 80% or 90% as compared to a control comprising contacting an mRNA transcript of the respective gene with a HES1 inhibitor, a HES5 inhibitor, a HEY2 inhibitor, a CDKN1B inhibitor or a NOTCH1 inhibitor, In various embodiments as provided herein, the inhibitor is an oligoribonucleotide compound. Compositions, combinations and methods disclosed herein inhibit/down-regulate the HES1, HES5, HEY2, CDKN1B, or NOTCH1 gene, whereby the inhibition/down-regulation is selected from the group comprising inhibition/down-regulation of gene function, inhibition/down-regulation of polypeptide and inhibition/down-regulation of mRNA expression.

In certain embodiments, compositions, combinations and methods provided herein include a double-stranded short interfering nucleic acid (siNA) compound that down-regulates expression of a HES1, HES5, HEY2, CDKN1B or NOTCH1 gene (e.g., the mRNA coding sequence for human HES1, HES5, HEY2, CDKN1B or NOTCH1 exemplified by SEQ ID NO:1, 2, 10, 7 or 11, where the nucleic acid molecule includes about 18 to about 49 base pairs.

In some embodiments, a nucleic acid disclosed herein may be used to inhibit the expression of the HES1, HES5, HEY2, CDKN1B or NOTCH1 gene or a HES1, HES5, HEY2, CDKN1B, or NOTCH1 gene family where the genes or gene family sequences share sequence homology. Such homologous sequences can be identified as is known in the art, for example using sequence alignments. Nucleic acid molecules can be designed to target such homologous sequences, for example using perfectly complementary sequences or by incorporating non-canonical base pairs, for example mismatches and/or wobble base pairs, that can provide additional target sequences. In instances where mismatches are identified, non-canonical base pairs (for example, mismatches and/or wobble bases) can be used to generate nucleic acid molecules that target more than one gene sequence. In a non-limiting example, non-canonical base pairs such as UU and CC base pairs are used to generate nucleic acid molecules that are capable of targeting sequences for differing HES1, HES5, HEY2, CDKN1B, or NOTCH1 targets that share sequence homology. As such, one advantage of using dsRNAs disclosed herein is that a single nucleic acid can be designed to include nucleic acid sequence that is complementary to the nucleotide sequence that is conserved between the homologous genes. In this approach, a single nucleic acid can be used to inhibit expression of more than one gene instead of using more than one nucleic acid molecule to target the different genes.

Nucleic acid molecules may be used to target conserved sequences corresponding to a gene family or gene families such as HES1, HES5, HEY2, CDKN1B, or NOTCH1 family genes. As such, nucleic acid molecules targeting multiple HES1, HES5, HEY2, CDKN1B, or NOTCH1 targets can provide increased therapeutic effect. In addition, nucleic acid can be used to characterize pathways of gene function in a variety of applications. For example, nucleic acid molecules can be used to inhibit the activity of target gene(s) in a pathway to determine the function of uncharacterized gene(s) in gene function analysis, mRNA function analysis, or translational analysis. The nucleic acid molecules can be used to determine potential target gene pathways involved in various diseases and conditions toward pharmaceutical development. The nucleic acid molecules can be used to understand pathways of gene expression involved in, for example ear disorders.

In various embodiments of the compositions, combinations and methods provided herein, nucleic acid compounds inhibit the HES1, HES5, HEY2, CDKN1B, or NOTCH1 polypeptide, whereby the inhibition is selected from the group comprising inhibition of function (which may be examined by an enzymatic assay or a binding assay with a known interactor of the native gene/polypeptide, inter alia), down-regulation of protein or inhibition of protein (which may be examined by Western blotting, ELISA or immuno-precipitation, inter alia) and inhibition of mRNA expression (which may be examined by Northern blotting, quantitative RT-PCR, in-situ hybridisation or microarray hybridisation, inter alia).

In certain embodiments, the compositions, combinations and methods provided herein include a nucleic acid molecule having RNAi activity against HES1, HES5, HEY2, CDKN1B, or NOTCH1 RNA, where the nucleic acid molecule includes a sequence complementary to any RNA having HES1, HES5, HEY2, CDKN1B or NOTCH1 encoding sequence, such as that sequence set forth in SEQ ID NO:1, 2, 10, 7 or 11. In another embodiment, a nucleic acid molecule may have RNAi activity against HES1, HES5, HEY2, CDKN1B, or NOTCH1 RNA, where the nucleic acid molecule includes a sequence complementary to an RNA having variant HES1, HES5, HEY2, CDKN1B or NOTCH1 encoding sequence, for example mutatations in HES1, HES5, HEY2, CDKN1B or NOTCH1 genes not shown in SEQ ID NO:1, 2, 10, 7 or 11 but known in the art to be associated with the onset and/or maintenance and/or development of any of the disorders disclosed herein, for example a SNP. Chemical modifications as described herein can be applied to any nucleic acid construct disclosed herein. In another embodiment, a nucleic acid molecule disclosed herein includes a nucleotide sequence that can interact with nucleotide sequence of a HES1, HES5, HEY2, CDKN1B or NOTCH1 gene and thereby mediate down-regulation or silencing of HES1, HES5, HEY2, CDKN1B or NOTCH1 gene expression, for example, wherein the nucleic acid molecule mediates regulation of HES1, HES5, HEY2, CDKN1B or NOTCH1 gene expression by cellular processes that modulate the chromatin structure or methylation patterns of the gene and prevent transcription of the gene.

Delivery and Formulations

The inhibitors useful in accordance with the aspects and embodiments disclosed herein (e.g. dsRNA molecules) may be delivered to the ear of a subject by direct application of a pharmaceutical composition to the outer ear; by transtympanic injection, by a pump or by ear drops. In some embodiments the pharmaceutical composition is applied to the ear canal. Delivery to the ear may also be refereed to as aural or otic delivery comprising, e.g. siRNA; a penetration enhancer and a pharmaceutically acceptable vehicle.

In various embodiments, inhibitors, e.g. nucleic acid molecules, as disclosed herein may be delivered to the target tissue by direct application of the naked molecules prepared with a carrier or a diluent.

The terms "naked nucleic acid" or "naked dsRNA" or "naked siRNA" refers to nucleic acid molecules that are free from any delivery vehicle that acts to assist, promote or facilitate entry into the cell, including viral sequences, viral particles, liposome formulations, lipofectin or precipitating agents and the like. For example, dsRNA in PBS is "naked dsRNA".

In various embodiments, inhibitors, e.g. nucleic acid molecules disclosed herein, may be delivered or administered directly with a carrier or diluent that acts to assist, promote or facilitate entry to the cell, including viral vectors, viral particles, liposome formulations, lipofectin or precipitating agents and the like.

A nucleic acid molecule may include a delivery vehicle, including liposomes, for administration to a subject, carriers and diluents and their salts, and/or can be present in pharmaceutically acceptable formulations. In some embodiments, the dsRNA molecules of disclosed herein are delivered in liposome formulations and lipofectin formulations and the like and can be prepared by methods well known to those skilled in the art. Such methods are described, for example, in U.S. Pat. Nos. 5,593,972, 5,589,466, and 5,580,859, which are herein incorporated by reference.

Delivery systems aimed specifically at the enhanced and improved delivery of siRNA into mammalian cells have been developed, (see, for example, Shen et al., FEBS Let. 2003, 539:111-114; Xia et al., Nat. Biotech. 2002, 20:1006-1010; Reich et al., Mol. Vision. 2003, 9: 210-216; Sorensen et al., J. Mol. Biol. 2003. 327: 761-766; Lewis et al., Nat. Gen. 2002, 32: 107-108 and Simeoni et al., NAR 2003, 31,11: 2717-2724). siRNA has recently been successfully used for inhibition of gene expression in primates (see for example, Tolentino et al., Retina 24(4):660).

Delivery of naked or formulated RNA molecules to the ear, optionally the inner ear, is accomplished, inter alia, by transtympanic injection or by administration of the desired compounds formulated as an ear drop. Otic compositions comprising dsRNA are disclosed in US Publication No. 20110142917, to the assignee of the present application and incorporated herein by reference in its entirety.

Polypeptides that facilitate introduction of nucleic acid into a desired subject are known in the art, e.g. such as those described in US. Application Publication No. 20070155658 (e.g., a melamine derivative such as 2,4,6-Triguanidino Traizine and 2,4,6-Tramidosarcocyl Melamine, a polyarginine polypeptide, and a polypeptide including alternating glutamine and asparagine residues).

The pharmaceutically acceptable carriers, solvents, diluents, excipients, adjuvants and vehicles as well as implant carriers generally refer to inert, non-toxic solid or liquid fillers, diluents or encapsulating material not reacting with the active ingredients of the invention and they include liposomes and microspheres. Examples of delivery systems useful in the present invention include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

In a particular embodiment, the administration comprises transtympanic administration. In another embodiment the administration comprises topical or local administration. The compounds are administered as eardrops, ear cream, ear ointment, a solution, a foam, a mousse or any of the above in combination with a delivery device. Implants of the compounds are also useful. Liquid forms are prepared as drops or for continuous application. The liquid compositions include aqueous solutions, with and without organic co-solvents, aqueous or oil suspensions, emulsions with edible oils, as well as similar pharmaceutical vehicles. These compositions may also be injected transtympanically. Eardrops may also be referred to as otic drops or aural drops. In a preferred embodiment, the ear drops remain in the ear canal for about 30 min in order to prevent leakage of the drops out of the canal. It is thus preferable that the subject receiving the drops keep his head on the side with the treated ear facing upward to prevent leakage of the drop out of the canal.

Methods for the delivery of nucleic acid molecules are described in Akhtar et al., Trends Cell Bio., 2: 139 (1992); Delivery Strategies for Antisense Oligonucleotide Therapeutics, ed. Akhtar, (1995), Maurer et al., Mol. Membr. Biol., 16: 129-140 (1999); Hofland and Huang, Handb. Exp. Pharmacol., 137: 165-192 (1999); and Lee et al., ACS Symp. Ser., 752: 184-192 (2000); U.S. Pat. Nos. 6,395,713; 6,235,310; 5,225,182; 5,169,383; 5,167,616; 4,959217; 4,925,678; 4,487,603; and 4,486,194 and Sullivan et al., PCT WO 94/02595; PCT WO 00/03683 and PCT WO 02/08754; and U.S. Patent Application Publication No. 2003077829. These protocols can be utilized for the delivery of virtually any nucleic acid molecule. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see e.g., Gonzalez et al., Bioconjugate Chem., 10: 1068-1074 (1999); Wang et al., International PCT publication Nos. WO 03/47518 and WO 03/46185), poly(lactic-co-glycolic)acid (PLGA) and PLCA microspheres (see for example U.S. Pat. No. 6,447,796 and U.S. Application Publication No. 2002130430), biodegradable nanocapsules, and bioadhesive microspheres, or by proteinaceous vectors (O'Hare and Normand, International PCT Publication No. WO 00/53722). Alternatively, the nucleic acid/vehicle combination is locally delivered by direct injection or by use of an infusion pump. Direct injection of the nucleic acid molecules of the invention, whether intravitreal, subcutaneous, transtympanic, intramuscular, or intradermal, can take place using standard needle and syringe methodologies, or by needle-free technologies such as those described in Conry et al., Clin. Cancer Res., 5: 2330-2337 (1999) and Barry et al., International PCT Publication No. WO 99/31262. The molecules of the instant invention can be used as pharmaceutical agents. Pharmaceutical agents prevent, modulate the occurrence, or treat or alleviate a symptom to some extent (preferably all of the symptoms) of a disease state in a subject. In one specific embodiment of this invention topical and transdermal formulations may be selected.

The pharmaceutical compositions and combinations disclosed herein are administered and dosed in accordance with good medical practice, taking into account the clinical condition of the individual subject, the disease to be treated, the site and method of administration, scheduling of administration, patient age, sex, body weight and other factors known to medical practitioners.

In another embodiment, the administration comprises topical or local administration such as via eardrops or ointment. In a non-limiting example, dsRNA compounds that target HES1, HES5, HEY2, CDKN1B, or NOTCH1 are useful in treating a subject suffering from damage to the ear, wherein the dsRNA compounds are delivered to the ear via topical delivery (e.g., ear drops or ointments). Nucleic acid molecules may be complexed with cationic lipids, packaged within liposomes, or otherwise delivered to target cells or tissues. The nucleic acid or nucleic acid complexes can be locally administered to relevant tissues ex vivo, or in vivo through direct dermal application, transdermal application, or injection, with or without their incorporation in biopolymers. Preferred oligonucleotides useful in generating dsRNA molecules are disclosed herein.

Delivery systems may include surface-modified liposomes containing poly (ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011).

Nucleic acid molecules may be formulated or complexed with polyethylenimine (e.g., linear or branched PEI) and/or polyethylenimine derivatives, including for example polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives, grafted PEIs such as galactose PEI, cholesterol PEI, antibody derivatized PEI, and polyethylene glycol PEI (PEG-PEI) derivatives thereof (see for example Ogris et al., 2001, AAPA Pharm Sci, 3, 1-11; Furgeson et al., 2003, Bioconjugate Chem., 14, 840-847; Kunath et al., 2002, Pharmaceutical Research, 19, 810-817; Choi et al., 2001, Bull. Korean Chem. Soc., 22, 46-52; Bettinger et al., 1999, Bioconjugate Chem., 10, 558-561; Peterson et al., 2002, Bioconjugate Chem., 13, 845-854; Erbacher et al., 1999, Journal of Gene Medicine Preprint, 1, 1-18; Godbey et al., 1999, PNAS USA, 96, 5177-5181; Godbey et al., 1999, Journal of Controlled Release, 60, 149-160; Diebold et al., 1999, Journal of Biological Chemistry, 274, 19087-19094; Thomas and Klibanov, 2002, PNAS USA, 99, 14640-14645; Sagara, U.S. Pat. No. 6,586,524 and US Patent Application Publication No. 20030077829).

Nucleic acid molecules may be complexed with membrane disruptive agents such as those described in U.S. Patent Application Publication No. 20010007666. The membrane disruptive agent or agents and the nucleic acid molecule may also be complexed with a cationic lipid or helper lipid molecule, such as those lipids described in U.S. Pat. No. 6,235,310.

Delivery systems may include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer. Non-limiting examples of liposomes which can be used with the compounds of this invention include the following: (1) CellFectin, 1:1.5 (M/M) liposome formulation of the cationic lipid N,NI,NII,NIII-tetramethyl-N,NI,NII,NIII-tetrapalmit-y-spermine and dioleoyl phosphatidylethanolamine (DOPE) (GIBCO BRL); (2) Cytofectin GSV, 2:1 (M/M) liposome formulation of a cationic lipid and DOPE (Glen Research); (3) DOTAP (N-[1-(2,3-dioleoyloxy)-N,N,N-tri-methyl-ammoniummethylsulfate) (Boehringer Manheim); and (4) Lipofectamine, 3:1 (M/M) liposome formulation of the polycationic lipid DOSPA, the neutral lipid DOPE (GIBCO BRL) and Di-Alkylated Amino Acid (DiLA2).

Delivery systems may include patches, tablets, suppositories, pessaries, gels, aqueous and nonaqueous solutions, lotions and creams, and can contain excipients such as solubilizers and enhancers (e.g., propylene glycol, bile salts and amino acids), and other vehicles (e.g., polyethylene glycol, glycerol, fatty acid esters and derivatives, and hydrophilic polymers such as hydroxypropylmethylcellulose and hyaluronic acid).

Nucleic acid molecules may include a bioconjugate, for example a nucleic acid conjugate as described in Vargeese et al., U.S. Ser. No. 10/427,160; U.S. Pat. No. 6,528,631; U.S. Pat. No. 6,335,434; U.S. Pat. No. 6,235,886; U.S. Pat. No. 6,153,737; U.S. Pat. No. 5,214,136; U.S. Pat. No. 5,138,045.

Compositions, combinations, methods and kits disclosed herein may include an expression vector that includes a nucleic acid sequence encoding at least one nucleic acid molecule disclosed herein in a manner that allows expression of the nucleic acid molecule. Methods of introducing nucleic acid molecules or one or more vectors capable of expressing the strands of dsRNA into the environment of the cell will depend on the type of cell and the make up of its environment. The nucleic acid molecule or the vector construct may be directly introduced into the cell (i.e., intracellularly); or introduced extracellularly into a cavity, interstitial space, into the circulation of an organism, introduced orally, or may be introduced by bathing an organism or a cell in a solution containing dsRNA. The cell is preferably a mammalian cell; more preferably a human cell. The nucleic acid molecule of the expression vector can include a sense region and an antisense region. The antisense region can include a sequence complementary to a RNA or DNA sequence encoding HES1, HES5, HEY2, CDKN1B, or NOTCH1, and the sense region can include a sequence complementary to the antisense region. The nucleic acid molecule can include two distinct strands having complementary sense and antisense regions. The nucleic acid molecule can include a single strand having complementary sense and antisense regions.

Nucleic acid molecules that interact with target RNA molecules and down-regulate gene encoding target RNA molecules (e.g., HES1, HES5, HEY2, CDKN1B, or NOTCH1 mRNA, SEQ ID NO:1, 2, 10, 7 or 11) may be expressed from transcription units inserted into DNA or RNA vectors. Recombinant vectors can be DNA plasmids or viral vectors. Nucleic acid molecule expressing viral vectors can be constructed based on, but not limited to, adeno-associated virus, retrovirus, adenovirus, or alphavirus. The recombinant vectors capable of expressing the nucleic acid molecules can be delivered as described herein, and persist in target cells. Alternatively, viral vectors can be used that provide for transient expression of nucleic acid molecules. Such vectors can be repeatedly administered as necessary. Once expressed, the nucleic acid molecules bind and down-regulate gene function or expression, e.g., via RNA interference (RNAi). Delivery of nucleic acid molecule expressing vectors can be systemic, such as by intravenous or intramuscular administration, by local administration, by administration to target cells ex-planted from a subject followed by reintroduction into the subject, or by any other means that would allow for introduction into the desired target cell.

Expression vectors may include a nucleic acid sequence encoding at least one nucleic acid molecule disclosed herein, in a manner which allows expression of the nucleic acid molecule. For example, the vector may contain sequence(s) encoding both strands of a nucleic acid molecule that include a duplex. The vector can also contain sequence(s) encoding a single nucleic acid molecule that is self-complementary and thus forms a nucleic acid molecule. Non-limiting examples of such expression vectors are described in Paul et al., 2002, Nature Biotechnology, 19, 505; Miyagishi and Taira, 2002, Nature Biotechnology, 19, 497; Lee et al., 2002, Nature Biotechnology, 19, 500; and Novina et al., 2002, Nature Medicine, advance online publication doi: 10.1038/nm725. Expression vectors may also be included in a mammalian (e.g., human) cell An expression vector may encode one or both strands of a nucleic acid duplex, or a single self-complementary strand that self hybridizes into a nucleic acid duplex. The nucleic acid sequences encoding nucleic acid molecules can be operably linked in a manner that allows expression of the nucleic acid molecule (see for example Paul et al., 2002, Nature Biotechnology, 19, 505; Miyagishi and Taira, 2002, Nature Biotechnology, 19, 497; Lee et al., 2002, Nature Biotechnology, 19, 500; and Novina et al., 2002, Nature Medicine, advance online publication doi:10.1038/nm725).

An expression vector may include one or more of the following: a) a transcription initiation region (e.g., eukaryotic pol I, II or III initiation region); b) a transcription termination region (e.g., eukaryotic pol I, II or III termination region); c) an intron and d) a nucleic acid sequence encoding at least one of the nucleic acid molecules, wherein said sequence is operably linked to the initiation region and the termination region in a manner that allows expression and/or delivery of the nucleic acid molecule. The vector can optionally include an open reading frame (ORF) for a protein operably linked on the 5'-side or the 3'-side of the sequence encoding the nucleic acid molecule; and/or an intron (intervening sequences).

Transcription of the nucleic acid molecule sequences can be driven from a promoter for eukaryotic RNA polymerase I (pol I), RNA polymerase II (pol II), or RNA polymerase III (pol III). Transcripts from pol II or pol III promoters are expressed at high levels in all cells; the levels of a given pol II promoter in a given cell type depends on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990, Proc. Natl. Acad. Sci. USA, 87, 6743-7; Gao and Huang 1993, Nucleic Acids Res., 21, 2867-72; Lieber et al., 1993, Methods Enzymol., 217, 47-66; Zhou et al., 1990, Mol. Cell. Biol., 10, 4529-37). Several investigators have demonstrated that nucleic acid molecules expressed from such promoters can function in mammalian cells (e.g. Kashani-Sabet et al., 1992, Antisense Res. Dev., 2, 3-15; Ojwang et al., 1992, Proc. Natl. Acad. Sci. USA, 89, 10802-6; Chen et al., 1992, Nucleic Acids Res., 20, 4581-9; Yu et al., 1993, Proc. Natl. Acad. Sci. USA, 90, 6340-4; L'Huillier et al., 1992, EMBO J., 11, 4411-8; Lisziewicz et al., 1993, Proc. Natl. Acad. Sci. U.S.A, 90, 8000-4; Thompson et al., 1995, Nucleic Acids Res., 23, 2259; Sullenger & Cech, 1993, Science, 262, 1566). More specifically, transcription units such as the ones derived from genes encoding U6 small nuclear (snRNA), transfer RNA (tRNA) and adenovirus VA RNA are useful in generating high concentrations of desired RNA molecules such as siNA in cells (Thompson et al., supra; Couture and Stinchcomb, 1996, supra; Noonberg et al., 1994, Nucleic Acid Res., 22, 2830; Noonberg et al., U.S. Pat. No. 5,624,803; Good et al., 1997, Gene Ther., 4, 45; Beigelman et al., International PCT Publication No. WO 96/18736). The above nucleic acid transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors) (see Couture and Stinchcomb, 1996 supra).

Nucleic acid molecule may be expressed within cells from eukaryotic promoters (e.g., Izant and Weintraub, 1985, Science, 229, 345; McGarry and Lindquist, 1986, Proc. Natl. Acad. Sci., USA 83, 399; Scanlon et al., 1991, Proc. Natl. Acad. Sci. USA, 88, 10591-5; Kashani-Sabet et al., 1992, Antisense Res. Dev., 2, 3-15; Dropulic et al., 1992, J. Virol., 66, 1432-41; Weerasinghe et al., 1991, J. Virol., 65, 5531-4; Ojwang et al., 1992, Proc. Natl. Acad. Sci. USA, 89, 10802-6; Chen et al., 1992, Nucleic Acids Res., 20, 4581-9; Sarver et al., 1990 Science, 247, 1222-1225; Thompson et al., 1995, Nucleic Acids Res., 23, 2259; Good et al., 1997, Gene Therapy, 4, 45. Those skilled in the art realize that any nucleic acid can be expressed in eukaryotic cells from the appropriate DNA/RNA vector. The activity of such nucleic acids can be augmented by their release from the primary transcript by a enzymatic nucleic acid (Draper et al., PCT WO 93/23569, and Sullivan et al., PCT WO 94/02595; Ohkawa et al., 1992, Nucleic Acids Symp. Ser., 27, 15-6; Taira et al., 1991, Nucleic Acids Res., 19, 5125-30; Ventura et al., 1993, Nucleic Acids Res., 21, 3249-55; Chowrira et al., 1994, J. Biol. Chem., 269, 25856.

A viral construct packaged into a viral particle would accomplish both efficient introduction of an expression construct into the cell and transcription of dsRNA construct encoded by the expression construct.

Methods for oral introduction include direct mixing of RNA with food of the organism, as well as engineered approaches in which a species that is used as food is engineered to express an RNA, then fed to the organism to be affected. Physical methods may be employed to introduce a nucleic acid molecule solution into the cell. Physical methods of introducing nucleic acids include injection of a solution containing the nucleic acid molecule, bombardment by particles covered by the nucleic acid molecule, soaking the cell or organism in a solution of the RNA, or electroporation of cell membranes in the presence of the nucleic acid molecule. In one embodiment provided herein is a cell comprising a nucleic acid molecule disclosed herein.

Other methods known in the art for introducing nucleic acids to cells may be used, such as chemical mediated transport, such as calcium phosphate, and the like. Thus the nucleic acid molecules may be introduced along with components that perform one or more of the following activities: enhance RNA uptake by the cell, promote annealing of the duplex strands, stabilize the annealed strands, or other-wise increase inhibition/down-regulation of the target gene.

Polymeric nanocapsules or microcapsules facilitate transport and release of the encapsulated or bound dsRNA into the cell. They include polymeric and monomeric materials, especially including polybutylcyanoacrylate. A summary of materials and fabrication methods has been published (see Kreuter, 1991). The polymeric materials which are formed from monomeric and/or oligomeric precursors in the polymerization/nanoparticle generation step, are per se known from the prior art, as are the molecular weights and molecular weight distribution of the polymeric material which a person skilled in the field of manufacturing nanoparticles may suitably select in accordance with the usual skill Nucleic acid molecules may be formulated as a microemulsion. A microemulsion is a system of water, oil and amphiphile which is a single optically isotropic and thermodynamically stable liquid solution. Typically microemulsions are prepared by first dispersing an oil in an aqueous surfactant solution and then adding a sufficient amount of a 4th component, generally an intermediate chain-length alcohol to form a transparent system.

Surfactants that may be used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DA0750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules.

Delivery formulations can include water soluble degradable crosslinked polymers that include one or more degradable crosslinking lipid moiety, one or more PEI moiety, and/or one or more mPEG (methyl ether derivative of PEG (methoxypoly (ethylene glycol)).

Dosages

The useful dosage to be administered and the particular mode of administration will vary depending upon such factors as the cell type, or for in vivo use, the age, weight and the particular subject and region thereof to be treated, the particular nucleic acid and delivery method used, the therapeutic or diagnostic use contemplated, and the form of the formulation, for example, suspension, emulsion, micelle or liposome, as will be readily apparent to those skilled in the art. Typically, dosage is administered at lower levels and increased until the desired effect is achieved.

The "therapeutically effective dose" for purposes herein is thus determined by such considerations as are known in the art. The dose must be effective to achieve improvement including but not limited to improved survival rate or more rapid recovery, or improvement or elimination of symptoms and other indicators as are selected as appropriate measures by those skilled in the art.

Suitable amounts of inhibitors, e.g. nucleic acid molecules, may be introduced and these amounts can be empirically determined using standard methods. Effective concentrations of individual nucleic acid molecule species in the environment of a cell may be about 1 femtomolar, about 50 femtomolar, 100 femtomolar, 1 picomolar, 1.5 picomolar, 2.5 picomolar, 5 picomolar, 10 picomolar, 25 picomolar, 50 picomolar, 100 picomolar, 500 picomolar, 1 nanomolar, 2.5 nanomolar, 5 nanomolar, 10 nanomolar, 25 nanomolar, 50 nanomolar, 100 nanomolar, 500 nanomolar, 1 micromolar, 2.5 micromolar, 5 micromolar, 10 micromolar, 100 micromolar or more.

In general, the active dose of nucleic acid compound for humans is in the range of from 1 ng/kg to about 20-100 milligrams per kilogram (mg/kg) body weight of the recipient per day, preferably about 0.01 mg to about 2-10 mg/kg body weight of the recipient per day, in a regimen of a single dose, a one dose per day or twice or three or more times per day for a period of 1-4 weeks or longer. A suitable dosage unit of nucleic acid molecules may be in the range of 0.001 to 0.25 milligrams per kilogram body weight of the recipient per day, or in the range of 0.01 to 20 micrograms per kilogram body weight per day, or in the range of 0.01 to 10 micrograms per kilogram body weight per day, or in the range of 0.10 to 5 micrograms per kilogram body weight per day, or in the range of 0.1 to 2.5 micrograms per kilogram body weight per day. Dosage may be from 0.01 ug to 1 g per kg of body weight (e.g., 0.1 ug, 0.25 ug, 0.5 ug, 0.75 ug, 1 ug, 2.5 ug, 5 ug, 10 ug, 25 ug, 50 ug, 100 ug, 250 ug, 500 ug, 1 mg, 2.5 mg, 5 mg, 10 mg, 25 mg, 50 mg, 100 mg, 250 mg, or 500 mg per kg of body weight).

Dosage levels of the order of from about 0.1 mg to about 140 mg per kilogram of body weight per day are useful in the treatment of the above-indicated conditions (about 0.5 mg to about 7 g per subject per day). The amount of active ingredient that can be combined with the carrier materials to produce a single dosage form varies depends upon the host treated and the particular mode of administration. Dosage unit forms generally contain between from about 1 mg to about 500 mg of an active ingredient.

It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

Pharmaceutical compositions that include the inhibitors, e.g. nucleic acid molecules, disclosed herein may be administered once, once daily (QD), twice a day (bid), three times a day (tid), four times a day (qid), at any interval and for any duration, or by continuous application for any duration, as is medically appropriate. The therapeutic agent may also be dosed in dosage units containing two, three, four, five, six or more sub-doses administered at appropriate intervals throughout the day. In that case, the nucleic acid molecules contained in each sub-dose may be correspondingly smaller in order to achieve the total daily dosage unit. The dosage unit can also be compounded for a single dose over several days, e.g., using a conventional sustained release formulation which provides sustained and consistent release of the dsRNA over a several day period. Sustained release formulations are well known in the art. The dosage unit may contain a corresponding multiple of the daily dose. The composition can be compounded in such a way that the sum of the multiple units of a nucleic acid together contain a sufficient dose. The combination of therapeutic agents may be adminstered prior to, during or after exposure to the insult (i.e. ototoxin, mechanical injury etc.)

Pharmaceutical Compositions, Kits, and Containers

Also provided are compositions, combinations, commercial packages, kits, containers and formulations that include an inhibitor, for example a nucleic acid molecule (e.g., an siNA molecule), as provided herein for down-regulating expression of HES1, HES5, HEY2, CDKN1B or NOTCH1 for administering or distributing the nucleic acid molecule to a patient. A kit may include at least one container and at least one label. Suitable containers include, for example, bottles, vials, syringes, and test tubes. The containers can be formed from a variety of materials such as glass, metal or plastic. The container can hold amino acid sequence(s), small molecule(s), nucleic acid sequence(s), cell population(s) and/or antibody(s) and/or any other component required for relevant laboratory, prognostic, diagnostic, prophylactic and therapeutic purposes. Indications and/or directions for such uses can be included on or with such container, as can reagents and other compositions or tools used for these purposes.

The container can alternatively hold a composition that is effective for treating, diagnosis, prognosing or prophylaxing a condition and can have a sterile access port (for example the container can be an intravenous solution bag or a vial having a stopper pierceable by a hypodermic injection needle). The active agents in the composition can be a nucleic acid molecule capable of specifically binding HES1, HES5, HEY2, CDKN1B or NOTCH1 mRNA and/or down-regulating the function of HES1, HES5, HEY2, CDKN1B or NOTCH1.

A kit may further include a second container that includes a pharmaceutically-acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

Federal law requires that the use of pharmaceutical compositions in the therapy of humans be approved by an agency of the Federal government. In the United States, enforcement is the responsibility of the Food and Drug Administration, which issues appropriate regulations for securing such approval, detailed in 21 U.S.C. §301-392. Similar approval is required by most foreign countries. Regulations vary from country to country, but individual procedures are well known to those in the art and the compositions, combinations and methods provided herein preferably comply accordingly.

The combinations disclosed herein can be used to treat diseases, conditions or disorders associated with expression of HES1, HES5, and HEY2, or CDKN1B, NOTCH1 and HEY2 such as disease, injury, condition or pathology in the ear, vestibular sensory system, and any other disease or conditions that are related to or will respond to the levels of expression of HES1, HES5 and HEY2, or CDKN1B, NOTCH1 and HEY2 in a cell or tissue, alone or in combination with other therapies. As such, compositions, combinations, commercial packages, kits and methods disclosed herein may include packaging a nucleic acid molecule disclosed herein that includes a label or package insert. The label may include indications for use of the nucleic acid molecules such as use for treatment or prevention of diseases, disorders, injuries and conditions of the ear or vestibular system, including, without being limited to, Meniere's disease, acoustic trauma, deafness, hearing loss, presbycusis and any other disease or condition disclosed herein. The label may include indications for use of the nucleic acid molecules such as use for treatment or prevention of attenuation of neuronal degeneration. Neuronal degeneration includes for example degeneration of the auditory nerve, (also known as the vestibulocochlear nerve or acoustic nerve and responsible for transmitting sound and equilibrium information from the inner ear to the brain); the hair cells of the inner ear that transmit information to the brain via the auditory nerve, which consists of the cochlear nerve, and the vestibular nerve, and emerges from the medulla oblongata and enters the inner skull via the internal acoustic meatus (or internal auditory meatus) in the temporal bone, along with the facial nerve. The label may include indications for use of the nucleic acid molecules such as use for treatment or prevention of any other disease or conditions that are related to or will respond to the levels of expression of HES1, HES5 and HEY2, or expression of CDKN1B, NOTCH1 and HEY2, in a cell or tissue, alone or in combination with other therapies. A label may include an indication for use in reducing and/or down-regulating expression of expression of HES1, HES5 and HEY2, or CDKN1B, NOTCH1 and HEY2. A "package insert" is used to refer to instructions customarily included in commercial packages of therapeutic products, that contain information about the indications, usage, dosage, administration, contraindications, other therapeutic products to be combined with the packaged product, and/or warnings concerning the use of such therapeutic products, etc.

Those skilled in the art will recognize that other treatments, drugs and therapies known in the art can be readily combined with the nucleic acid molecules herein (e.g. dsNA molecules) and are hence contemplated herein.

Methods of Treatment

In another aspect, the present invention relates to a method for the treatment of a subject in need of treatment for a disease or disorder associated with the abnormal expression of HES1, HES5, HEY2, CDKN1B or NOTCH1, comprising administering to the subject an amount of inhibitors which reduce or inhibit expression of HES1, HES5 and HEY2 genes, or of inhibitor that reduce or inhibit expression of CDKN1B, NOTCH1 and HEY2 genes.

In one embodiment, nucleic acid molecules may be used to down-regulate or inhibit the expression of HES1, HES5, HEY2, CDKN1B, or NOTCH1 and/or HES1, HES5, HEY2, CDKN1B, or NOTCH1 proteins arising from HES1, HES5, HEY2, CDKN1B, or NOTCH1 and/or haplotype polymorphisms that are associated with a disease or condition, (e.g., neurodegeneration). Analysis of HES1, HES5, HEY2, CDKN1B, or genes, and/or protein or RNA levels can be used to identify subjects with such polymorphisms or those subjects who are at risk of developing traits, conditions, or diseases described herein. These subjects are amenable to treatment, for example, treatment with nucleic acid molecules disclosed herein and any other composition useful in treating diseases related to HES1, HES5, HEY2, CDKN1B, or NOTCH1 gene expression. As such, analysis of HES1, HES5, HEY2, CDKN1B, or NOTCH1 gene and/or protein or RNA levels can be used to determine treatment type and the course of therapy in treating a subject. Monitoring of protein or RNA levels can be used to predict treatment outcome and to determine the efficacy of combinations and compositions that modulate the level and/or activity of certain genes and/or proteins associated with a trait, a condition, or a disease.

Provided herein are methods of inhibiting the expression target genes selected from the group consisting of a gene transcribed into mRNA set forth in any one of SEQ ID NOS:1, 2, 10, 7 or 11 by at least 40%, preferably by 50%, 60% or 70%, more preferably by 75%, 80% or 90% as compared to a control, comprising contacting an mRNA transcript of the target gene disclosed herein with a combination or a compositions provided herein.

In one embodiment the oligoribonucleotide inhibits one or more of the target genes disclosed herein, whereby the inhibition is selected from the group comprising inhibition of gene function, inhibition of polypeptide and inhibition of mRNA expression.

In one embodiment the compound inhibits the target polypeptide, whereby the inhibition is selected from the group comprising inhibition of function (which is examined by, for example, an enzymatic assay or a binding assay with a known interactor of the native gene/polypeptide, inter alia), inhibition of protein (which is examined by, for example, Western blotting, ELISA or immuno-precipitation, inter alia) and inhibition of mRNA expression (which is examined by, for example, Northern blotting, quantitative RT-PCR, in-situ hybridization or microarray hybridization, inter alia).

In one embodiment the compound is down-regulating a mammalian polypeptide, whereby the down-regulation is selected from the group comprising down-regulation of function (which is examined by, for example, an enzymatic assay or a binding assay with a known interactor of the native gene/polypeptide, inter alia), down-regulation of protein (which is examined by, for example, Western blotting, ELISA or immuno-precipitation, inter alia) and down-regulation of mRNA expression (which is examined by, for example, Northern blotting, quantitative RT-PCR, in-situ hybridization or microarray hybridization, inter alia).

In additional embodiments provided herein is a method of treating a patient suffering from a disease accompanied by an elevated level of a mammalian gene elected from the group consisting of a gene transcribed into mRNA set forth in any one of SEQ ID NOS:1, 2, 10, 7 or 11, the method comprising administering to the patient a combination or composition as disclosed herein in a therapeutically effective dose thereby treating the patient.

Methods, combinations and compositions which inhibit a mammalian gene or polypeptide as disclosed herein are discussed herein at length, and any of said molecules and/or compositions are beneficially employed in the treatment of a patient suffering from any of said conditions. Novel methods of treatment using known compounds and compositions fall within the scope of the present invention.

In various embodiments, the methods disclosed herein include administering a therapeutically effective amount of compounds which down-regulate expression of a hearing loss associated gene. By "exposure to a toxic agent" is meant that the toxic agent is made available to, or comes into contact with, a mammal. A toxic agent can be toxic to the nervous system. Exposure to a toxic agent can occur by direct administration, e.g., by ingestion or administration of a food, medicinal, or therapeutic agent, e.g., a chemotherapeutic agent, by accidental contamination, or by environmental exposure, e.g., aerial or aqueous exposure.

Further provided is a method of preventing degeneration of the auditory nerve, also known as the vestibulocochlear nerve or acoustic nerve, responsible for transmitting sound and equilibrium information from the inner ear to the brain. The hair cells of the inner ear transmit information to the brain via the auditory nerve, which consists of the cochlear nerve, and the vestibular nerve, and emerges from the medulla oblongata and enters the inner skull via the internal acoustic meatus (or internal auditory meatus) in the temporal bone, along with the facial nerve.

Further provided is a process of preparing a pharmaceutical composition, which comprises:
providing one or more double stranded molecule disclosed herein; and
admixing said molecule with a pharmaceutically acceptable carrier.

In a preferred embodiment, the molecule used in the preparation of a pharmaceutical composition is admixed with a carrier in a pharmaceutically effective dose. In a particular embodiment the compound of the present invention is conjugated to a steroid or to a lipid or to another suitable molecule e.g. to cholesterol.

The nucleic acid molecules disclosed herein are able to down-regulate the expression of HES1, HES5, HEY2, CDKN1B, or NOTCH1 in a sequence specific manner. The nucleic acid molecules may include a sense strand and an antisense strand which include contiguous nucleotides that are at least partially complementary (antisense) to a portion of HES1, HES5, HEY2, CDKN1B, or NOTCH1 mRNA.

In some embodiments, dsRNA specific for HES1, HES5, HEY2, CDKN1B or NOTCH1 can be used in conjunction with other therapeutic agents and/or dsRNA specific for other molecular targets, such as, without being limited to various proapoptotic genes.

A method for treating or preventing HES1, HES5, HEY2, CDKN1B or NOTCH1 associated disease or condition in a subject or organism may include contacting the subject or organism with a combination or a composition as provided herein under conditions suitable to down-regulate the expression of the gene in the subject or organism.

A method for treating or preventing an ear disorder in a subject or organism may include contacting the subject or organism with a combination or a composition as provided herein under conditions suitable to down-regulate the expression of the HES1, HES5, HEY2, CDKN1B or NOTCH1 gene in the subject or organism.

In preferred embodiments the subject being treated is a warm-blooded animal and, in particular, mammals including human.

The methods disclosed herein comprise administering to the subject a combination or a composition of inhibitory compounds which down-regulate expression of HES1, HES5 and HEY2 or CDKN1B, NOTCH1 and HEY2, in a therapeutically effective dose so as to thereby treat the subject.

Methods, combinations and compositions which down-regulate HES1, HES5, HEY2, CDKN1B or NOTCH1, in particular combination of a HES1 inhibitor or a pharmaceutically acceptable salt or prodrug thereof, a HES5 inhibitor or a pharmaceutically acceptable salt or prodrug thereof and a HEY2 inhibitor or a pharmaceutically acceptable salt or prodrug thereof, or combination of a CDKN1B inhibitor or a pharmaceutically acceptable salt or prodrug thereof, a NOTCH1 inhibitor or a pharmaceutically acceptable salt or prodrug thereof and a HEY2 inhibitor or a pharmaceutically acceptable salt or prodrug thereof, are discussed herein at length, and any of said combinations and/or compositions may be beneficially employed in the treatment of a subject suffering from any of said conditions. Sense strand and antisense strand oligonucleotide sequences useful in generating dsRNA are set forth herein. Preferred oligonucleotide sequences useful in the preparation of dsRNA that down-regulate expression of HES1 are set forth in SEQ ID NOS:26667-26690 and 26691-26706; of HES5 are set forth in SEQ ID NOS:26707-26724 and 26725-26732; of HEY2 are set forth in SEQ ID NOS:26779-26784 and 26785-26788; of CDKN1B are set forth in SEQ ID NOS:26867-26886 and 26887-26900 or NOTCH1 are set forth in SEQ ID NOS:26901-26910 and 26911-26912.

The methods disclosed herein comprise administering to the subject a composition or a combination as disclosed herein, of inhibitory compounds which down-regulate expression of the genes set forth in SEQ ID NOS: 1, 2, 10, 7 or 11; and in particular compositions or combinations of oligonucleotide compounds in a therapeutically effective dose so as to thereby treat the subject.

"Treatment" refers to both therapeutic treatment and prophylactic or preventative measures, wherein the object is to prevent a disorder or reduce the symptoms of a disorder, such as hearing disorder or impairment (or balance impairment), to prevent or reduce cell death associated with a hearing loss-associated disease as listed herein, to promote regeneration of otic (sensory) cells or to promote differentiation of supporting cells in the inner ear into otic (sensory) cells. Those in need of treatment include those already experiencing the disease or condition, those prone to having the disease or condition, and those in which the disease or condition is to be prevented. The compositions or combinations disclosed herein are administered before, during or subsequent to the onset of the disease or condition.

Without being bound by theory, the hearing impairment may be due to apoptotic inner ear hair cell damage or loss, wherein the damage or loss is caused by infection, mechanical injury, loud sound, aging, or, in particular, chemical-induced ototoxicity. Ototoxins include therapeutic drugs including antineoplastic agents, salicylates, quinines, and aminoglycoside antibiotics, contaminants in foods or medicinals, and environmental or industrial pollutants. Typically, treatment is performed to prevent or reduce ototoxicity, especially resulting from or expected to result from administration of therapeutic drugs. Preferably a therapeutically effective composition is given immediately after the exposure to prevent or reduce the ototoxic effect. More preferably, treatment is provided prophylactically, either by administration of the composition prior to or concomitantly with the ototoxic pharmaceutical or the exposure to the ototoxin.

Hearing impairments relevant to the present disclosure may be due to end-organ lesions involving inner ear hair cells, e.g., acoustic trauma, viral endolymphatic labyrinthitis, Meniere's disease. Hearing impairments include tinnitus, which is a perception of sound in the absence of an acoustic stimulus, and may be intermittent or continuous, wherein there is diagnosed a sensorineural loss. Hearing loss may be due to bacterial or viral infection, such as in herpes zoster oticus, purulent labyrinthitis arising from acute otitis media, purulent meningitis, Chronic otitis media, sudden deafness including that of viral origin, e.g., viral endolymphatic labyrinthitis caused by viruses including mumps, measles, influenza, chicken pox, mononucleosis and adenoviruses. The hearing loss can be congenital, such as that caused by rubella, anoxia during birth, bleeding into the inner ear due to trauma during delivery, ototoxic drugs administered to the mother, erythroblastosis fetalis, and hereditary conditions including Waardenburg's syndrome and Hurler's syndrome.

The hearing loss can be noise-induced, generally due to a noise greater than 85 decibels (db) that damages the inner ear. In a particular aspect, the hearing loss is caused by an ototoxic drug that effects the auditory portion of the inner ear, particularly inner ear hair cells. Incorporated herein by reference are chapters 196, 197, 198 and 199 of The Merck Manual of Diagnosis and Therapy, 14th Edition, (1982), Merck Sharp & Dome Research Laboratories, N.J. and corresponding chapters in the most recent 16th edition, including Chapters 207 and 210) relating to description and diagnosis of hearing and balance impairments.

In one embodiment, provided is a method for treating a mammal having or prone to a hearing (or balance) impairment or treating a mammal prophylactically in conditions where inhibition of the genes of the invention is beneficial. The method would prevent or reduce the occurrence or severity of a hearing (or balance) impairment that would result from inner ear cell injury, loss, or degeneration, in particular caused by an ototoxic agent. In some embodiments the method includes administering a therapeutically effective amount of a HES1 inhibitor, a HES5 inhibitor and a HEY2 inhibitor. In other embodiments the method includes administering a therapeutically effective amount of a CDKN1B inhibitor, a NOTCH1 inhibitor and a HEY2 inhibitor.

It is the object of the present disclosure to provide methods, combinations and compositions for treating a mammal, to prevent, reduce, or treat a hearing impairment, disorder or imbalance, optionally an ototoxin-induced hearing condition, by administering to a mammal in need of such treatment a composition or a combination as disclosed herein. In some embodiments the methods are for treating a hearing disorder or impairment wherein the ototoxicity results from administration of a therapeutically effective amount of an ototoxic pharmaceutical drug. Typical ototoxic drugs are chemotherapeutic agents, e.g. antineoplastic agents, and antibiotics. Other possible candidates include loop-diuretics, quinines or a quinine-like compound, and salicylate or salicylate-like compounds.

In some embodiments, the combinations and compositions provided herein are co-administered with an ototoxin. For example, an improved method is provided for treatment of infection of a mammal by administration of an aminoglycoside antibiotic, the improvement comprising administering a therapeutically effective amount of a composition or a combination of inhibitors (particularly dsRNAs) which down-regulate expression of HES1, HES5 and HEY2, or which down-regulate expression of CDKN1B, NOTCH1 and HEY2 to the patient in need of such treatment to reduce or prevent ototoxin-induced hearing impairment associated with the antibiotic. The compounds which down-regulate expression of HES1, HES5, HEY2, CDKN1B or NOTCH1, e.g. dsRNAs are preferably administered locally within the inner ear.

In yet another embodiment an improved method for treatment of cancer in a mammal by administration of a chemotherapeutic compound is provided, wherein the improvement comprises administering a therapeutically effective amount of a composition or combination as disclosed herein to the patient in need of such treatment to reduce or prevent ototoxin-induced hearing impairment associated with the chemotherapeutic drug. The compositions or combinations which reduce or prevent the ototoxin-induced hearing impairment, e.g. compositions and combinations comprising dsRNA molecules as disclosed herein, inter alia are preferably administered directly to the cochlea as naked dsRNAs in a vehicle such as PBS or other physiological solutions, but may alternatively be administered with a delivery vehicle as described above.

In another embodiment the methods of treatment are applied to treatment of hearing impairment resulting from the administration of a chemotherapeutic agent in order to treat its ototoxic side-effect.

In another embodiment the methods, compositions and combinations are applied to hearing impairments resulting from the administration of quinine and its synthetic substitutes, typically used in the treatment of malaria, to treat its ototoxic side-effect.

In some embodiments of combinations provided herein, combination therapy is achieved by administering two or three inhibitors (i.e. dsRNAs) each of which is formulated and administered separately, or by administering the inhibitors in a single formulation. Other combinations are also encompassed by combination therapy. For example, two inhibitors can be formulated together and administered in conjunction with a separate formulation containing a third inhibitor. While the two or more inhibitors in the combination therapy can be administered simultaneously, they need not be. For example, administration of a first inhibitor (or combination of inhibitors) can precede administration of a second inhibitor (or combination of inhibitors) by minutes, hours, days, or weeks. Thus, the two or more inhibitors can be administered within minutes of each other or within one or several hours of each other or within one or several days of each other or within several weeks of each other. In some cases even longer intervals are possible. The two or more inhibitors used in combination therapy may or may not be present within the patient's body at the same time. Combination therapy includes two or more administrations of one or more of the inhibitors used in the combination. For example, if dsRNA1 and dsRNA2 (i.e. wherein dsRNA1 targets gene 1 and dsRNA2 targets gene 2) are used in a combination, one could administer them sequentially in any combination one or more times, e.g., in the order dsRNA1-dsRNA2, dsRNA2-dsRNA1, dsRNA1-dsRNA2-dsRNA1, dsRNA2-dsRNA1-dsRNA2, dsRNA1-dsRNA1-dsRNA2, dsRNA1-dsRNA2-dsRNA2 etc.

The combinations as disclosed herein can be administered in a form of a single pharmaceutical formulation, optionally together with a pharmaceutically acceptable diluent or carrier. The individual components of such a combination referred to as inhibitors, can be administered either simultaneously, concurrently, separately or sequentially, from the same or separate pharmaceutical formulations.

In some embodiments, each inhibitor is administered by the same route, either from the same or from different pharmaceutical compositions. In other embodiments, using the same route of administration for the first inhibitor, the second inhibitor and the third inhibitor either is impossible or is not preferred. Persons skilled in the art are aware of the best modes of administration for each inhibitor, either alone or in a combination.

As used herein, the term "substantially simultaneously" with regard to administration of at least two inhibitors means that a second inhibitor is administered within a time period of no greater than about 5 minutes after administration of the first inhibitor, preferably within a time period of about 1 minute, more preferably within a time period of about 30 seconds, and most preferably, is administered simultaneously with the first inhibitor from the same or separate pharmaceutical formulations. Similarly, with regard to administration of three inhibitors, a third inhibitor may be administered within a time period of no greater than about 5 minutes after administration of the second inhibitor, preferably within a time period of about 1 minute, more preferably within a time period of about 30 seconds, and most preferably is administered simultaneously with the second inhibitor from the same or separate pharmaceutical formulations.

Hearing Regeneration

Sensory progenitor cells can develop as either hair cells or supporting cells. Ablation studies indicate that removal of a hair cell changes the fate of a surrounding cell from a supporting to a hair cell. This response suggests that hair cells generate inhibitory signals that prevent neighboring cells from developing as hair cells. This type of interaction is consistent with the effects of Notch-mediated lateral inhibition. Consistent with this hypothesis, two Notch ligands, Jag2 and delta 1 (Dll1) are rapidly upregulated in a subset of Atoh1-positive cells. The expression of these ligands leads to activation of Notch 1 and the increased transcription of two Notch pathway target genes, HES1 and HES5 in cells that will develop as supporting cells. Deletion of any of the genes in this pathway leads to an overproduction of hair cells, suggesting that Notch signalling has a role in diverting progenitor cells from the hair cell fate. The mechanism of this diversion has been examined using cells in Kolliker's organ. First, co-transfection of Kolliker's organ cells with Atoh1 and HES1 was sufficient to inhibit hair cell formation, suggesting that Atoh1 transcription is a target of HES1 in the ear. Second, transient activation of ATOH1 in patches of Kolliker's organ cells leads to activation of the Notch signalling pathway within those cells and to the inhibition of ATOH1 and hair cell fate in a subset of those cells.

Zine et al. (J Neurosci. 2001 21(13):4712-20) demonstrate that HES1 and HES5 activities are important for repressing the commitment of progenitor cells to IHCs and OHCs fates, respectively, likely by antagonizing Math1. This negative regulation is critical for the correct number of hair cells to be produced and for the establishment of the normal cochlear mosaic of a single row of IHCs and three rows of OHCs. In the vestibular system, HES1 and HES5 also act as negative regulators of hair cell differentiation within the utricle and saccule epithelia. It is possible that simultaneous down-regulation of both of HES1 and HES5 in the cochlea might be used to stimulate the replacement of lost auditory hair cells. Such studies may have a significant therapeutic value, because loss of auditory hair cells through disease, trauma, and aging is a common cause of hearing loss and/or deafness.

Details of certain indications in which the compounds disclosed herein are useful as therapeutics are described herein.

The aspects and embodiments provided herein have been described in an illustrative manner, and it is to be understood that the terminology used is intended to be in the nature of words of description rather than of limitation.

Many modifications and variations are possible in light of the above teachings. It is, therefore, to be understood that within the scope of the appended claims, the invention can be practiced otherwise than as specifically described.

Throughout this application, various publications, including United States Patents, are referenced by author and year and patents by number. The disclosures of these publications and patents and patent applications in their entireties are hereby incorporated by reference into this application in order to more fully describe the state of the art to which this invention pertains.

The present disclosure is illustrated in detail below with reference to examples, but is not to be construed as being limited thereto.

Citation of any document herein is not intended as an admission that such document is pertinent prior art, or considered material to the patentability of any claim of the present disclosure. Any statement as to content or a date of any document is based on the information available to applicant at the time of filing and does not constitute an admission as to the correctness of such a statement.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook et al., *Molecular cloning: A laboratory manual*, Cold Springs Harbor Laboratory, New-York (1989, 1992), and in Ausubel et al., *Current Protocols in Molecular Biology*, John Wiley and Sons, Baltimore, Md. (1988), and as in Ausubel et al., Current Protocols in Molecular Biology, John Wiley and Sons, Baltimore, Md. (1989) and as in Perbal, A Practical Guide to Molecular Cloning, John Wiley & Sons, New York (1988), and as in Watson et al., Recombinant DNA, Scientific American Books, New York and in Birren et al (eds) Genome Analysis: A Laboratory Manual Series, Vols. 1-4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out as in standard PCR Protocols: A Guide To Methods And Applications, Academic Press, San Diego, Calif. (1990). In situ PCR in combination with Flow Cytometry (FACS) can be used for detection of cells containing specific DNA and mRNA sequences (Testoni et al., Blood 1996, 87:3822.) Methods of performing RT-PCR are well known in the art.

Example 1

In Vitro Testing of dsRNA Molecules

About $1.5-2\times10^5$ tested cells (HeLa cells and/or 293T cells for siRNA targeting human genes and NRK52 (normal rat kidney proximal tubule cells) cells and/or NMuMG cells (mouse mammary epithelial cell line) for siRNA targeting the rat/mouse gene) were seeded per well in 6 wells plate (70-80% confluent).

24 hours later, cells were transfected with dsRNA molecules using the Lipofectamine™ 2000 reagent (Invitrogen) at final concentrations of 5 nM or 20 nM. The cells were incubated at 37° C. in a $CO_2$ incubator for 72 h.

As positive control for transfection, PTEN-Cy3 labeled dsRNA molecules were used. GFP dsRNA molecules were used as negative control for siRNA activity. At 72 h after transfection, cells were harvested and RNA was extracted from cells. Transfection efficiency was tested by fluorescent microscopy. The percent of inhibition of gene expression using specific preferred siRNA structures was determined using qPCR analysis of a target gene in cells expressing the endogenous gene.

Body Fluid/Cell Stability Assay

The modified compounds disclosed herein are tested for duplex stability in human, rat or mouse plasma or human, rat or mouse serum (to test in model system), or CSF (cerebrospinal fluid; human, mouse or rat) or human cell extract, as follows:

For example: dsRNA molecules at final concentration of 7 uM are incubated at 37° C. in 100% human serum (Sigma Cat #H4522). (siRNA stock 100 uM diluted in human serum 1:14.29 or human tissue extract from various tissue types.). Five ul (5 ul) are added to 15 ul 1.5×TBE-loading buffer at different time points (for example 0, 30 min, 1 h, 3 h, 6 h, 8 h, 10 h, 16 h and 24 h). Samples are immediately frozen in liquid nitrogen and are kept at −20° C.

Each sample is loaded onto a non-denaturing 20% acrylamide gel, prepared according to methods known in the art. The oligos are visualized with ethidium bromide under UV light.

Exonuclease Stability Assay

To study the stabilization effect of 3' non-nucleotide moieties on a nucleic acid molecule the sense strand, the antisense strand and the annealed dsRNA duplex are incubated in cytosolic extracts prepared from different cell types.

Extract: HCT116 cytosolic extract (12 mg/ml).

Extract buffer: 25 mM Hepes pH-7.3 at 37° C.; 8 mM $MgCl_2$; 150 mM NaCl with 1 mM DTT was added fresh immediately before use.

Method: 3.5 ml of test dsRNA (100 mM), were mixed with 46.5 ml contain 120 mg of HCT116 cytosolic extract. The 46.5 ml consists of 12 ml of HCT116 extract, and 34.5 ml of the extract buffer supplemented with DTT and protease inhibitors cocktail/100 (Calbiochem, setIII-539134). The final concentration of the siRNA in the incubation tube is 7 mM. The sample is incubated at 37° C., and at the indicated time point 5 ml are moved to fresh tube, mixed with 15 ml of 1×TBE-50% Glycerol loading buffer, and snap frozen in Liquid $N_2$. The final concentration of the siRNA in the loading buffer is 1.75 mM (21 ng siRNA/ml). For analyses by native PAGE and EtBr staining 50 ng are loaded per lane. For Northern analyses ing of tested siRNA are loaded per lane.

Innate Immune Response to dsRNA Molecules:

Fresh human blood (at RT) is mixed at 1:1 ratio with sterile 0.9% NaCl at RT, and gently loaded (1:2 ratio) on Ficoll (Lymphoprep, Axis-Shield cat #1114547). Samples are centrifuged at RT (22° C., 800 g) in a swinging centrifuge for 30 minutes, washed with RPMI1640 medium and centrifuged (RT, 250 g) for 10 minutes. Cells are counted and seeded at final concentration of $1.5 \times 10^6$ cell/ml in growth medium (RPMI1640+10% FBS+2 mM L-glutamine+1% Pen-Strep) and incubated for 1 hour at 37° C. before dsRNA treatment. Cells are exposed to the test dsRNAs at different concentrations using the Lipofectamine™ 2000 reagent (Invitrogen) according to manufacturer's instructions and incubated at 37° C. in a 5% $CO_2$ incubator for 24 hours.

As a positive control for IFN response, cells are treated with either poly(I:C), a synthetic analog of double strand RNA (dsRNA) which is a TLR3 ligand (InvivoGen Cat #tlrl-pic) at final concentrations of 0.25-5.0 μg/mL or to Thiazolaquinolone (CLO75), a TLR 7/8 ligand (InvivoGen Cat #tlrl-c75) at final concentrations of 0.075-2 μg/mL. Cell treated with Lipofectamine™ 2000 reagent are used as negative (reference) control for IFN response.

At about 24 hours following incubation, cells are collected and supernatant is transferred to new tubes. Samples are frozen immediately in liquid nitrogen and secretion of IL-6 and TNF-α cytokines was tested using IL-6, DuoSet ELISA kit (R&D System DY2060), and TNF-α, DuoSet ELISA kit (R&D System DY210), according to manufacturer's instructions. RNA is extracted from the cell pellets and mRNA levels of human genes IFIT1 (interferon-induced protein with tetratricopeptide repeats 1) and MX1 (myxovirus (influenza virus) resistance 1, interferon-inducible protein p78) were measured by qPCR. Measured mRNA quantities are normalized to the mRNA quantity of the reference gene peptidylprolyl isomerase A (cyclophilin A; CycloA). Induction of IFN-signaling is evaluated by comparing the quantity of mRNA from IFIT1 and MX1 genes from treated cells, relative to their quantities non-treated cells. The qPCR results are those that passed QC standards, i.e. the value of the standard curve slope was in the interval [−4, −3], $R^2>0.99$, no primer dimers. Results that do not pass the QC requirements are disqualified from analysis.

In general, the dsRNAs having specific sequences that were selected for in vitro testing were specific for human and a second species such as rat or rabbit genes. The dsRNA were tested for activity to Human (Hu), mouse (Ms), rat (Rt), chinchilla (Chn) and or guinea-pig (GP) target gene. For example, activity in chinchilla was tested by cloning the chinchilla target gene (i.e. CDKN1B) and expressing in a 293 or HeLa cell line. Similar results are obtained using siRNAs having these RNA sequences and modified as described herein.

PCT/US12/49616 discloses chemically modified dsRNA nucleic acid molecules, and is incorporated herein by reference in its entirety.

Example 2

Generation of Sequences for Active dsRNA Molecules to the Target Genes and Production of the siRNAs Using proprietary algorithms and the known sequence of the mRNA of the target genes disclosed herein, the sequences of many potential dsRNA, i.e. siRNAs were generated.

Specifically, SEQ ID NOS:23-381 provide human 19 mer oligonucleotides; SEQ ID NOS:382-693 provide best 19-mer human-cross species oligonucleotides; SEQ ID NOS:694-1367 provide human 18 mer oligonucleotides; and SEQ ID NO:16-1495 provide best 18-mer human-cross species oligonucleotides useful in generating dsRNA to down-regulate HES1 expression; Table I includes certain preferred 19 mer oligonucleotides based on Structure A1, set forth in SEQ ID NOS: 26,667-26,690 and based on Structure A2, set forth in SEQ ID NOS:26,691-26,706 useful in generating dsRNA to down-regulate HES1 expression.

SEQ ID NOS:1496-1759 provide human 19 mer oligonucleotides; SEQ ID NOS:1760-2029 provide best 19-mer human-cross species oligonucleotides; SEQ ID NOS:2030-2575 provide human 18 mer oligonucleotides; and SEQ ID NOS:2576-2703 provide best 18-mer human-cross species oligonucleotides useful in generating dsRNA to down-regulate HES5 expression; Table II includes certain preferred 19 mer oligonucleotides based on Structure A1, set forth in SEQ ID NOS: 26,707-26,724 and based on Structure A2, set forth in SEQ ID NOS:26,725-26,732 useful in generating dsRNA to down-regulate HES5 expression.

SEQ ID NOS:13004-14077 provide human 19 mer oligonucleotides; SEQ ID NOS:14078-14801 provide best 19-mer human-cross species oligonucleotides; SEQ ID NOS:14802-16389 provide best human 18 mer oligonucleotides; and SEQ ID NOS:16390-16621 provide best 18-mer human-cross species oligonucleotides useful in generating dsRNA to down-regulate HEY2 expression; Table III includes certain preferred 19 mer oligonucleotides based on Structure A1, set forth in SEQ ID NOS: 26,779-26,784 and based on Structure A2, set forth in SEQ ID NOS:26,785-26,788 useful in generating dsRNA to down-regulate HEY2 expression.

SEQ ID NOS:7444-8185 provide human 19 mer oligonucleotides; SEQ ID NOS:8186-9007 provide best human-cross species oligonucleotides; SEQ ID NOS:9008-10233 provide human 18 mer oligonucleotides; and SEQ ID NOS: 10234-10533 provide best 18-mer human-cross species oligonucleotides useful in generating dsRNA to down-regulate CDKN1B expression; Table IV includes certain preferred 19 mer oligonucleotides based on Structure A1, set forth in SEQ ID NOS:26,867-26,886 and based on Structure A2, set forth in SEQ ID NOS:26,887-26,900 useful in generating dsRNA to down-regulate CDKN1B expression.

SEQ ID NOS:16622-18469 provide human 19 mer oligonucleotides; SEQ ID NOS:18470-18643 provide best human-cross species oligonucleotides; SEQ ID NOS:18644-26211 provide human 18 mer oligonucleotides; and SEQ ID NOS:26212-26666 provide best 18-mer human-cross species oligonucleotides useful in generating dsRNA to down-regulate NOTCH1 expression; Table V includes certain preferred 19 mer oligonucleotides based on Structure A1, set forth in SEQ ID NOS:26,901-26,910 and based on Structure A2, set forth in SEQ ID NOS: 26,911-26,912 useful in generating dsRNA to down-regulate NOTCH1 expression.

The oligonucleotide sequences prioritized based on their score in the proprietary algorithm as the best predicted sequences for targeting the human gene expression.

"18+1" refers to a molecule that is 19 nucleotides in length and includes a mismatch to the mRNA target at position 1 of the antisense strand, according to Structure A2. In preferred embodiments the sense strand is fully complementary to the antisense strand. In some embodiments the sense strand is mismatched to the antisense strand in 1, 2, or 3 positions.

Example 3

On-Target and Off-Target Testing of Double Stranded RNA Molecules

The psiCHECK™ system enables evaluation of the guide strand (GS) (antisense) and the passenger strand (PS) (sense strand) to elicit targeted (on-target) and off-targeted effects, by monitoring the changes in expression levels of their target sequences. Four psiCHECK™-2-based (Promega) constructs were prepared for the evaluation of target activity and potential off-target activity of each test molecule GS and PS strands. In each of the constructs one copy or three copies of either the full target or the seed-target sequence, of test molecule PS or GS, was cloned into the multiple cloning site located downstream of the Renilla luciferase translational stop codon in the 3'-UTR region.

Example 4

The Effect of Combination Treatment on Carboplatin-Induced Hair Cell Death in the Cochlea of Chinchilla Eight Chinchillas are pre-treated by direct administration of a composition or a combination of HES1 dsRNA, HES5 dsRNA and HEY2 dsRNA, in saline or by a composition or a combination of CDKN1B dsRNA, NOTCH1 dsRNA and HEY2 dsRNA in saline (to the left ear of each animal. Saline is administered to the right ear of each animal as placebo. Two days following the administration of the composition or the combination, the animals are treated with carboplatin (75 mg/kg iP). After sacrifice of the chinchillas (two weeks post carboplatin treatment) the % of dead cells of inner hair cells (IRC) and outer hair cells (ONC) is calculated in the left ear (composition/combination treated) and in the right ear (saline treated). Since the effect of the siRNA is similar across dose, the data is pooled from the 3 doses. As was previously shown, carboplatin preferentially damages the inner hair cells in the chinchilla at the 75 mg/kg dose while the outer hair cells remain intact. The compositions/combinations provided herein reduce ototoxin-induced (e.g. carboplatin-induced) inner hair cells loss in the cochlea.

Example 5

The Effect of Combination Treatment on Acoustic-Induced Hair Cell Death in the Cochlea of Chinchilla The activity of the compositions/combinations of the present invention in an acoustic trauma model is studied in chinchilla. A group of 7 animals undergo acoustic trauma by exposing them to an octave band of noise centered at 4 kHz for 2.5 h at 105 dB. The left ear of the noise-exposed chinchillas is pre-treated (48 h before the acoustic trauma) with a composition/combination of dsRNAs as disclosed herein, in saline; the right ear is pre-treated with vehicle (saline). The compound action potential (CAP) is a convenient and reliable electrophysiological method for measuring the neural activity transmitted from the cochlea. The CAP is recorded by placing an electrode near the base of the cochlea in order to detect the local field potential that is generated when a sound stimulus, such as click or tone burst, is abruptly turned on. The functional status of each ear is assessed at about 2.5 weeks after the acoustic trauma. Specifically, the mean threshold of the compound action potential recorded from the round window is determined 2.5 weeks after the acoustic trauma in order to determine if the thresholds in the composition/combination treated ear were lower (better) than the untreated (saline) ear. In addition, the amount of inner and outer hair cell loss is determined in the composition/combination treated and the control ear. The results indicate that the compositions/combinations provided herein, reduce acoustic trauma-induced ONC loss in the cochlea.

Example 6

The Effect of Combination Treatment on Cisplatin-Induced Hair Cell Death in the Cochlea of Rats Male Wistar Rats are tested for basal auditory brainstem response (ABR) thresholds for signals of clicks, 8, 16 and 32 kHz prior to cisplatin treatment. Following the basal auditory brainstem response testing, cisplatin is administered as an intraperitoneal infusion of 12 mg/kg over 30 minutes. Treated ears receive the dsRNA compositions/combinations disclosed herein in PBS (applied directly to the round window membrane). Control ears are treated either with non-related GFP dsRNA or PBS. The compositions/combinations are administered between 3-5 days prior to cisplatin administration in order to permit protective effect on the cochlea.

The auditory brainstem response (ABR) testing is repeated 3 days after cisplatin administration. The auditory brainstem response thresholds are compared between pre-treatment and post treatment and the shift in thresholds is measured. Higher shift in thresholds following cisplatin treatment is indicative for more severe hair cells loss in the cochlea. After the repeat of auditory brainstem response testing, animals are sacrificed and cochleae are removed and processed for scanning electron microscopy (SEM) to quantify outer hair cell (ONC) loss in the hook region (high frequency region). The % outer hair cell loss is calculated by dividing the number of missing or severely damaged cells by the total number of outer hair cells in the field of the photograph. The results indicate that compositions/combinations disclosed herein provide a protective effect to the cochlea when administered prior to ototoxin (e.g. cisplatin) administration.

Example 7

Additional Hearing Loss Models

A) Hearing Regeneration (Plasticity) Model in Guinea-Pig

Deafness is induced by systemically treating albino guinea pigs with a single is injection of kanamycin (450-500 mg/kg) followed by a single iv (jugular) injection of ethacrynic acid (EA). This pharmacological deafening eliminates bilaterally all hair cells approximately after 1-2 days and leaves the supporting cells differentiated. Therapeutic composition/combination as disclosed herein are applied to the middle ear by transtympanic injection (TT) or into the external auditory canal or eardrum by ear drops (ErD).

The efficacy of the compositions/combinations is examined as follows:
1) Cochleae/s are morphologically analyzed as wholemounts stained for myosin VIIa (hair cell marker) and phalloidin.
2) BrdU incorporation is measured as an indicator of proliferation rate of hair cells.

B) Noise Induced Acute Hearing Loss Model in Guinea Pig

Noise can cause hearing damage with temporary or permanent sensorineural hearing loss (SNHL) and tinnitus. SNHL and tinnitus can occur singular or in combination. In humans, noise induced hearing loss (NIHL) is demonstrated by a threshold shift in the pure tone audiogram, in recruitment, in pathological results of supra-threshold hearing tests and in amplitude decline of oto-acoustic emissions. Hearing damage is induced by exposure to continuous noise or impulsive noise. In addition the possibility of impulse noise traumata or explosion trauma should be taken into consideration. Exposure to impulse noise can result in a more severe lesion of the inner ear than exposure to continuous noise. Important criteria for the development of noise damage are sound pressure level (SPL), level increase velocity, exposure time, as well as individual susceptibility ("the vulnerable inner ear"). Noise exposure usually leads to an elevation of threshold which may be later resolved in part, such that the temporary component is called "temporary threshold shift" (TTS). If there isn't complete restitution in the recovery phase after TTS, this may result in permanent inner ear damage (permanent threshold shift=PTS). Very high sound intensity may lead to immediate cellular death and mechanical rupture of structures in the inner ear and PTS.

In this model, a bilateral lesion is induced with noise exposure; Guinea pigs are exposed to 117 dB SPL broadband noises for 6 hours.

In a pilot study according to this model, the compositions/combinations as disclosed herein are employed in this model with beneficial result.

Example 8

The Effect of Combination Treatment on Noise-Induced Death of Otic Sensory Cells of the Inner Ear Model system: Exposure of guinea pigs to one-octaveband noise centered at 6 kHz, at 130 dB SPL for 2 hours (Futon et al, NeuroReport 19:277-281, 2008)

Experimental Groups

Adult Hartley albino guinea pigs (age 3 months), with normal Preyer's reflex, are exposed to noise and randomized to the following groups: noise control group without treatment (n=6), noise control animals with vehicle (n=6), animals treated with the composition/combination provided herein at a dose of 1 µg (n=6); animals treated with the compositions/combinations provided herein at a dose of 5 µg (n=6); animals treated with the compositions/combinations provided herein at a dose of 10 µg (n=6); animals treated with the compositions/combinations provided herein at a dose of 50 µg (n=6); 4 groups of noise control animals with control dsRNA compound which down-regulates expression of EGFP gene (each n=6), at a dose of 1 µg, 5 µg, 10 µg and 50 µg respectively.

Treatment is performed 1 h before noise exposure and once daily for 3 days thereafter.

The following exemplary vehicles are used in this experiment: PBS, artificial perilymph solution.

The compositions/combinations as provided herein are formulated for administration in the vehicle of the experiment.

Vehicle, the compositions/combinations as provided herein or dsRNA control compound, is injected intraperitoneally or by bolus injection. All animals are sacrificed after functional evaluation with a lethal dose of anesthetic: three animals for each group at day 1 for immunolabeling and the remaining animals at day 21, of which three are further processed for scanning electron microscopy (SEM).

Noise Exposure

Acoustic trauma is induced by a continuous pure tone of 6 kHz generated by a waveform generator (for example: Generator LAG-120B, Leader Electronics Corp, Yokohama, Japan), and amplified by an audio amplifier (for example: A-207R, Pioneer Electronics, Long Beach, Calif., USA). All animals, under anesthetic, are exposed for 40 min to a 6 kHz, 120 db SPL (Sound Pressure Level) sound presented in an open field (for example: dome tweeter TW340×0, Audax, Chateau de Loir, France).

Electrophysiological Measurements of Auditory Function

Auditory brainstem responses (ARB) are measured before noise exposure and 1 h, 3 days, 7 days and 21 days after noise exposure. Animals are mildly anaesthetized and placed in a soundproof room. Three electrodes are subcutaneously inserted into the right mastoid (active), vertex (reference) and left mastoid (ground). A computer-controlled data acquisition system, for example TDT System 3 (Tucker-Davis Technologies, Alachu, Fla., USA) data acquisition system with real-time digital signal processing is used to record the ABR and to generate the auditory stimulus. Tone bursts of pure tones ranging from 2 to 24 kHz (rise/fall time, 1 ms; total duration, 10 ms; repetition rate, 20/s) is presented monoaurally in an open field. Responses are filtered (0.3-3 kHz), digitized and averaged across 500 discrete samples at each frequency-level combination.

Morphological Studies: Scanning Electron Microscopy

SEM analysis is performed, e.g. as described in Sergi B, et al. Protective properties of idebenone in noise-induced hearing loss in the guinea pig. *NeuroReport* 2006; 17:857-861. Briefly, the cochlea (n=3) of three animals for each group is perfused with 2.5% glutaraldehyde in 0.1 M phosphate buffer and post-fixed overnight and then incubated for 2 h in 2% osmium tetroxide cacodylate buffer. After microdissection, the cochlea is dehydrated with increasing concentrations of ethanol from 30 to 100% and dried in the critical point and finally coated with gold. Each specimen is viewed and photographed by means of, e.g. a Zeiss Supra 50 Field Emission SEM apparatus (Carl Zeiss Inc., Gottingen, Germany). Quantitative EM observations of the surface morphology of the organ of Corti are performed by determining the number of hair cells in 20 segments (1 mm length of basilar membrane each). A hair cell is counted as missing if the stereociliary bundle is absent or the stereocilia of the bunch are completely fused. Results of hair cell counts are expressed as the percentage of remaining hair cells in each row of inner hair cells and outer hair cells over the entire length of cochlea.

Terminal Deoxynucleotidyl Transferase Mediated dUTP Nick End Labeling Assay

The cochlea (n=3) of three animals for each group are stained by using TUNEL (terminal deoxynucleotidyl transferase-mediated dUTP nick end labeling) assay (for example, Molecular Probes, Inc., Carslbad, Calif., USA) as described in B Sergi et al. Protective properties of idebenone in noise-induced hearing loss in the guinea pig. *NeuroReport* (2006) 17:857-861. Briefly, the cochlea are fixed with 10% formaldehyde in 0.1 M phosphate-buffered saline (PBS), pH 7.3. After micro-dissection, surface preparations of the organ of Corti are incubated in ice-cold 70% (v/v) ethanol overnight and then in freshly prepared DNA labeling solution containing 10 µl of reaction buffer, 0.75 µl of TdT enzyme, 8.0 µl of BrdUTP and 31.25 µl of dH$_2$O for 16 h at room temperature. The tissues are then stained with Alexa Fluor 488 dye-labelled anti BrdU antibody—contained in the TUNEL assay kit (e.g., Molecular Probes Inc., Carlsbad, Calif., USA) (5 µl of antibody plus 95 µl of the Corti are double stained with propidium iodide (5 µg/ml in 10 mM PBS) for 20 min at room temperature. After rinsing in PBS, the organs of Corti are mounted on slides containing an anti-fade medium (for example, Prolong Gold, Molecular Probes, Inc.). Specimens are observed using confocal laser scanning microscopy (e.g., Leica TCS-SP2, Leica Inc., Wetzlar, Germany).

Results

The results obtained in this model indicate that the compositions/combinations provided herein: (a) attenuated noise-induced threshold shift; and (b) decreased noise-induced outer hair cell loss; provided protection against noise-induced hearing loss (NIHL).

Example 9

Therapeutic Activity of Combination Treatments in Hair Cell Regeneration in Rat Model of Ototoxic Hearing Loss Model system. 40 ul of cocktail Kanamycin (200 mg/ml) and ethacrynic acid (20 mg/ml) in PBS (pH 8) were administered by transtympanic injection. 6 groups of rats (N=5, 4 or 3) were used.

In groups 1-4, animals (Wistar and Norway Brown young adult male rats (180-220 g)) were bilaterally deafened using a combined treatment with transtympanic administration of kanamycin (KM) and ethacrynic acid (EA) cocktail, as described above. Animals in group 5 had one ear deafened as above while receiving PBS in the contralateral ear. Animals in group 6 remained undeafened. dsRNA to EGFP was used as control siRNA. Test or control siRNAs were delivered to groups 1-4 as assigned below. Groups 5 and 6 did not receive combination/control siRNA treatment.

The following groups were performed (total n=25):

Group 1 (5 rats): KM+EA. Left ear: control, Right ear: combination of HES1 dsRNA+HEY2 dsRNA+HES5 dsRNA;

Group 2 (5 rats): KM+EA. Left ear: control, Right ear: combination of HES1 dsRNA+HEY2 dsRNA+EGFP dsRNA);

Group 3 (5 rats): KM+EA. Left ear: control, Right ear: combination of NOTCH1 dsRNA+CDKN1B dsRNA+HEY2 dsRNA;

Group 4 (4 rats): KM+EA. Left ear: control, Right ear: EGFP dsRNA (control siRNA);

Group 5 (3 rats): KM+EA. Left ear: control, Right ear: vehicle;

Group 6 (3 rats): Normal control. Left ear: un-operated. Right ear: sham-operated (surgical procedure)

Details of dsRNA combinations administration: control siRNA or dsRNA combinations were administered by combined GelFoam and pump administration, as follows.

On day 4 after KM+EA administration, control siRNA or dsRNA combinations were administered to the anesthetized animals via surgical procedure of opening the bulla and applying a 3 µl volume of control siRNA or combinations of dsRNAs (see Table B for bolus dsRNA doses) on a small piece of GelFoam placed on the round window membrane. Next, the catheter of a 2006 Alzet miniosmotic pump was placed on a GelFoam in the adequate orientation and secured to the bulla. The catheter was then connected to the pump filled with 200 µl volume of control siRNA or dsRNA combinations (see Table B for pump dsRNA doses), followed by pump implantation between the 2 scapulae. Control siRNA or dsRNA combinations were applied continuously over a period of 6 weeks via 2006 Alzet miniosmotic pump.

TABLE B dsRNA doses

| Group No. | dsRNA/dsRNA combination | GelFoam dose, µg of each (in total volume of 3 µl/foam piece/ear) | Dose in a 6 weeks pump, µg of each (in total volume of 200 µl/ear) |
|---|---|---|---|
| 1 | HES1 + HEY2 + HES5 | 30 µg + 30 µg + 30 µg | 30 µg + 30 µg + 30 µg |
| 2 | HES1 + HEY2 + EGFP | 30 µg + 30 µg + 30 µg | 30 µg + 30 µg + 30 µg |
| 3 | NOTCH1 + CDKN1B + HEY2 | 30 µg + 30 µg + 30 µg | 30 µg + 30 µg + 30 µg |
| 4 | EGFP (control siRNA) | 90 µg | 90 µg |

Details of dsRNA compounds: Table C hereinbelow provides details of chemically modified dsRNA compounds that were used in this model system.

TABLE C

| dsRNA type/ Name | Sense 5 -> 3 | Antisense 5 -> 3 |
|---|---|---|
| NOTCH1/ NOTCH1_2_S2085 | zidB; rG; rC; rU; rA; rC; rA; rA; rC; rU; rG; rC; rG; rU; rG; rU2p; rG2p; rU2p; rG2p; rA2p; zc3p | mU; rC; rA; rC; rA; rC; rA2p; rC; rG; rC; rA; rG; rU; rU; rG; rU; mA; rG; rC; zc3p; zc3p |

TABLE C-continued

| dsRNA type/ Name | Sense 5 -> 3 | Antisense 5 -> 3 |
|---|---|---|
| CDKN1B/ CDKN1B_4_S2102 | zc6Np; rG; mC; rA; rA; rU; mU; rA; rG; rG; rU; rU; rU; rU; rU; mC; rC; rU; mU; rA; zc3p | 5'p; mU; rA; rA; rG; rG; rA; mA; rA; rA; rA; rC; rC; mU; rA; rA; rU; mU; rG; rC; zc3p; zc3p$ |
| HEY2/ HEY2_2_S1970 | zidB; rG; rG; rG; mU; rA; rA; rA; rG; rG; rC; mU; rA; mC; rU; rU; mU; rG; rA; rA; zc3p | mU; rU; mC; rA; rA; rA; rG2p; mU; rA; rG; mC; rC; mU; rU; mU; rA; mC; rC; mC; zc3p; zc3p |
| HES1/ HES1_36_S2086 | zidB; rC; rA; rG; rC; rG; rA; rG; rU; rG; rC; rA; rU; rG; rA; rA2p; rC2p; rG2p; rA2p; rU2p; zc3p | rA; rU; mC; rG; rU; rU; rC; rA; mU; rG; mC; rA; rC; rU; mC; rG; rC; rU; rG; zc3p; zc3p |
| EGFP/ EGFP_5_S763 | rG; mG; rC; mU; rA; mC; rG; mU; rC; mC; rA; mG; rG; mA; rG; mC; rG; mC; rA; mC; rC$ | mG; rG; mU; rG; mC; rG; mC; rU; mC; rC; mU; rG; mG; rA; mC; rG; mU; rA; mG; rC; mC$ |
| HES5/ HES5_8_S500 | rG; mG; rG; mU; rU; mC; rU; mA; rU; mG; rA; mU; rA; mU; rU; mU; rG; mU; rA | mU; rA; mC; rA; mA; rA; mU; rA; mU; rC; mA; rU; mA; rG; mA; rA; mC; rC; mC |

Table D hereinbelow provides a legend of the modified ribonucleotides/unconventional moieties utilized in the dsRNA compounds in Table C.

TABLE D

| Legend | |
|---|---|
| Code | Modification |
| Nuc | |
| c6Np | Amino modifier C6 (Glen Research) |
| iB | inverted deoxyabasic |
| mA | 2'-O-methyladenosine-3'-phosphate |
| mA$ | 2'-O-methyladenosine (no phosphate) |
| mC | 2'-O-methylcytidine-3'-phosphate |
| mC$ | 2'-O-methylcytidine (no 3'-phosphate) |
| mG | 2'-O-methylguanosine-3'-phosphate |
| mG$ | 2'-O-methylguanosine (no phosphate) |
| mU | 2'-O-methyluridine-3'-phosphate |
| mU$ | 2'-O-methyluridine (no phosphate) |
| rA | riboadenosine-3'-phosphate |
| rA$ | riboadenosine (no phosphate) |
| rA2p | riboadenosine-2'-phosphate |
| rC | ribocytidine-3'-phosphate |
| rC$ | ribocytidine (no phosphate) |
| rC2p | ribocytidine-2'-phosphate |
| rG | riboguanosine-3'-phosphate |
| rG2p | riboguanosine-2'-phosphate |
| rU | ribouridine-3'-phosphate |
| rU$ | ribouridine (no phosphate) |
| rU2p | ribouridine-2'-phosphate |
| p | 5'-phosphate |
| z | Prefix for Capping moiety |
| zc3p | C3Pi covalently attached |
| zc3p$ | C3OH covalently attached |
| $ | No terminal phosphate |

Schedule of ABR/DPOAE measurements: For all animals outlined in Table B above, damage baseline ABR/DPOAE was measured on days 3 or 4 after KM+EA administration, but prior to surgery/dsRNA combinations/dsRNA control administration on day 4. For ABR and DPOAE recording: the rat was anesthetized with a Ketamine (40 mg/kg)-Xylazine (5 mg/kg) cocktail.

In addition, all the animals were tested for ABR/DPOAE on weeks 3, 5, 7 and 9. In addition, all animals are tested for ABR/DPOAE at week 11.

Euthanasia of the animals and histology studies: all experimental animals were euthanized on week 11 after dsRNA combinations/dsRNA control administration (after ABR/DPOAE tests on week 11). Inner ear tissues were harvested and subjected to histology studies, qPCR study for target genes and Atoh1 mRNA levels; RACE analysis of the cleavage products, etc.

Figure 1B:
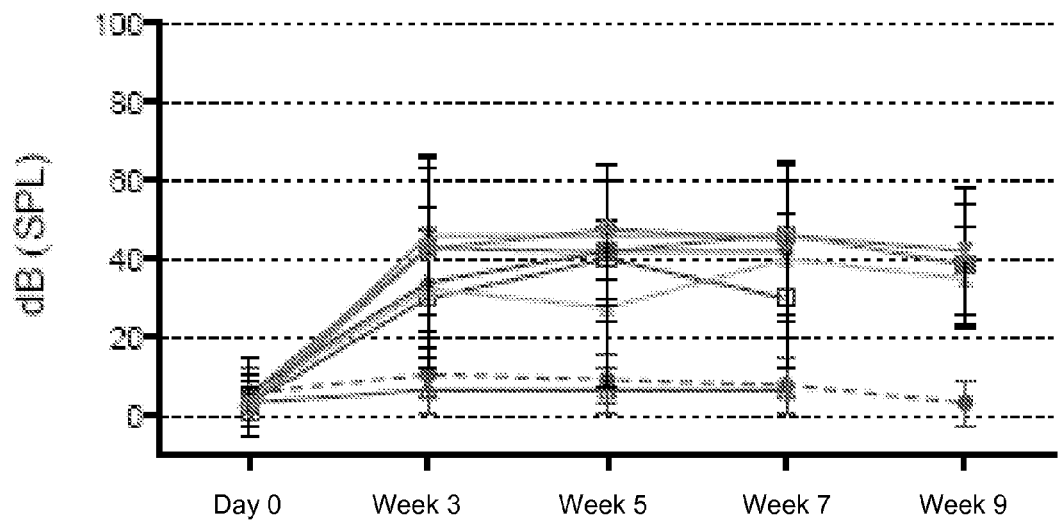
Figure 1C:
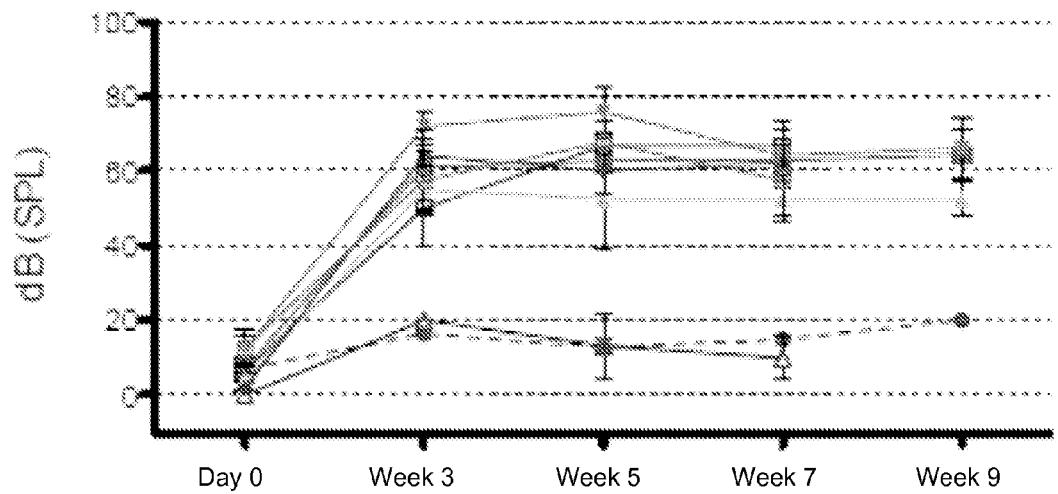
Figure 1D:
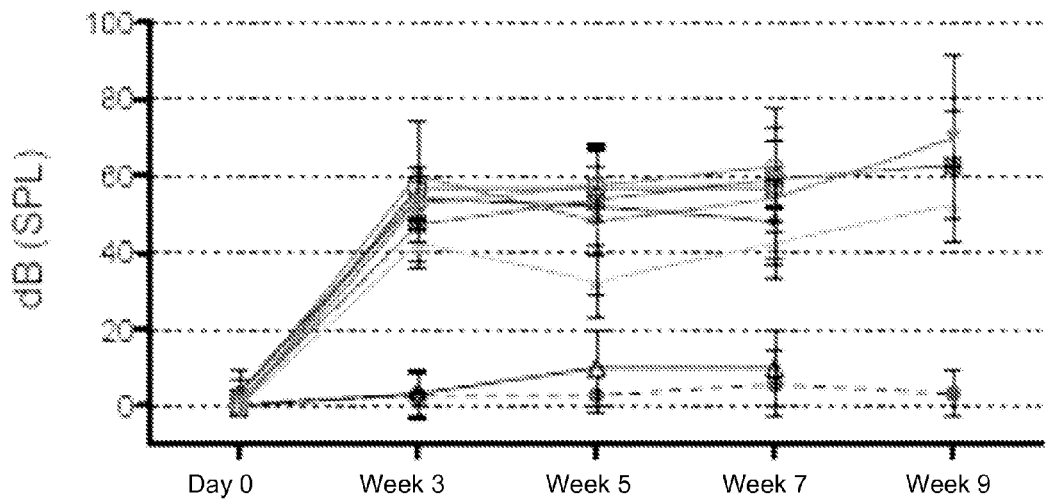
Figures 1E, 1F:
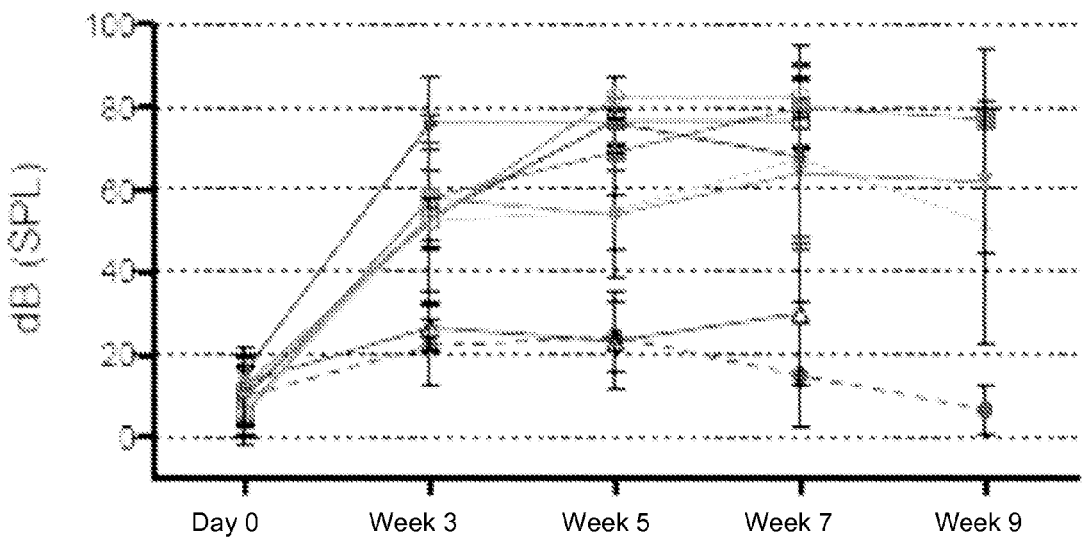
FIG. 1F provides the legend for FIGS. 1A-1E.

Results: FIGS. 1A-1E show the ABR response obtained in this study at Day 0, after 3 weeks, after 5 weeks, after 7 weeks and after 9 weeks. FIG. 1A shows the ABR response obtained in this study at Day 0, after 3 weeks, after 5 weeks, after 7 weeks and after 9 weeks for 1 KHz stimulus. FIG. 1B shows the ABR response obtained in this study at Day 0, after 3 weeks, after 5 weeks, after 7 weeks and after 9 weeks for 4 KHz stimulus. FIG. 1C shows the ABR response obtained in this study at Day 0, after 3 weeks, after 5 weeks, after 7 weeks and after 9 weeks for 8 KHz stimulus. FIG. 1D shows the ABR response obtained in this study at Day 0, after 3 weeks, after 5 weeks, after 7 weeks and after 9 weeks for 16 KHz stimulus. FIG. 1E shows the ABR response obtained in this study at Day 0, after 3 weeks, after 5 weeks, after 7 weeks and after 9 weeks for 32 KHz stimulus. FIG. 1F provides the legend for FIGS. 1A-1E.

Table E hereinbelow provides explanation of the legend for the test groups in FIGS. 1A-1E.

TABLE E

| Explanation of the legend for the test groups in the Figures | |
|---|---|
| Legend | Explanation |
| "Contralateral" | Normal control. Left ear: un-operated. Right ear: sham-operated (surgical procedure) |
| "PBS + vehicle" | Left ear: control, Right ear: PBS + Vehicle, which is artificial perilymph |
| KM + EA | KM + EA. Left ear: control, Right ear: vehicle (artificial perilymph) |

TABLE E-continued

Explanation of the legend for the test groups in the Figures

| Legend | Explanation |
|---|---|
| KM + EA + vehicle | KM + EA + vehicle (artificial perilymph). Left ear: control, Right ear: vehicle |
| KM + EA + combination of HES1 dsRNA + HES5 dsRNA + HEY2 dsRNA | KM + EA. Left ear: control, Right ear: combination of HES1 dsRNA + HES5 dsRNA + HEY2 dsRNA |
| KM + EA + combination of HES1 dsRNA + HEY2 dsRNA + EGFP dsRNA | KM + EA. Left ear: control, Right ear: combination of HES1 dsRNA + HEY2 dsRNA + EGFP dsRNA |
| KM + EA + combination of NOTCH1 dsRNA + CDKN1B dsRNA + HEY2 dsRNA | KM + EA. Left ear: control, Right ear: combination of NOTCH1 dsRNA + CDKN1B dsRNA + HEY2 dsRNA |
| KM + EA + EGFP dsRNA | KM + EA. Left ear: control, Right ear: EGFP dsRNA - (control siRNA) |

FIGS. 1A-1E show that combination of HES1 dsRNA+HES5 dsRNA+HEY2 dsRNA and combination of NOTCH1 dsRNA+CDKN1B dsRNA+HEY2 dsRNA were effective in significantly improving ABR response in this model of ototoxin-induced hearing loss.

Example 10

Treatment of Disorders with Impaired Vestibular Function

An animal model useful for testing the combinations, compositions and methods disclosed herein for improving vestibular function may be found in Schlecker C, et al., Selective atonal gene delivery improves balance function in a mouse model of vestibular disease. Gene Ther. 2011 September; 18(9):884-90, incorporated herein by reference in its entirety.

Although the above examples have illustrated particular ways of carrying out embodiments of the invention, in practice persons skilled in the art will appreciate alternative ways of carrying out embodiments of the invention, which are not shown explicitly herein. It should be understood that the present disclosure is to be considered as an exemplification of the principles of this invention and is not intended to limit the invention to the embodiments illustrated.

Those skilled in the art will recognize, or be able to ascertain using no more than routine experimentation, equivalents of the specific embodiments of the invention described herein. Such equivalents are intended to be encompassed by the following claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09434946B2). An electronic copy of the "Sequence Listing" will also be available from the USPTO upon request and payment of the fee set forth in 37 CFR 1.19(b)(3).

We claim:

1. A method of preventing, treating or delaying the progression of a hearing disorder, a hearing loss and/or a balance impairment in a subject, or preventing the loss of otic (sensory) hair cells of the inner ear in a subject comprising administering to the subject
    (i) a combination of a HES1 (SEQ ID NO:1) inhibitor, a HES5 (SEQ ID NO:2) inhibitor and a HEY2 (SEQ ID NO:10) inhibitor; or
    (ii) a combination of a CDKN1B (SEQ ID NO:7) inhibitor, a NOTCH1 (SEQ ID NO:11) inhibitor and a HEY2 (SEQ ID NO:10) inhibitor,
    wherein the inhibitors are double stranded oligonucleotides.

2. The method of claim 1, wherein the combination of inhibitors is administered to the subject in the same formulation.

3. The method of claim 1, wherein the combination of inhibitors is administered to the subject in the different formulations.

4. The method of claim 1, wherein the combination of inhibitors is administered to the subject by different routes.

5. The method of claim 1, wherein one or more inhibitors is administered to the subject separately or sequentially.

6. The method of claim 1, wherein one or more inhibitors is administered to the subject substantially simultaneously.

7. The method of claim 1, wherein the inhibitors are co-administered to the subject by transtympanic injection or topically.

8. The method of claim 7, wherein the topical administration comprises application of ear drops to the eardrum.

9. The method of claim 1, wherein each of the double-stranded oligonucleotides comprises a strand configured to specifically bind mRNA encoding HES1, HES5, HEY2, CDKN1B or NOTCH1.

10. The method of claim 1, wherein each of the double-stranded oligonucleotides comprises a dsRNA molecule having a sense strand and an antisense strand and the double-stranded oligonucleotides are linked or annealed in a RNAistar formation.

11. The method of claim 1, wherein:
each double-stranded oligonucleotide comprises a sense strand and an antisense strand, wherein:
(a) each strand is independently 18 to 49 nucleotides in length;
(b) a 18 to 49 nucleotide sequence of the antisense strand is complementary to a sequence of an mRNA encoding (i) HES1, HES5 or HEY2 respectively, or (ii) CDKN1B, NOTCH1, or HEY2 respectively; and
(c) a 18 to 49 nucleotide sequence of the sense strand is complementary to the antisense strand.

12. The method of claim 1, wherein at least one double-stranded oligonucleotide independently comprises a structure (A1):

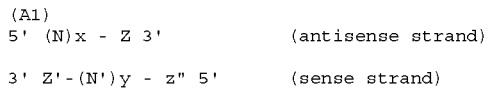

wherein each of N and N' is a ribonucleotide which may be unmodified or modified, or an unconventional moiety;
each of (N)x and (N')y is an oligonucleotide in which each consecutive N or N' is joined to the next N or N' by a covalent bond;
each of Z and Z' is independently present or absent, but if present is independently 1-5 consecutive nucleotides, 1-5 consecutive non-nucleotide moieties or a combination thereof covalently attached at the 3' terminus of the strand in which it is present;
z" may be present or absent, but if present is a capping moiety covalently attached at the 5' terminus of (N')y;
each of x and y is independently an integer between 18 and 40;
the sequence of (N')y is complementary to the sequence of (N)x; and
(N)x comprises an antisense sequence complementary to an mRNA selected from (i) an mRNA encoding HES1, an mRNA encoding HES5, or an mRNA encoding HEY2, or (ii) an mRNA encoding CDKN1B, an mRNA encoding NOTCH1 or an mRNA encoding HEY2.

13. The method of claim 1, wherein at least one double-stranded oligonucleotide independently comprises a structure (A2):

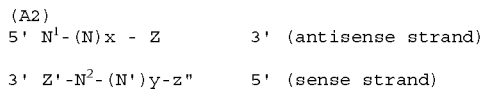

wherein each of N2, N and N' is independently an unmodified or modified ribonucleotide, or an unconventional moiety;
each of (N)x and (N')y is an oligonucleotide in which each consecutive N or N' is joined to the adjacent N or N' by a covalent bond;
each of x and y is independently an integer between 17 and 39;
N2 is covalently bound to (N')y;
N1 is covalently bound to (N)x and is mismatched to the target mRNA selected from HES1 mRNA, HES5 mRNA, HEY2 mRNA, CDKN1B mRNA and NOTCH1 mRNA or is a complementary deoxyribonucleotide moiety to the mRNA selected from HES1 mRNA, HES5 mRNA, HEY2 mRNA, CDKN1B mRNA and NOTCH1 mRNA;
N1 is a moiety selected from the group consisting of natural or modified: uridine, deoxyribouridine, ribothymidine, deoxyribothymidine, adenosine or deoxyadenosine, an abasic ribose moiety and an abasic deoxyribose moiety;
z" may be present or absent, but if present is a capping moiety covalently attached at the 5' terminus of N2-(N')y; and
each of Z and Z' is independently present or absent, but if present is independently 1-5 consecutive nucleotides, 1-5 consecutive non-nucleotide moieties or a combination thereof covalently attached at the 3' terminus of the strand in which it is present;
the sequence of (N')y has complementarity to the sequence of (N)x; and
the sequence of (N)x has complementarity to a consecutive sequence selected from a sequence in HES1 mRNA (SEQ ID NO:1), HES5 mRNA (SEQ ID NO:2), HEY2 mRNA (SEQ ID NO:10), CDKN1B mRNA (SEQ ID NO:7) and NOTCH1 mRNA (SEQ ID NO:11).

14. The method of claim 1, wherein the combination being administered is (i).

15. The method of claim 1, wherein the combination being administered is (ii).

16. The method of claim 1, wherein the subject is human.

17. The method of claim 1, wherein the inhibitors are administered in an amount and for a period of time sufficient to prevent, treat or delay the progression of the hearing disorder, the hearing loss and/or the balance impairment in the subject, or to prevent the loss of otic (sensory) hair cells of the inner ear in the subject.

* * * * *